(12) United States Patent
Weber et al.

(10) Patent No.: US 7,931,683 B2
(45) Date of Patent: Apr. 26, 2011

(54) ARTICLES HAVING CERAMIC COATED SURFACES

(75) Inventors: Jan Weber, Maastricht (NL); Michele Zoromski, Minneapolis, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 583 days.

(21) Appl. No.: 11/881,766

(22) Filed: Jul. 27, 2007

(65) Prior Publication Data

US 2009/0138077 A1 May 28, 2009

(51) Int. Cl.
*A61F 2/06* (2006.01)
(52) U.S. Cl. ....................................... 623/1.42
(58) Field of Classification Search ........ 623/1.42–1.46, 623/1.15, 1.13, 23.72, 23.73, 23.74, 23.75, 623/23.29, 23.3, 23.36, 23.55, 23.56, 23.57, 623/1.4–1.54; 604/891.1; 427/2.1, 2.24
See application file for complete search history.

(56) References Cited

U.S. PATENT DOCUMENTS

| | | |
|---|---|---|
| 3,751,283 A | 8/1973 | Dawson |
| 3,758,396 A | 9/1973 | Vieth et al. |
| 3,910,819 A | 10/1975 | Rembaum et al. |
| 3,948,254 A | 4/1976 | Zaffaroni |
| 3,952,334 A | 4/1976 | Bokros et al. |
| 3,970,445 A | 7/1976 | Gale et al. |
| 3,993,072 A | 11/1976 | Zaffaroni |
| 4,044,404 A | 8/1977 | Martin et al. |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,321,311 A | 3/1982 | Strangman |
| 4,330,891 A | 5/1982 | Branemark et al. |
| 4,334,327 A | 6/1982 | Lyman et al. |
| 4,401,546 A | 8/1983 | Nakamura et al. |
| 4,407,695 A | 10/1983 | Deckman et al. |
| 4,475,972 A | 10/1984 | Wong |
| 4,565,744 A | 1/1986 | Walter et al. |
| 4,585,652 A | 4/1986 | Miller et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,733,665 A | 3/1988 | Palmaz |

(Continued)

FOREIGN PATENT DOCUMENTS

AT          232704          3/2003

(Continued)

OTHER PUBLICATIONS

PCT/US2008/070822, Boston Scientific SCIMED, Inc. Jul. 2008.*

(Continued)

*Primary Examiner* — Alvin J. Stewart
(74) *Attorney, Agent, or Firm* — Fish & Richardson P.C.

(57) ABSTRACT

According to an aspect of the invention, articles are provided which comprise a substrate and a ceramic coating which covers at least a portion of the substrate surface. The ceramic coating includes raised ceramic shells connected by a ceramic layer that is conformal with the substrate. According to another aspect of the present invention, carbon nanotubes are provided, which comprise a ceramic coating covering at least a portion of the carbon nanotubes.

29 Claims, 12 Drawing Sheets

U.S. PATENT DOCUMENTS

| | | |
|---|---|---|
| 4,738,740 A | 4/1988 | Pinchuk et al. |
| 4,743,252 A | 5/1988 | Martin et al. |
| 4,784,659 A | 11/1988 | Fleckenstein et al. |
| 4,800,882 A | 1/1989 | Gianturco |
| 4,842,505 A | 6/1989 | Annis et al. |
| 4,886,062 A | 12/1989 | Wiktor |
| 4,902,290 A | 2/1990 | Fleckenstein et al. |
| 4,954,126 A | 9/1990 | Wallsten |
| 4,976,692 A | 12/1990 | Atad |
| 4,994,071 A | 2/1991 | MacGregor |
| 5,061,275 A | 10/1991 | Wallsten et al. |
| 5,061,914 A | 10/1991 | Busch et al. |
| 5,073,365 A | 12/1991 | Katz et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,171,607 A | 12/1992 | Cumbo |
| 5,195,969 A | 3/1993 | Wang et al. |
| 5,205,921 A | 4/1993 | Shirkanzadeh |
| 5,219,611 A | 6/1993 | Giannelis et al. |
| 5,232,444 A | 8/1993 | Just et al. |
| 5,236,413 A | 8/1993 | Feiring |
| 5,250,242 A | 10/1993 | Nishio et al. |
| 5,270,086 A | 12/1993 | Hamlin |
| 5,279,292 A | 1/1994 | Baumann et al. |
| 5,290,585 A | 3/1994 | Elton |
| 5,302,414 A | 4/1994 | Alkhimov et al. |
| 5,304,121 A | 4/1994 | Sahatjian |
| 5,314,453 A | 5/1994 | Jeutter |
| 5,322,520 A | 6/1994 | Milder |
| 5,326,354 A | 7/1994 | Kwarteng |
| 5,348,553 A | 9/1994 | Whitney |
| 5,366,504 A | 11/1994 | Andersen et al. |
| 5,368,881 A | 11/1994 | Kelman et al. |
| 5,378,146 A | 1/1995 | Sterrett |
| 5,380,298 A | 1/1995 | Zabetakis et al. |
| 5,383,935 A | 1/1995 | Shirkhanzadeh |
| 5,397,307 A | 3/1995 | Goodin |
| 5,405,367 A | 4/1995 | Schulman et al. |
| 5,439,446 A | 8/1995 | Barry |
| 5,443,496 A | 8/1995 | Schwartz et al. |
| 5,447,724 A | 9/1995 | Helmus et al. |
| 5,449,373 A | 9/1995 | Pinchasik et al. |
| 5,449,382 A | 9/1995 | Dayton |
| 5,464,450 A | 11/1995 | Buscemi et al. |
| 5,464,650 A | 11/1995 | Berg et al. |
| 5,474,797 A | 12/1995 | Sioshansi et al. |
| 5,500,013 A | 3/1996 | Buscemi et al. |
| 5,527,337 A | 6/1996 | Stack et al. |
| 5,545,208 A | 8/1996 | Wolff et al. |
| 5,551,954 A | 9/1996 | Buscemi et al. |
| 5,569,463 A | 10/1996 | Helmus et al. |
| 5,578,075 A | 11/1996 | Dayton |
| 5,587,507 A | 12/1996 | Kohn et al. |
| 5,591,224 A | 1/1997 | Schwartz et al. |
| 5,603,556 A | 2/1997 | Klink |
| 5,605,696 A | 2/1997 | Eury et al. |
| 5,607,463 A | 3/1997 | Schwartz et al. |
| 5,607,467 A | 3/1997 | Froix |
| 5,609,629 A | 3/1997 | Fearnot et al. |
| 5,614,549 A | 3/1997 | Greenwald et al. ............ 514/449 |
| 5,624,411 A | 4/1997 | Tuch |
| 5,649,951 A | 7/1997 | Davidson |
| 5,649,977 A | 7/1997 | Campbell |
| 5,672,242 A | 9/1997 | Jen |
| 5,674,192 A | 10/1997 | Sahatjian et al. |
| 5,674,242 A | 10/1997 | Phan et al. |
| 5,679,440 A | 10/1997 | Kubota |
| 5,681,196 A | 10/1997 | Jin et al. |
| 5,690,670 A | 11/1997 | Davidson |
| 5,693,085 A | 12/1997 | Buirge et al. |
| 5,693,928 A | 12/1997 | Egitto et al. |
| 5,711,866 A | 1/1998 | Lashmore et al. |
| 5,733,924 A | 3/1998 | Kanda et al. |
| 5,733,925 A | 3/1998 | Kunz et al. .................... 514/449 |
| 5,741,331 A | 4/1998 | Pinchuk |
| 5,744,515 A | 4/1998 | Clapper |
| 5,749,809 A | 5/1998 | Lin |
| 5,758,562 A | 6/1998 | Thompson |
| 5,761,775 A | 6/1998 | Legome et al. |
| 5,769,883 A | 6/1998 | Buscemi et al. |
| 5,772,864 A | 6/1998 | Moller et al. |
| 5,776,184 A | 7/1998 | Tuch |
| 5,780,807 A | 7/1998 | Saunders |
| 5,788,687 A | 8/1998 | Batich et al. |
| 5,788,979 A | 8/1998 | Alt et al. |
| 5,795,626 A | 8/1998 | Gabel et al. |
| 5,797,898 A | 8/1998 | Santini, Jr. et al. |
| 5,807,407 A | 9/1998 | England et al. |
| 5,817,046 A | 10/1998 | Glickman |
| 5,824,045 A | 10/1998 | Alt |
| 5,824,048 A | 10/1998 | Tuch |
| 5,824,049 A | 10/1998 | Ragheb et al. |
| 5,824,077 A | 10/1998 | Mayer |
| 5,830,480 A | 11/1998 | Ducheyne et al. |
| 5,837,313 A | 11/1998 | Ding et al. |
| 5,843,089 A | 12/1998 | Sahatjian et al. |
| 5,843,172 A | 12/1998 | Yan |
| 5,852,088 A | 12/1998 | Dismukes et al. |
| 5,858,556 A | 1/1999 | Eckert et al. |
| 5,873,904 A | 2/1999 | Ragheb et al. |
| 5,874,134 A | 2/1999 | Rao et al. |
| 5,879,697 A | 3/1999 | Ding et al. |
| 5,882,335 A | 3/1999 | Leone et al. |
| 5,888,591 A | 3/1999 | Gleason et al. |
| 5,891,108 A | 4/1999 | Leone et al. |
| 5,891,192 A | 4/1999 | Murayama et al. |
| 5,902,266 A | 5/1999 | Leone et al. |
| 5,922,021 A | 7/1999 | Jang |
| 5,928,247 A | 7/1999 | Barry et al. |
| 5,951,881 A | 9/1999 | Rogers et al. |
| 5,954,706 A | 9/1999 | Sahatjian |
| 5,962,136 A | 10/1999 | Dewez et al. |
| 5,968,091 A | 10/1999 | Pinchuk et al. |
| 5,968,092 A | 10/1999 | Buscemi et al. |
| 5,968,640 A | 10/1999 | Lubowitz et al. |
| 5,972,027 A | 10/1999 | Johnson |
| 5,977,204 A | 11/1999 | Boyan et al. |
| 5,980,564 A | 11/1999 | Stinson |
| 5,980,566 A | 11/1999 | Alt et al. |
| 6,013,591 A | 1/2000 | Ying et al. |
| 6,017,577 A | 1/2000 | Hostettler et al. |
| 6,022,812 A | 2/2000 | Smith et al. |
| 6,025,036 A | 2/2000 | McGill et al. |
| 6,034,295 A | 3/2000 | Rehberg et al. |
| 6,045,877 A | 4/2000 | Gleason et al. |
| 6,063,101 A | 5/2000 | Jacobsen et al. |
| 6,071,305 A | 6/2000 | Brown et al. |
| 6,074,135 A | 6/2000 | Tapphorn et al. |
| 6,096,070 A | 8/2000 | Ragheb et al. |
| 6,099,561 A | 8/2000 | Alt |
| 6,099,562 A | 8/2000 | Ding et al. |
| 6,106,473 A | 8/2000 | Violante et al. |
| 6,120,536 A | 9/2000 | Ding et al. |
| 6,120,660 A | 9/2000 | Chu et al. |
| 6,122,564 A | 9/2000 | Koch et al. |
| 6,139,573 A | 10/2000 | Sogard et al. |
| 6,139,913 A | 10/2000 | Van Steenkiste et al. |
| 6,153,252 A | 11/2000 | Hossainy et al. |
| 6,156,435 A | 12/2000 | Gleason et al. |
| 6,159,142 A | 12/2000 | Alt |
| 6,171,609 B1 | 1/2001 | Kunz |
| 6,174,329 B1 | 1/2001 | Callol et al. |
| 6,174,330 B1 | 1/2001 | Stinson |
| 6,180,184 B1 | 1/2001 | Gray et al. |
| 6,187,037 B1 | 2/2001 | Satz |
| 6,190,404 B1 | 2/2001 | Palmaz et al. |
| 6,193,761 B1 | 2/2001 | Treacy |
| 6,200,685 B1 | 3/2001 | Davidson |
| 6,203,536 B1 | 3/2001 | Berg et al. |
| 6,206,915 B1 | 3/2001 | Fagan et al. |
| 6,206,916 B1 | 3/2001 | Furst |
| 6,212,607 B1 | 4/2001 | Scheiner et al. |
| 6,214,042 B1 | 4/2001 | Jacobsen et al. |

| Patent | Date | Name |
|---|---|---|
| 6,217,607 B1 | 4/2001 | Alt |
| 6,231,600 B1 | 5/2001 | Zhong |
| 6,240,616 B1 | 6/2001 | Yan |
| 6,241,762 B1 | 6/2001 | Shanley |
| 6,245,104 B1 | 6/2001 | Alt |
| 6,249,952 B1 | 6/2001 | Ding |
| 6,251,136 B1 | 6/2001 | Guruwaiya et al. |
| 6,253,443 B1 | 7/2001 | Johnson |
| 6,254,632 B1 | 7/2001 | Wu et al. |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,280,411 B1 | 8/2001 | Lennox |
| 6,283,386 B1 | 9/2001 | Van Steenkiste et al. |
| 6,284,305 B1 | 9/2001 | Ding et al. |
| 6,287,331 B1 | 9/2001 | Heath |
| 6,287,332 B1 | 9/2001 | Bolz et al. |
| 6,287,628 B1 | 9/2001 | Hossainy et al. |
| 6,290,721 B1 | 9/2001 | Heath |
| 6,299,604 B1 | 10/2001 | Ragheb et al. |
| 6,306,144 B1 | 10/2001 | Sydney et al. |
| 6,315,708 B1 | 11/2001 | Salmon et al. |
| 6,315,794 B1 | 11/2001 | Richter |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,330 B1 | 12/2001 | Choy et al. |
| 6,335,029 B1 | 1/2002 | Kamath et al. |
| 6,337,076 B1 | 1/2002 | Studin |
| 6,342,507 B1 | 1/2002 | Naicker et al. |
| 6,348,960 B1 | 2/2002 | Etori et al. |
| 6,358,532 B2 | 3/2002 | Starling et al. |
| 6,358,556 B1 | 3/2002 | Ding et al. |
| 6,364,856 B1 | 4/2002 | Ding et al. |
| 6,367,412 B1 | 4/2002 | Ramaswamy et al. |
| 6,368,658 B1 | 4/2002 | Schwarz et al. |
| 6,379,383 B1 | 4/2002 | Palmaz et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,052 B2 | 5/2002 | Bulrge et al. |
| 6,395,325 B1 | 5/2002 | Hedge et al. |
| 6,395,326 B1 | 5/2002 | Castro et al. |
| 6,398,806 B1 | 6/2002 | You |
| 6,413,271 B1 | 7/2002 | Hafeli et al. |
| 6,416,820 B1 | 7/2002 | Yamada et al. |
| 6,419,692 B1 | 7/2002 | Yang et al. |
| 6,436,133 B1 | 8/2002 | Furst et al. |
| 6,440,503 B1 | 8/2002 | Merdan et al. |
| 6,458,153 B1 | 10/2002 | Bailey et al. |
| 6,465,052 B1 | 10/2002 | Wu |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,418 B2 | 11/2002 | Li et al. |
| 6,488,715 B1 | 12/2002 | Pope et al. |
| 6,491,666 B1 | 12/2002 | Santini, Jr. et al. |
| 6,491,720 B1 | 12/2002 | Vallana et al. |
| 6,503,921 B2 | 1/2003 | Naicker et al. |
| 6,504,292 B1 | 1/2003 | Choi et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,514,289 B1 | 2/2003 | Pope et al. |
| 6,517,888 B1 | 2/2003 | Weber |
| 6,524,274 B1 | 2/2003 | Rosenthal et al. |
| 6,527,801 B1 | 3/2003 | Dutta |
| 6,527,938 B2 | 3/2003 | Bales et al. |
| 6,530,951 B1 | 3/2003 | Bates et al. |
| 6,537,310 B1 | 3/2003 | Palmaz et al. |
| 6,544,582 B1 | 4/2003 | Yoe |
| 6,545,097 B2 | 4/2003 | Pinchuk et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,585,765 B1 | 7/2003 | Hossainy et al. |
| 6,599,558 B1 | 7/2003 | Al-Lamee et al. |
| 6,607,598 B2 | 8/2003 | Schwarz et al. |
| 6,613,083 B2 | 9/2003 | Alt |
| 6,613,432 B2 | 9/2003 | Zamora et al. |
| 6,616,765 B1 | 9/2003 | Castro et al. |
| 6,620,194 B2 | 9/2003 | Ding et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,999 B1 | 1/2004 | Wang et al. |
| 6,676,987 B2 | 1/2004 | Zhong et al. |
| 6,676,989 B2 | 1/2004 | Kirkpatrick et al. |
| 6,689,803 B2 | 2/2004 | Hunter |
| 6,695,865 B2 | 2/2004 | Boyle et al. |
| 6,699,281 B2 | 3/2004 | Vallana et al. |
| 6,699,282 B1 | 3/2004 | Sceusa |
| 6,709,379 B1 * | 3/2004 | Brandau et al. .................. 600/3 |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,723,120 B2 | 4/2004 | Yan |
| 6,725,901 B1 | 4/2004 | Kramer et al. |
| 6,726,712 B1 | 4/2004 | Raeder-Devens et al. |
| 6,730,120 B2 | 5/2004 | Berg et al. |
| 6,730,699 B2 | 5/2004 | Li et al. .................. 514/449 |
| 6,733,513 B2 | 5/2004 | Boyle et al. |
| 6,736,849 B2 | 5/2004 | Li et al. |
| 6,740,077 B1 | 5/2004 | Brandau et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,761,736 B1 | 7/2004 | Woo et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,780,424 B2 | 8/2004 | Claude |
| 6,780,491 B1 | 8/2004 | Cathey et al. |
| 6,783,543 B2 | 8/2004 | Jang |
| 6,790,228 B2 | 9/2004 | Hossainy et al. |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| 6,815,609 B1 | 11/2004 | Wang et al. |
| 6,820,676 B2 | 11/2004 | Palmaz et al. |
| 6,827,737 B2 | 12/2004 | Hill et al. |
| 6,830,598 B1 | 12/2004 | Sung |
| 6,833,004 B2 | 12/2004 | Ishii et al. |
| 6,846,323 B2 | 1/2005 | Yip et al. |
| 6,846,841 B2 | 1/2005 | Hunter et al. |
| 6,849,085 B2 | 2/2005 | Marton |
| 6,849,089 B2 | 2/2005 | Stoll |
| 6,852,122 B2 | 2/2005 | Rush |
| 6,861,088 B2 | 3/2005 | Weber et al. |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |

| | | | | | | |
|---|---|---|---|---|---|---|
| 6,884,429 B2 | 4/2005 | Koziak et al. | | 7,563,324 B1 | 7/2009 | Chen et al. |
| 6,896,697 B1 | 5/2005 | Yip et al. | | 7,575,593 B2 | 8/2009 | Rea et al. |
| 6,899,914 B2 | 5/2005 | Schaldach et al. | | 7,635,515 B1 | 12/2009 | Sherman |
| 6,904,658 B2 | 6/2005 | Hines | | 7,638,156 B1 | 12/2009 | Hossainy et al. |
| 6,908,622 B2 | 6/2005 | Barry et al. | | 7,691,461 B1 * | 4/2010 | Prabhu .................. 428/36.9 |
| 6,908,624 B2 | 6/2005 | Hossainy et al. | | 7,713,297 B2 | 5/2010 | Alt |
| 6,913,617 B1 | 7/2005 | Reiss | | 7,727,275 B2 | 6/2010 | Betts et al. |
| 6,915,796 B2 | 7/2005 | Sung | | 7,749,264 B2 | 7/2010 | Gregorich et al. |
| 6,918,927 B2 | 7/2005 | Bates et al. | | 7,758,636 B2 | 7/2010 | Shanley et al. |
| 6,923,829 B2 | 8/2005 | Boyle et al. | | 7,771,773 B2 | 8/2010 | Namavar |
| 6,924,004 B2 | 8/2005 | Rao et al. | | 2001/0001834 A1 | 5/2001 | Palmaz et al. |
| 6,932,930 B2 | 8/2005 | DeSimone et al. | | 2001/0002000 A1 | 5/2001 | Kumar et al. |
| 6,936,066 B2 | 8/2005 | Palmaz et al. | | 2001/0002435 A1 | 5/2001 | Berg et al. |
| 6,939,320 B2 | 9/2005 | Lennox | | 2001/0013166 A1 | 8/2001 | Yan |
| 6,951,053 B2 | 10/2005 | Padilla et al. | | 2001/0014717 A1 | 8/2001 | Hossainy et al. |
| 6,953,560 B1 | 10/2005 | Castro et al. | | 2001/0014821 A1 | 8/2001 | Juman et al. |
| 6,955,661 B1 | 10/2005 | Herweck et al. | | 2001/0027299 A1 | 10/2001 | Yang et al. |
| 6,955,685 B2 | 10/2005 | Escamilla et al. | | 2001/0029660 A1 | 10/2001 | Johnson |
| 6,962,822 B2 | 11/2005 | Hart et al. | | 2001/0032011 A1 | 10/2001 | Stanford |
| 6,971,813 B2 | 12/2005 | Shekalim et al. | | 2001/0032013 A1 | 10/2001 | Marton |
| 6,973,718 B2 | 12/2005 | Sheppard, Jr. et al. | | 2001/0044651 A1 | 11/2001 | Steinke et al. |
| 6,979,346 B1 | 12/2005 | Hossainy et al. | | 2002/0000175 A1 | 1/2002 | Hintermaier et al. |
| 6,979,348 B2 | 12/2005 | Sundar | | 2002/0004060 A1 | 1/2002 | Heublein et al. .......... 424/422 |
| 6,984,404 B1 | 1/2006 | Talton et al. | | 2002/0007102 A1 | 1/2002 | Salmon et al. |
| 7,001,421 B2 | 2/2006 | Cheng et al. | | 2002/0007209 A1 | 1/2002 | Schearder et al. |
| 7,011,680 B2 | 3/2006 | Alt | | 2002/0009604 A1 | 1/2002 | Zamora et al. |
| 7,014,654 B2 | 3/2006 | Welsh et al. | | 2002/0010505 A1 | 1/2002 | Richter |
| 7,018,408 B2 | 3/2006 | Bailey et al. | | 2002/0016623 A1 | 2/2002 | Kula et al. |
| 7,041,130 B2 | 5/2006 | Santini, Jr. et al. | | 2002/0016624 A1 | 2/2002 | Patterson et al. |
| 7,048,939 B2 | 5/2006 | Elkins et al. | | 2002/0028827 A1 | 3/2002 | Naicker et al. |
| 7,052,488 B2 | 5/2006 | Uhland | | 2002/0032477 A1 | 3/2002 | Helmus et al. |
| 7,056,338 B2 | 6/2006 | Shanley et al. | | 2002/0038146 A1 | 3/2002 | Harry |
| 7,056,339 B2 | 6/2006 | Elkins et al. | | 2002/0042039 A1 | 4/2002 | Kim et al. |
| 7,056,591 B1 | 6/2006 | Pacetti et al. | | 2002/0051730 A1 | 5/2002 | Bodnar et al. |
| 7,060,051 B2 | 6/2006 | Palasis | | 2002/0051846 A1 | 5/2002 | Kirkpatrick et al. |
| 7,063,748 B2 | 6/2006 | Talton | | 2002/0052288 A1 | 5/2002 | Krell et al. |
| 7,066,234 B2 | 6/2006 | Sawitowski | | 2002/0065553 A1 | 5/2002 | Weber |
| 7,077,859 B2 | 7/2006 | Sirhan et al. | | 2002/0072734 A1 | 6/2002 | Liedtke et al. |
| 7,078,108 B2 | 7/2006 | Zhang et al. | | 2002/0077520 A1 | 6/2002 | Segal et al. |
| 7,083,642 B2 | 8/2006 | Sirhan et al. | | 2002/0077693 A1 | 6/2002 | Barclay et al. |
| 7,087,661 B1 | 8/2006 | Alberte et al. | | 2002/0087123 A1 | 7/2002 | Hossainy et al. |
| 7,099,091 B2 | 8/2006 | Taniguchi et al. | | 2002/0091375 A1 | 7/2002 | Sahatjian et al. |
| 7,101,391 B2 | 9/2006 | Scheuermann et al. | | 2002/0095871 A1 | 7/2002 | McArdle et al. |
| 7,101,394 B2 * | 9/2006 | Hamm et al. .............. 623/1.42 | | 2002/0098278 A1 | 7/2002 | Bates et al. |
| 7,105,018 B1 | 9/2006 | Yip et al. | | 2002/0099359 A1 | 7/2002 | Santini, Jr. et al. |
| 7,105,199 B2 | 9/2006 | Blinn et al. | | 2002/0099438 A1 | 7/2002 | Furst |
| 7,144,840 B2 | 12/2006 | Yeung et al. | | 2002/0103527 A1 | 8/2002 | Kocur et al. |
| 7,160,592 B2 | 1/2007 | Rypacek et al. | | 2002/0103528 A1 | 8/2002 | Schaldach et al. |
| 7,163,715 B1 | 1/2007 | Kramer | | 2002/0104599 A1 | 8/2002 | Tillotson et al. |
| 7,169,177 B2 | 1/2007 | Obara | | 2002/0121497 A1 | 9/2002 | Tomonto |
| 7,169,178 B1 | 1/2007 | Santos et al. | | 2002/0123801 A1 | 9/2002 | Pacetti et al. |
| 7,195,640 B2 | 3/2007 | Falotico et al. | | 2002/0133222 A1 | 9/2002 | Das |
| 7,195,641 B2 | 3/2007 | Palmaz et al. | | 2002/0133225 A1 * | 9/2002 | Gordon ..................... 623/1.42 |
| 7,198,675 B2 | 4/2007 | Fox et al. | | 2002/0138100 A1 | 9/2002 | Stoll et al. |
| 7,208,011 B2 | 4/2007 | Shanley et al. | | 2002/0138136 A1 | 9/2002 | Chandresekaran et al. |
| 7,208,172 B2 | 4/2007 | Birdsall et al. | | 2002/0140137 A1 | 10/2002 | Sapieszko et al. |
| 7,229,471 B2 | 6/2007 | Gale et al. | | 2002/0142579 A1 | 10/2002 | Vincent et al. |
| 7,235,096 B1 | 6/2007 | Van Tassel et al. | | 2002/0144757 A1 | 10/2002 | Craig et al. |
| 7,235,098 B2 | 6/2007 | Palmaz | | 2002/0155212 A1 | 10/2002 | Hossainy |
| 7,238,199 B2 | 7/2007 | Feldman et al. | | 2002/0165265 A1 | 11/2002 | Hunter et al. |
| 7,244,272 B2 | 7/2007 | Dubson et al. | | 2002/0165600 A1 | 11/2002 | Banas et al. |
| 7,247,166 B2 | 7/2007 | Pienknagura | | 2002/0165607 A1 | 11/2002 | Alt |
| 7,247,338 B2 | 7/2007 | Pui et al. | | 2002/0167118 A1 | 11/2002 | Billiet et al. |
| 7,261,735 B2 | 8/2007 | Llanos et al. | | 2002/0168466 A1 | 11/2002 | Tapphorn et al. |
| 7,261,752 B2 | 8/2007 | Sung | | 2002/0169493 A1 | 11/2002 | Widenhouse et al. |
| 7,273,493 B2 | 9/2007 | Ledergerber | | 2002/0178570 A1 | 12/2002 | Sogard et al. |
| 7,294,409 B2 | 11/2007 | Lye et al. | | 2002/0182241 A1 | 12/2002 | Borenstein et al. |
| 7,311,727 B2 | 12/2007 | Mazumder et al. | | 2002/0183581 A1 | 12/2002 | Yoe et al. |
| 7,344,563 B2 | 3/2008 | Vallana et al. | | 2002/0183682 A1 | 12/2002 | Darvish et al. |
| 7,368,065 B2 * | 5/2008 | Yang et al. ................ 216/83 | | 2002/0187260 A1 | 12/2002 | Sheppard, Jr. et al. |
| 7,393,589 B2 | 7/2008 | Aharonov et al. | | 2002/0193336 A1 | 12/2002 | Elkins et al. |
| 7,396,538 B2 | 7/2008 | Granada et al. | | 2002/0193869 A1 | 12/2002 | Dang |
| 7,402,173 B2 | 7/2008 | Scheuermann et al. | | 2002/0197178 A1 | 12/2002 | Yan |
| 7,416,558 B2 | 8/2008 | Yip et al. | | 2002/0198601 A1 | 12/2002 | Bales et al. |
| 7,435,256 B2 | 10/2008 | Stenzel | | 2003/0003160 A1 | 1/2003 | Pugh et al. |
| 7,482,034 B2 | 1/2009 | Boulais | | 2003/0003220 A1 | 1/2003 | Zhong et al. |
| 7,494,950 B2 | 2/2009 | Armitage et al. | | 2003/0004563 A1 | 1/2003 | Jackson et al. |
| 7,497,876 B2 * | 3/2009 | Tuke et al. ................ 623/23.5 | | 2003/0004564 A1 | 1/2003 | Elkins et al. |
| 7,547,445 B2 | 6/2009 | Chudzik et al. | | 2003/0006250 A1 | 1/2003 | Tapphorn et al. |

| | | | | | |
|---|---|---|---|---|---|
| 2003/0009214 A1 | 1/2003 | Shanley | 2004/0047980 A1 | 3/2004 | Pacetti et al. |
| 2003/0009233 A1 | 1/2003 | Blinn et al. | 2004/0058858 A1 | 3/2004 | Hu |
| 2003/0018380 A1 | 1/2003 | Craig et al. | 2004/0059290 A1 | 3/2004 | Palasis |
| 2003/0018381 A1 | 1/2003 | Whitcher et al. | 2004/0059407 A1 | 3/2004 | Escamilla et al. |
| 2003/0021820 A1 | 1/2003 | Ahola et al. | 2004/0059409 A1 | 3/2004 | Stenzel |
| 2003/0023300 A1 | 1/2003 | Bailey et al. | 2004/0067301 A1 | 4/2004 | Ding |
| 2003/0028242 A1 | 2/2003 | Vallana et al. | 2004/0071861 A1 | 4/2004 | Mandrusov et al. |
| 2003/0028243 A1 | 2/2003 | Bates et al. | 2004/0073284 A1 | 4/2004 | Bates et al. |
| 2003/0032892 A1 | 2/2003 | Erlach et al. | 2004/0073298 A1 | 4/2004 | Hossainy |
| 2003/0033007 A1 | 2/2003 | Sirhan et al. | 2004/0078071 A1 | 4/2004 | Escamilla et al. |
| 2003/0044446 A1 | 3/2003 | Moro et al. | 2004/0086674 A1 | 5/2004 | Holman |
| 2003/0047028 A1 | 3/2003 | Kunitake et al. | 2004/0088038 A1 | 5/2004 | Dehnad et al. |
| 2003/0047505 A1 | 3/2003 | Grimes et al. | 2004/0088041 A1 | 5/2004 | Stanford |
| 2003/0050687 A1 | 3/2003 | Schwade et al. | 2004/0092653 A1 | 5/2004 | Ruberti et al. |
| 2003/0059640 A1 | 3/2003 | Marton et al. | 2004/0093071 A1 | 5/2004 | Jang |
| 2003/0060871 A1 | 3/2003 | Hill et al. | 2004/0093076 A1 | 5/2004 | White et al. |
| 2003/0060873 A1 | 3/2003 | Gertner et al. | 2004/0098089 A1 | 5/2004 | Weber |
| 2003/0060877 A1 | 3/2003 | Falotico et al. | 2004/0098119 A1 | 5/2004 | Wang |
| 2003/0064095 A1 | 4/2003 | Martin et al. | 2004/0102758 A1 | 5/2004 | Davila et al. |
| 2003/0069631 A1 | 4/2003 | Stoll | 2004/0106984 A1 | 6/2004 | Stinson |
| 2003/0074053 A1 | 4/2003 | Palmaz et al. | 2004/0106985 A1 | 6/2004 | Jang |
| 2003/0074075 A1 | 4/2003 | Thomas et al. | 2004/0106987 A1 | 6/2004 | Palasis et al. |
| 2003/0077200 A1 | 4/2003 | Craig et al. | 2004/0106994 A1 | 6/2004 | De Maeztus Martinez et al. |
| 2003/0083614 A1 | 5/2003 | Eisert | 2004/0111150 A1 | 6/2004 | Berg et al. |
| 2003/0083646 A1 | 5/2003 | Sirhan et al. | 2004/0116999 A1 | 6/2004 | Ledergerber |
| 2003/0083731 A1 | 5/2003 | Kramer et al. | 2004/0117005 A1 | 6/2004 | Gadde et al. |
| 2003/0087024 A1 | 5/2003 | Flanagan | 2004/0117008 A1 | 6/2004 | Wnendt et al. |
| 2003/0088307 A1 | 5/2003 | Shulze et al. | 2004/0122504 A1 | 6/2004 | Hogendijk |
| 2003/0088312 A1 | 5/2003 | Kopia et al. | 2004/0126566 A1 | 7/2004 | Axen et al. |
| 2003/0100865 A1 | 5/2003 | Santini, Jr. et al. | 2004/0133270 A1 | 7/2004 | Grandt |
| 2003/0104028 A1 | 6/2003 | Hossainy et al. | 2004/0134886 A1 | 7/2004 | Wagner et al. |
| 2003/0105511 A1 | 6/2003 | Welsh et al. | 2004/0142014 A1 | 7/2004 | Litvack et al. |
| 2003/0108659 A1 | 6/2003 | Bales et al. | 2004/0143317 A1 | 7/2004 | Stinson et al. |
| 2003/0114917 A1 | 6/2003 | Holloway et al. | 2004/0143321 A1 | 7/2004 | Litvack et al. |
| 2003/0114921 A1 | 6/2003 | Yoon | 2004/0148010 A1 | 7/2004 | Rush |
| 2003/0118649 A1 | 6/2003 | Gao et al. | 2004/0148015 A1 | 7/2004 | Lye et al. |
| 2003/0125803 A1 | 7/2003 | Vallana et al. | 2004/0158308 A1 | 8/2004 | Hogendijk et al. |
| 2003/0130206 A1 | 7/2003 | Koziak et al. | 2004/0167572 A1 | 8/2004 | Roth et al. |
| 2003/0130718 A1 | 7/2003 | Palmas et al. | 2004/0167612 A1 | 8/2004 | Grignani et al. |
| 2003/0138645 A1 | 7/2003 | Gleason et al. | 2004/0171978 A1 | 9/2004 | Shalaby |
| 2003/0139799 A1 | 7/2003 | Ley et al. | 2004/0172124 A1 | 9/2004 | Vallana et al. |
| 2003/0144728 A1 | 7/2003 | Scheuermann et al. | 2004/0178523 A1 | 9/2004 | Kim et al. |
| 2003/0150380 A1 | 8/2003 | Yoe | 2004/0181252 A1 | 9/2004 | Boyle et al. |
| 2003/0153901 A1 | 8/2003 | Herweck et al. | 2004/0181275 A1 | 9/2004 | Noble et al. |
| 2003/0153971 A1 | 8/2003 | Chandrasekaran | 2004/0181276 A1 | 9/2004 | Brown et al. |
| 2003/0158598 A1 | 8/2003 | Ashton et al. | 2004/0185168 A1 | 9/2004 | Weber et al. |
| 2003/0167878 A1 | 9/2003 | Al-Salim et al. | 2004/0191293 A1 | 9/2004 | Claude |
| 2003/0170605 A1 | 9/2003 | Long et al. | 2004/0191404 A1 | 9/2004 | Hossainy et al. |
| 2003/0181975 A1 | 9/2003 | Ishii et al. | 2004/0202692 A1 | 10/2004 | Shanley et al. |
| 2003/0185895 A1 | 10/2003 | Lanphere et al. | 2004/0204750 A1 | 10/2004 | Dinh |
| 2003/0185964 A1 | 10/2003 | Weber et al. | 2004/0211362 A1 | 10/2004 | Castro et al. |
| 2003/0190406 A1 | 10/2003 | Hossainy et al. | 2004/0215169 A1 | 10/2004 | Li |
| 2003/0195613 A1 | 10/2003 | Curcio et al. | 2004/0215313 A1 | 10/2004 | Cheng |
| 2003/0203991 A1 | 10/2003 | Schottman et al. | 2004/0219214 A1 | 11/2004 | Gravett et al. |
| 2003/0204168 A1 | 10/2003 | Bosma et al. | 2004/0220510 A1 | 11/2004 | Koullick et al. |
| 2003/0208256 A1 | 11/2003 | DiMatteo et al. | 2004/0220662 A1 | 11/2004 | Dang et al. |
| 2003/0211135 A1 | 11/2003 | Greenhalgh et al. | 2004/0224001 A1 | 11/2004 | Pacetti et al. |
| 2003/0216803 A1 | 11/2003 | Ledergerber | 2004/0225346 A1 | 11/2004 | Mazumder et al. |
| 2003/0219562 A1 | 11/2003 | Rypacek et al. | 2004/0225347 A1 | 11/2004 | Lang |
| 2003/0225450 A1 | 12/2003 | Shulze et al. | 2004/0228905 A1 | 11/2004 | Greenspan et al. |
| 2003/0236323 A1 | 12/2003 | Ratner et al. .......... 524/27 | 2004/0230176 A1 | 11/2004 | Shanahan et al. |
| 2003/0236514 A1 | 12/2003 | Schwarz | 2004/0230290 A1 | 11/2004 | Weber et al. |
| 2004/0000540 A1 | 1/2004 | Soboyejo et al. | 2004/0230293 A1 | 11/2004 | Yip et al. |
| 2004/0002755 A1 | 1/2004 | Fischell et al. | 2004/0234737 A1 | 11/2004 | Pacetti |
| 2004/0006382 A1 | 1/2004 | Sohier | 2004/0234748 A1 | 11/2004 | Stenzel |
| 2004/0013873 A1 | 1/2004 | Wendorff et al. | 2004/0236399 A1 | 11/2004 | Sundar |
| 2004/0016651 A1 | 1/2004 | Windler | 2004/0236415 A1 | 11/2004 | Thomas |
| 2004/0018296 A1 | 1/2004 | Castro et al. | 2004/0236416 A1 | 11/2004 | Falotico |
| 2004/0019376 A1 | 1/2004 | Alt | 2004/0237282 A1 | 12/2004 | Hines |
| 2004/0022824 A1 | 2/2004 | Li et al. | 2004/0242106 A1 | 12/2004 | Rabasco et al. |
| 2004/0026811 A1 | 2/2004 | Murphy et al. | 2004/0243217 A1 | 12/2004 | Andersen et al. |
| 2004/0028875 A1 | 2/2004 | Van Rijn et al. | 2004/0243241 A1 | 12/2004 | Istephanous |
| 2004/0029303 A1 | 2/2004 | Hart et al. | 2004/0247671 A1 | 12/2004 | Prescott et al. |
| 2004/0029706 A1 | 2/2004 | Barrera et al. ............ 501/99 | 2004/0249444 A1 | 12/2004 | Reiss |
| 2004/0030218 A1 | 2/2004 | Kocur et al. | 2004/0249449 A1 | 12/2004 | Shanley et al. |
| 2004/0030377 A1 | 2/2004 | Dubson et al. | 2004/0254635 A1 | 12/2004 | Shanley et al. |
| 2004/0039438 A1 | 2/2004 | Alt | 2004/0261702 A1 | 12/2004 | Grabowy et al. |
| 2004/0039441 A1 | 2/2004 | Rowland et al. | 2005/0002865 A1 | 1/2005 | Klaveness et al. ........ 424/9.52 |
| 2004/0044397 A1 | 3/2004 | Stinson | 2005/0004663 A1 | 1/2005 | Llanos et al. |

| | | | | | |
|---|---|---|---|---|---|
| 2005/0010275 A1 | 1/2005 | Sahatjian et al. | 2005/0233965 A1 | 10/2005 | Schwartz et al. |
| 2005/0015142 A1 | 1/2005 | Austin et al. | 2005/0244459 A1 | 11/2005 | DeWitt et al. |
| 2005/0019265 A1 | 1/2005 | Hammer et al. | 2005/0251245 A1 | 11/2005 | Sieradzki et al. |
| 2005/0019371 A1 | 1/2005 | Anderson et al. | 2005/0251249 A1 | 11/2005 | Sahatjian et al. |
| 2005/0020614 A1 | 1/2005 | Prescott et al. | 2005/0255707 A1 | 11/2005 | Hart et al. |
| 2005/0021127 A1 | 1/2005 | Kawula | 2005/0261760 A1 | 11/2005 | Weber |
| 2005/0021128 A1 | 1/2005 | Nakahama et al. | 2005/0266039 A1 | 12/2005 | Weber |
| 2005/0027350 A1 | 2/2005 | Momma et al. | 2005/0266040 A1 | 12/2005 | Gerberding |
| 2005/0033411 A1 | 2/2005 | Wu et al. | 2005/0267561 A1 | 12/2005 | Jones et al. |
| 2005/0033412 A1 | 2/2005 | Wu et al. | 2005/0271703 A1 | 12/2005 | Anderson et al. |
| 2005/0033417 A1 | 2/2005 | Borges et al. | 2005/0271706 A1 | 12/2005 | Anderson et al. |
| 2005/0037047 A1 | 2/2005 | Song | 2005/0276837 A1 | 12/2005 | Anderson et al. |
| 2005/0038498 A1 | 2/2005 | Dubrow et al. | 2005/0278016 A1 | 12/2005 | Welsh et al. |
| 2005/0042288 A1 | 2/2005 | Koblish et al. | 2005/0278021 A1 | 12/2005 | Bates et al. |
| 2005/0055080 A1 | 3/2005 | Istephanous et al. | 2005/0281863 A1 | 12/2005 | Anderson et al. |
| 2005/0055085 A1 | 3/2005 | Rivron et al. | 2005/0285073 A1 | 12/2005 | Singh et al. ............... 252/62.54 |
| 2005/0060020 A1 | 3/2005 | Jenson | 2005/0287188 A1 | 12/2005 | Anderson et al. |
| 2005/0060021 A1* | 3/2005 | O'Brien et al. ............... 623/1.15 | 2006/0013850 A1 | 1/2006 | Domb |
| 2005/0069630 A1 | 3/2005 | Fox et al. | 2006/0015175 A1 | 1/2006 | Palmaz et al. |
| 2005/0070989 A1 | 3/2005 | Lye et al. | 2006/0015361 A1 | 1/2006 | Sattler et al. |
| 2005/0070990 A1 | 3/2005 | Stinson | 2006/0020742 A1 | 1/2006 | Au et al. |
| 2005/0070996 A1 | 3/2005 | Dinh et al. | 2006/0003884 A1 | 2/2006 | Stenzel |
| 2005/0072544 A1 | 4/2005 | Palmaz et al. | 2006/0025848 A1 | 2/2006 | Weber et al. |
| 2005/0074479 A1 | 4/2005 | Weber et al. | 2006/0035026 A1 | 2/2006 | Atanassoska et al. |
| 2005/0074545 A1 | 4/2005 | Thomas | 2006/0038027 A1 | 2/2006 | O'Connor et al. |
| 2005/0077305 A1 | 4/2005 | Guevara | 2006/0051397 A1 | 3/2006 | Maier et al. |
| 2005/0079199 A1 | 4/2005 | Heruth et al. | 2006/0052744 A1 | 3/2006 | Weber |
| 2005/0079201 A1 | 4/2005 | Rathenow et al. | 2006/0052863 A1 | 3/2006 | Harder et al. |
| 2005/0079356 A1 | 4/2005 | Rathenow et al. | 2006/0052864 A1 | 3/2006 | Harder et al. |
| 2005/0087520 A1 | 4/2005 | Wang et al. | 2006/0062820 A1 | 3/2006 | Gertner et al. |
| 2005/0092615 A1 | 5/2005 | Birdsall et al. | 2006/0069427 A1 | 3/2006 | Savage et al. |
| 2005/0096731 A1 | 5/2005 | Looi et al. | 2006/0075044 A1 | 4/2006 | Fox et al. |
| 2005/0100577 A1 | 5/2005 | Parker et al. | 2006/0075092 A1 | 4/2006 | Kidokoro |
| 2005/0100609 A1 | 5/2005 | Claude | 2006/0079863 A1 | 4/2006 | Burgmeier et al. |
| 2005/0102025 A1 | 5/2005 | Laroche et al. | 2006/0085062 A1 | 4/2006 | Lee et al. |
| 2005/0106212 A1 | 5/2005 | Gertner et al. | 2006/0085065 A1 | 4/2006 | Krause et al. |
| 2005/0107870 A1 | 5/2005 | Wang et al. | 2006/0088561 A1 | 4/2006 | Eini et al. |
| 2005/0110214 A1 | 5/2005 | Shank et al. | 2006/0088566 A1 | 4/2006 | Parsonage et al. |
| 2005/0113936 A1 | 5/2005 | Brustad et al. | 2006/0088567 A1 | 4/2006 | Warner et al. |
| 2005/0119723 A1 | 6/2005 | Peacock | 2006/0088666 A1 | 4/2006 | Kobrin et al. |
| 2005/0129727 A1 | 6/2005 | Weber et al. | 2006/0093643 A1 | 5/2006 | Stenzel |
| 2005/0131509 A1 | 6/2005 | Atanassoska et al. | 2006/0093646 A1 | 5/2006 | Cima et al. |
| 2005/0131521 A1 | 6/2005 | Marton | 2006/0095123 A1 | 5/2006 | Flanagan |
| 2005/0131522 A1 | 6/2005 | Stinson et al. | 2006/0100696 A1 | 5/2006 | Atanassoska et al. |
| 2005/0136090 A1 | 6/2005 | Falotico et al. | 2006/0115512 A1 | 6/2006 | Peacock et al. |
| 2005/0137677 A1 | 6/2005 | Rush | 2006/0121080 A1 | 6/2006 | Lye et al. |
| 2005/0137679 A1 | 6/2005 | Changelian et al. | 2006/0122694 A1 | 6/2006 | Stinson et al. |
| 2005/0137684 A1 | 6/2005 | Changelian et al. | 2006/0125144 A1 | 6/2006 | Weber et al. |
| 2005/0149102 A1 | 7/2005 | Radisch et al. | 2006/0127442 A1 | 6/2006 | Helmus |
| 2005/0149170 A1 | 7/2005 | Tassel et al. | 2006/0127443 A1 | 6/2006 | Helmus |
| 2005/0159804 A1 | 7/2005 | Lad et al. | 2006/0129215 A1 | 6/2006 | Helmus et al. ............... 607/115 |
| 2005/0159805 A1 | 7/2005 | Weber et al. | 2006/0129225 A1 | 6/2006 | Kopia et al. |
| 2005/0160600 A1 | 7/2005 | Bien et al. | 2006/0136048 A1 | 6/2006 | Pacetti et al. |
| 2005/0163954 A1 | 7/2005 | Shaw | 2006/0141156 A1 | 6/2006 | Viel et al. |
| 2005/0165467 A1 | 7/2005 | Hunter et al. | 2006/0142853 A1 | 6/2006 | Wang et al. |
| 2005/0165468 A1 | 7/2005 | Marton | 2006/0153729 A1 | 7/2006 | Stinson et al. |
| 2005/0165476 A1 | 7/2005 | Furst et al. | 2006/0155361 A1 | 7/2006 | Schomig et al. |
| 2005/0171595 A1 | 8/2005 | Feldman et al. | 2006/0167543 A1 | 7/2006 | Bailey et al. |
| 2005/0180919 A1 | 8/2005 | Tedeschi | 2006/0171985 A1 | 8/2006 | Richard et al. |
| 2005/0182478 A1 | 8/2005 | Holman et al. | 2006/0178727 A1 | 8/2006 | Richter |
| 2005/0186250 A1 | 8/2005 | Gertner et al. | 2006/0184235 A1 | 8/2006 | Rivron et al. |
| 2005/0187608 A1 | 8/2005 | O'Hara | 2006/0193886 A1 | 8/2006 | Owens et al. |
| 2005/0192657 A1 | 9/2005 | Colen et al. | 2006/0193887 A1 | 8/2006 | Owens et al. |
| 2005/0192664 A1 | 9/2005 | Eisert | 2006/0193888 A1 | 8/2006 | Lye et al. |
| 2005/0196424 A1 | 9/2005 | Chappa | 2006/0193889 A1 | 8/2006 | Spradlin et al. |
| 2005/0196518 A1 | 9/2005 | Stenzel | 2006/0193890 A1 | 8/2006 | Owens et al. |
| 2005/0197687 A1 | 9/2005 | Molaei et al. | 2006/0199876 A1 | 9/2006 | Troczynski et al. |
| 2005/0203606 A1 | 9/2005 | Vancamp | 2006/0200229 A1 | 9/2006 | Burgermeister et al. |
| 2005/0208098 A1 | 9/2005 | Castro et al. | 2006/0200231 A1 | 9/2006 | O'Brien et al. |
| 2005/0208100 A1* | 9/2005 | Weber et al. ............... 424/426 | 2006/0210595 A1 | 9/2006 | Singhvi et al. |
| 2005/0209681 A1 | 9/2005 | Curcio et al. | 2006/0212109 A1 | 9/2006 | Sirhan et al. |
| 2005/0211680 A1 | 9/2005 | Li et al. | 2006/0222679 A1 | 10/2006 | Shanley et al. |
| 2005/0214951 A1 | 9/2005 | Nahm et al. | 2006/0222844 A1 | 10/2006 | Stinson |
| 2005/0216074 A1 | 9/2005 | Sahatjian et al. | 2006/0224234 A1 | 10/2006 | Jayaraman |
| 2005/0220853 A1 | 10/2005 | Dao et al. | 2006/0229711 A1 | 10/2006 | Yan et al. |
| 2005/0221072 A1 | 10/2005 | Dubrow et al. | 2006/0229713 A1 | 10/2006 | Shanley et al. |
| 2005/0228477 A1 | 10/2005 | Grainger et al. | 2006/0229715 A1* | 10/2006 | Istephanous et al. ........ 623/1.46 |
| 2005/0228491 A1* | 10/2005 | Snyder et al. ............... 623/1.46 | 2006/0230476 A1 | 10/2006 | Atanasoska et al. |
| 2005/0232968 A1 | 10/2005 | Palmaz et al. | 2006/0233941 A1 | 10/2006 | Olson |

| | | | | | | |
|---|---|---|---|---|---|---|
| 2006/0251701 A1 | 11/2006 | Lynn et al. | | 2008/0071351 A1 | 3/2008 | Flanagan et al. |
| 2006/0263512 A1 | 11/2006 | Glocker | | 2008/0071352 A1 | 3/2008 | Weber et al. |
| 2006/0263515 A1 | 11/2006 | Rieck et al. | | 2008/0071353 A1 | 3/2008 | Weber et al. |
| 2006/0264138 A1 | 11/2006 | Sowinski et al. | | 2008/0071355 A1 | 3/2008 | Weber et al. |
| 2006/0271169 A1 | 11/2006 | Lye et al. | | 2008/0071358 A1 | 3/2008 | Weber et al. |
| 2006/0275554 A1 | 12/2006 | Zhao et al. | | 2008/0086199 A1 | 4/2008 | Dave et al. |
| 2006/0276877 A1 | 12/2006 | Owens et al. | | 2008/0086201 A1 | 4/2008 | Weber et al. |
| 2006/0276878 A1 | 12/2006 | Owens et al. | | 2008/0097577 A1 | 4/2008 | Atanasoska et al. |
| 2006/0276879 A1 | 12/2006 | Lye et al. | | 2008/0107890 A1 | 5/2008 | Bureau et al. |
| 2006/0276884 A1 | 12/2006 | Lye et al. | | 2008/0124373 A1 | 5/2008 | Xiao et al. |
| 2006/0276885 A1 | 12/2006 | Lye et al. | | 2008/0140186 A1 | 6/2008 | Grignani et al. |
| 2006/0276910 A1 | 12/2006 | Weber | | 2008/0145400 A1 | 6/2008 | Weber et al. |
| 2006/0280770 A1 | 12/2006 | Hossainy et al. | | 2008/0147177 A1* | 6/2008 | Scheuermann et al. ..... 623/1.42 |
| 2006/0292388 A1 | 12/2006 | Palumbo et al. | | 2008/0152929 A1 | 6/2008 | Zhao |
| 2007/0003589 A1 | 1/2007 | Astafieva et al. | | 2008/0160259 A1 | 7/2008 | Nielson et al. |
| 2007/0003817 A1 | 1/2007 | Umeda et al. | | 2008/0171929 A1 | 7/2008 | Katims |
| 2007/0032858 A1 | 2/2007 | Santos et al. | | 2008/0188836 A1 | 8/2008 | Weber et al. |
| 2007/0032864 A1 | 2/2007 | Furst et al. | | 2008/0241218 A1 | 10/2008 | McMorrow et al. |
| 2007/0036905 A1 | 2/2007 | Kramer | | 2008/0243231 A1* | 10/2008 | Flanagan et al. ............. 623/1.16 |
| 2007/0038176 A1 | 2/2007 | Weber et al. | | 2008/0243240 A1 | 10/2008 | Doty et al. |
| 2007/0038289 A1 | 2/2007 | Nishide et al. | | 2008/0249600 A1 | 10/2008 | Atanasoska et al. |
| 2007/0048452 A1 | 3/2007 | Feng et al. | | 2008/0249615 A1 | 10/2008 | Weber |
| 2007/0052497 A1 | 3/2007 | Tada | | 2008/0255508 A1 | 10/2008 | Wang |
| 2007/0055349 A1 | 3/2007 | Santos et al. | | 2008/0255657 A1* | 10/2008 | Gregorich et al. ........... 623/1.16 |
| 2007/0055354 A1 | 3/2007 | Santos et al. | | 2008/0262607 A1 | 10/2008 | Fricke |
| 2007/0059435 A1 | 3/2007 | Santos et al. | | 2008/0275543 A1* | 11/2008 | Lenz et al. .................... 623/1.42 |
| 2007/0065418 A1 | 3/2007 | Vallana et al. | | 2008/0288048 A1 | 11/2008 | Rolando et al. |
| 2007/0071789 A1 | 3/2007 | Pantelidis et al. | | 2008/0290467 A1 | 11/2008 | Shue et al. |
| 2007/0072978 A1 | 3/2007 | Zoromski et al. | | 2008/0294236 A1 | 11/2008 | Anand et al. |
| 2007/0073385 A1 | 3/2007 | Schaeffer et al. | | 2008/0294246 A1 | 11/2008 | Scheuermann et al. |
| 2007/0073390 A1 | 3/2007 | Lee | | 2008/0306584 A1 | 12/2008 | Kramer-Brown |
| 2007/0106347 A1 | 5/2007 | Lin | | 2009/0012603 A1* | 1/2009 | Xu et al. ....................... 623/1.42 |
| 2007/0110888 A1 | 5/2007 | Radhakrishnan et al. | | 2009/0018639 A1 | 1/2009 | Kuehling |
| 2007/0112421 A1* | 5/2007 | O'Brien ........................ 623/1.46 | | 2009/0018642 A1 | 1/2009 | Benco |
| 2007/0123973 A1 | 5/2007 | Roth et al. | | 2009/0018644 A1 | 1/2009 | Weber et al. |
| 2007/0128245 A1 | 6/2007 | Rosenberg et al. | | 2009/0018647 A1 | 1/2009 | Benco et al. |
| 2007/0129789 A1 | 6/2007 | Cottone et al. | | 2009/0028785 A1 | 1/2009 | Clarke |
| 2007/0134288 A1 | 6/2007 | Parsonage et al. | | 2009/0030504 A1 | 1/2009 | Weber et al. |
| 2007/0135908 A1 | 6/2007 | Zhao | | 2009/0076588 A1 | 3/2009 | Weber |
| 2007/0148251 A1 | 6/2007 | Hossainy et al. | | 2009/0076595 A1* | 3/2009 | Lindquist et al. ............ 623/1.43 |
| 2007/0151093 A1* | 7/2007 | Curcio et al. ..................... 29/557 | | 2009/0081450 A1 | 3/2009 | Ascher et al. |
| 2007/0154513 A1 | 7/2007 | Atanasoska et al. .......... 424/423 | | 2009/0112310 A1* | 4/2009 | Zhang .......................... 623/1.42 |
| 2007/0156231 A1 | 7/2007 | Weber | | 2009/0118809 A1 | 5/2009 | Scheuermann et al. |
| 2007/0173923 A1 | 7/2007 | Savage et al. | | 2009/0118812 A1 | 5/2009 | Kokate et al. |
| 2007/0181433 A1 | 8/2007 | Birdsall et al. | | 2009/0118813 A1 | 5/2009 | Scheuermann et al. |
| 2007/0190104 A1 | 8/2007 | Kamath et al. | | 2009/0118814 A1 | 5/2009 | Schoenle et al. |
| 2007/0191923 A1 | 8/2007 | Weber et al. | | 2009/0118815 A1 | 5/2009 | Arcand et al. |
| 2007/0191928 A1 | 8/2007 | Rolando et al. | | 2009/0118818 A1 | 5/2009 | Foss et al. |
| 2007/0191931 A1 | 8/2007 | Weber et al. | | 2009/0118820 A1 | 5/2009 | Gregorich et al. |
| 2007/0191943 A1 | 8/2007 | Shrivastava et al. | | 2009/0118821 A1 | 5/2009 | Scheuermann et al. |
| 2007/0198081 A1 | 8/2007 | Castro et al. | | 2009/0118822 A1 | 5/2009 | Holman et al. |
| 2007/0202466 A1 | 8/2007 | Schwarz et al. | | 2009/0118823 A1 | 5/2009 | Atanasoska et al. |
| 2007/0207186 A1 | 9/2007 | Scanlon et al. | | 2009/0123517 A1 | 5/2009 | Flanagan et al. |
| 2007/0208412 A1 | 9/2007 | Elmaleh | | 2009/0123521 A1 | 5/2009 | Weber et al. |
| 2007/0212547 A1 | 9/2007 | Fredrickson et al. | | 2009/0138077 A1 | 5/2009 | Weber et al. |
| 2007/0213827 A1 | 9/2007 | Arramon | | 2009/0149942 A1 | 6/2009 | Edelman et al. |
| 2007/0219626 A1 | 9/2007 | Rolando et al. | | 2009/0157165 A1 | 6/2009 | Miller et al. |
| 2007/0224116 A1 | 9/2007 | Chandrasekaran et al. | | 2009/0157166 A1* | 6/2009 | Singhal et al. ............... 623/1.15 |
| 2007/0224224 A1 | 9/2007 | Cordeira Da Silva et al. | | 2009/0157172 A1 | 6/2009 | Kokate et al. |
| 2007/0224235 A1 | 9/2007 | Tenney et al. | | 2009/0177273 A1* | 7/2009 | Piveteau et al. .............. 623/1.46 |
| 2007/0224244 A1 | 9/2007 | Weber et al. | | 2009/0186068 A1 | 7/2009 | Miller et al. |
| 2007/0244569 A1 | 10/2007 | Weber et al. | | 2009/0192593 A1 | 7/2009 | Meyer et al. |
| 2007/0254091 A1 | 11/2007 | Fredrickson et al. | | 2009/0202610 A1 | 8/2009 | Wilson |
| 2007/0255392 A1 | 11/2007 | Johnson | | 2009/0208428 A1 | 8/2009 | Hill et al. |
| 2007/0264303 A1 | 11/2007 | Atanasoska et al. | | 2009/0220612 A1 | 9/2009 | Perera |
| 2007/0269480 A1 | 11/2007 | Richard et al. | | 2009/0259300 A1 | 10/2009 | Dorogy, Jr. et al. |
| 2007/0299509 A1 | 12/2007 | Ding | | 2009/0264975 A1* | 10/2009 | Flanagan et al. ................ 623/1.2 |
| 2008/0003251 A1 | 1/2008 | Zhou | | 2009/0281613 A1 | 11/2009 | Atanasoska et al. |
| 2008/0004691 A1 | 1/2008 | Weber et al. | | 2009/0287301 A1 | 11/2009 | Weber |
| 2008/0008654 A1 | 1/2008 | Clarke et al. | | 2009/0306765 A1 | 12/2009 | Weber |
| 2008/0038146 A1 | 2/2008 | Wachter et al. | | 2009/0317766 A1* | 12/2009 | Heidenau et al. ........... 433/201.1 |
| 2008/0050413 A1 | 2/2008 | Horvers et al. | | 2010/0008970 A1 | 1/2010 | O'Brien et al. |
| 2008/0050415 A1 | 2/2008 | Atanasoska et al. | | 2010/0030326 A1 | 2/2010 | Radhakrishnan et al. |
| 2008/0051881 A1 | 2/2008 | Feng et al. | | 2010/0042206 A1* | 2/2010 | Yadav et al. .................. 623/1.42 |
| 2008/0057103 A1 | 3/2008 | Roorda | | 2010/0057197 A1* | 3/2010 | Weber et al. ................. 623/1.42 |
| 2008/0058921 A1 | 3/2008 | Lindquist | | 2010/0070022 A1* | 3/2010 | Kuehling ...................... 623/1.16 |
| 2008/0069854 A1 | 3/2008 | Xiao et al. | | 2010/0070026 A1* | 3/2010 | Ito et al. ....................... 623/1.39 |
| 2008/0071349 A1 | 3/2008 | Atanasoska et al. | | | | |
| 2008/0071350 A1 | 3/2008 | Stinson | | | | |

FOREIGN PATENT DOCUMENTS

| | | |
|---|---|---|
| AT | 288234 | 2/2005 |
| AU | 4825696 | 10/1996 |
| AU | 5588896 | 12/1996 |
| AU | 5266698 | 6/1998 |
| AU | 6663298 | 9/1998 |
| AU | 716005 | 2/2000 |
| AU | 5686499 | 3/2000 |
| AU | 2587100 | 5/2000 |
| AU | 2153600 | 6/2000 |
| AU | 1616201 | 5/2001 |
| AU | 737252 | 8/2001 |
| AU | 2317701 | 8/2001 |
| AU | 5215401 | 9/2001 |
| AU | 5890401 | 12/2001 |
| AU | 3597401 | 6/2002 |
| AU | 2002353068 | 3/2003 |
| AU | 2002365875 | 6/2003 |
| AU | 2003220153 | 9/2003 |
| AU | 2003250913 | 1/2004 |
| AU | 770395 | 2/2004 |
| AU | 2003249017 | 2/2004 |
| AU | 2003256499 | 2/2004 |
| AU | 771367 | 3/2004 |
| AU | 2003271633 | 4/2004 |
| AU | 2003272710 | 4/2004 |
| AU | 2003285195 | 6/2004 |
| AU | 2003287633 | 6/2004 |
| AU | 2003290675 | 6/2004 |
| AU | 2003290676 | 6/2004 |
| AU | 2003291470 | 6/2004 |
| AU | 2003295419 | 6/2004 |
| AU | 2003295535 | 6/2004 |
| AU | 2003295763 | 6/2004 |
| AU | 2004202073 | 6/2004 |
| AU | 2003300323 | 7/2004 |
| AU | 2004213021 | 9/2004 |
| AU | 2003293557 | 1/2005 |
| AU | 780539 | 3/2005 |
| BR | 8701135 | 1/1988 |
| BR | 0207321 | 2/2004 |
| BR | 0016957 | 6/2004 |
| BR | 0316065 | 9/2005 |
| BR | 0316102 | 9/2005 |
| CA | 1283505 | 4/1991 |
| CA | 2172187 | 10/1996 |
| CA | 2178541 | 12/1996 |
| CA | 2234787 | 10/1998 |
| CA | 2235031 | 10/1998 |
| CA | 2238837 | 2/1999 |
| CA | 2340652 | 3/2000 |
| CA | 2392006 | 5/2001 |
| CA | 2337565 | 8/2001 |
| CA | 2409862 | 11/2001 |
| CA | 2353197 | 1/2002 |
| CA | 2429356 | 8/2002 |
| CA | 2435306 | 8/2002 |
| CA | 2436241 | 8/2002 |
| CA | 2438095 | 8/2002 |
| CA | 2460334 | 3/2003 |
| CA | 2425665 | 4/2003 |
| CA | 2465704 | 4/2003 |
| CA | 2464906 | 5/2003 |
| CA | 2468677 | 6/2003 |
| CA | 2469744 | 6/2003 |
| CA | 2484383 | 1/2004 |
| CA | 2497602 | 4/2004 |
| CA | 2499976 | 4/2004 |
| CA | 2503625 | 5/2004 |
| CA | 2504524 | 5/2004 |
| CA | 2505576 | 5/2004 |
| CA | 2513721 | 5/2004 |
| CA | 2505080 | 6/2004 |
| CA | 2506622 | 6/2004 |
| CA | 2455670 | 7/2004 |
| CA | 2508247 | 7/2004 |
| CA | 2458172 | 8/2004 |
| CA | 2467797 | 11/2004 |
| CA | 2258898 | 1/2005 |
| CA | 2308177 | 1/2005 |
| CA | 2475968 | 1/2005 |
| CA | 2489668 | 6/2005 |
| CA | 2490170 | 6/2005 |
| CA | 2474367 | 1/2006 |
| CA | 2374090 | 5/2007 |
| CA | 2282748 | 11/2007 |
| CA | 2336650 | 1/2008 |
| CA | 2304325 | 5/2008 |
| CN | 1430491 | 7/2003 |
| CN | 1547490 | 11/2004 |
| CN | 1575154 | 2/2005 |
| CN | 1585627 | 2/2005 |
| CN | 1669537 | 9/2005 |
| DE | 3516411 | 11/1986 |
| DE | 3608158 | 9/1987 |
| DE | 19916086 | 10/1999 |
| DE | 19855421 | 5/2000 |
| DE | 19916315 | 9/2000 |
| DE | 9422438 | 4/2002 |
| DE | 1096902 | 5/2002 |
| DE | 10064596 | 6/2002 |
| DE | 10107339 | 9/2002 |
| DE | 69712063 | 10/2002 |
| DE | 10127011 | 12/2002 |
| DE | 10150995 | 4/2003 |
| DE | 69807634 | 5/2003 |
| DE | 69431457 | 6/2003 |
| DE | 10200387 | 8/2003 |
| DE | 69719161 | 10/2003 |
| DE | 02704283 | 4/2004 |
| DE | 60106962 | 4/2005 |
| DE | 60018318 | 12/2005 |
| DE | 69732439 | 1/2006 |
| DE | 69828798 | 1/2006 |
| DE | 102004044738 | 3/2006 |
| DE | 69830605 | 5/2006 |
| DE | 102005010100 | 9/2006 |
| DE | 602005001867 | 5/2008 |
| DE | 69829015 | 3/2009 |
| DK | 127987 | 9/1987 |
| DK | 914092 | 8/2002 |
| EP | 0222853 | 5/1987 |
| EP | 0129147 | 1/1990 |
| EP | 0734721 | 10/1996 |
| EP | 0650604 | 9/1998 |
| EP | 0865762 | 9/1998 |
| EP | 0875217 | 11/1998 |
| EP | 0633840 | 11/1999 |
| EP | 0953320 | 11/1999 |
| EP | 0971644 | 1/2000 |
| EP | 0982041 | 3/2000 |
| EP | 1105169 | 6/2001 |
| EP | 1124594 | 8/2001 |
| EP | 1127582 | 8/2001 |
| EP | 1131127 | 9/2001 |
| EP | 1132058 | 9/2001 |
| EP | 1150738 | 11/2001 |
| EP | 1172074 | 1/2002 |
| EP | 1181943 | 2/2002 |
| EP | 0914092 | 4/2002 |
| EP | 1216665 | 6/2002 |
| EP | 0747069 | 9/2002 |
| EP | 0920342 | 9/2002 |
| EP | 1242130 | 9/2002 |
| EP | 0623354 | 10/2002 |
| EP | 0806211 | 10/2002 |
| EP | 1275352 | 1/2003 |
| EP | 0850604 | 2/2003 |
| EP | 1280512 | 2/2003 |
| EP | 1280568 | 2/2003 |
| EP | 1280569 | 2/2003 |
| EP | 1294309 | 3/2003 |
| EP | 0824900 | 4/2003 |
| EP | 1308179 | 5/2003 |
| EP | 1310242 | 5/2003 |
| EP | 1314405 | 5/2003 |
| EP | 1 319 416 A1 | 6/2003 |
| EP | 1316323 | 6/2003 |

| | | | | | |
|---|---|---|---|---|---|
| EP | 1339448 | 9/2003 | EP | 1796754 | 6/2007 |
| EP | 1347791 | 10/2003 | EP | 1330273 | 7/2007 |
| EP | 1347792 | 10/2003 | EP | 0900060 | 8/2007 |
| EP | 1348402 | 10/2003 | EP | 1355588 | 8/2007 |
| EP | 1348405 | 10/2003 | EP | 1355589 | 8/2007 |
| EP | 1359864 | 11/2003 | EP | 1561436 | 8/2007 |
| EP | 1365710 | 12/2003 | EP | 1863408 | 12/2007 |
| EP | 1379290 | 1/2004 | EP | 1071490 | 1/2008 |
| EP | 0902666 | 2/2004 | EP | 1096902 | 1/2008 |
| EP | 1460972 | 2/2004 | EP | 0895762 | 2/2008 |
| EP | 0815806 | 3/2004 | EP | 0916317 | 2/2008 |
| EP | 1400219 | 3/2004 | EP | 1891988 | 2/2008 |
| EP | 0950386 | 4/2004 | EP | 1402849 | 4/2008 |
| EP | 1461165 | 4/2004 | EP | 1466634 | 7/2008 |
| EP | 1416884 | 5/2004 | EP | 1572032 | 7/2008 |
| EP | 1424957 | 6/2004 | EP | 1527754 | 8/2008 |
| EP | 1429816 | 6/2004 | EP | 1968662 | 9/2008 |
| EP | 1448116 | 8/2004 | EP | 1980223 | 10/2008 |
| EP | 1448118 | 8/2004 | EP | 1988943 | 11/2008 |
| EP | 1449545 | 8/2004 | EP | 1490125 | 1/2009 |
| EP | 1449546 | 8/2004 | EP | 1829626 | 2/2009 |
| EP | 1254674 | 9/2004 | EP | 1229901 | 3/2009 |
| EP | 1453557 | 9/2004 | EP | 1128785 | 4/2009 |
| EP | 1457214 | 9/2004 | EP | 2051750 | 4/2009 |
| EP | 0975340 | 10/2004 | EP | 1427353 | 5/2009 |
| EP | 1319416 | 11/2004 | ES | 2169012 | 7/2002 |
| EP | 1476882 | 11/2004 | FR | 2867059 | 9/2005 |
| EP | 1479402 | 11/2004 | GB | 2397233 | 7/2004 |
| EP | 1482867 | 12/2004 | JP | 7002180 | 1/1995 |
| EP | 1011529 | 1/2005 | JP | 3673973 | 2/1996 |
| EP | 0875218 | 2/2005 | JP | 3249383 | 10/1996 |
| EP | 1181903 | 2/2005 | JP | 3614652 | 11/1998 |
| EP | 1504775 | 2/2005 | JP | 10295824 | 11/1998 |
| EP | 1042997 | 3/2005 | JP | 11188109 | 7/1999 |
| EP | 1754684 | 3/2005 | JP | 2000312721 | 11/2000 |
| EP | 1520594 | 4/2005 | JP | 2001098308 | 4/2001 |
| EP | 1521603 | 4/2005 | JP | 2001522640 | 11/2001 |
| EP | 1028672 | 6/2005 | JP | 2002065862 | 3/2002 |
| EP | 1539041 | 6/2005 | JP | 2002519139 | 7/2002 |
| EP | 1543798 | 6/2005 | JP | 2002523147 | 7/2002 |
| EP | 1550472 | 6/2005 | JP | 2003024449 | 1/2003 |
| EP | 1328213 | 7/2005 | JP | 2003521274 | 7/2003 |
| EP | 1551569 | 7/2005 | JP | 2003290361 | 10/2003 |
| EP | 1554992 | 7/2005 | JP | 2003533333 | 11/2003 |
| EP | 1560613 | 8/2005 | JP | 2004500925 | 1/2004 |
| EP | 1562519 | 8/2005 | JP | 2004522559 | 7/2004 |
| EP | 1562654 | 8/2005 | JP | 2004223264 | 8/2004 |
| EP | 1570808 | 9/2005 | JP | 2004267750 | 9/2004 |
| EP | 1575631 | 9/2005 | JP | 2004275748 | 10/2004 |
| EP | 1575638 | 9/2005 | JP | 2004305753 | 11/2004 |
| EP | 1575642 | 9/2005 | JP | 2005501654 | 1/2005 |
| EP | 0900059 | 10/2005 | JP | 2005502426 | 1/2005 |
| EP | 1581147 | 10/2005 | JP | 2005040584 | 2/2005 |
| EP | 1586286 | 10/2005 | JP | 2005503184 | 2/2005 |
| EP | 1254673 | 11/2005 | JP | 2005503240 | 2/2005 |
| EP | 1261297 | 11/2005 | JP | 2005507285 | 3/2005 |
| EP | 0927006 | 1/2006 | JP | 2005511139 | 4/2005 |
| EP | 1621603 | 2/2006 | JP | 2005511242 | 4/2005 |
| EP | 1218665 | 5/2006 | JP | 2005131364 | 5/2005 |
| EP | 1222941 | 5/2006 | JP | 2005152526 | 6/2005 |
| EP | 1359867 | 5/2006 | JP | 2005152527 | 6/2005 |
| EP | 1656961 | 5/2006 | JP | 2005199054 | 7/2005 |
| EP | 1277449 | 6/2006 | JP | 2005199058 | 7/2005 |
| EP | 0836839 | 7/2006 | JP | 2008516726 | 5/2008 |
| EP | 1684817 | 8/2006 | KR | 2002/0066996 | 8/2002 |
| EP | 1687042 | 8/2006 | KR | 2004/0066409 | 7/2004 |
| EP | 0907339 | 11/2006 | KR | 2005/0117361 | 12/2005 |
| EP | 1359865 | 11/2006 | NZ | 331388 | 1/2000 |
| EP | 1214108 | 1/2007 | SU | 393044 | 12/1973 |
| EP | 1416885 | 1/2007 | WO | WO86/06617 | 11/1986 |
| EP | 1441667 | 1/2007 | WO | WO93/06792 | 4/1993 |
| EP | 1192957 | 2/2007 | WO | WO93/07934 | 4/1993 |
| EP | 1236447 | 2/2007 | WO | WO93/16656 | 9/1993 |
| EP | 1764116 | 3/2007 | WO | WO94/16646 | 8/1994 |
| EP | 1185215 | 4/2007 | WO | WO95/03083 | 2/1995 |
| EP | 1442757 | 4/2007 | WO | WO96/04952 | 2/1996 |
| EP | 1786363 | 5/2007 | WO | WO96/09086 | 3/1996 |
| EP | 1787602 | 5/2007 | WO | WO96/32907 | 10/1996 |
| EP | 1788973 | 5/2007 | WO | WO97/041916 | 11/1997 |

| | | | | | | |
|---|---|---|---|---|---|---|
| WO | WO98/17331 | 4/1998 | | WO | WO2004/010900 | 2/2004 |
| WO | WO98/18408 | 5/1998 | | WO | WO2004/014554 | 2/2004 |
| WO | WO98/23228 | 6/1998 | | WO | WO2004/026177 | 4/2004 |
| WO | WO98/36784 | 8/1998 | | WO | WO2004/028347 | 4/2004 |
| WO | WO98/38946 | 9/1998 | | WO | WO2004/028587 | 4/2004 |
| WO | WO98/38947 | 9/1998 | | WO | WO2004/043292 | 5/2004 |
| WO | WO98/040033 | 9/1998 | | WO | WO2004/043298 | 5/2004 |
| WO | WO98/57680 | 12/1998 | | WO | WO2004/043300 | 5/2004 |
| WO | WO99/16386 | 4/1999 | | WO | WO2004/043509 | 5/2004 |
| WO | WO99/23977 | 5/1999 | | WO | WO2004/043511 | 5/2004 |
| WO | WO99/042631 | 8/1999 | | WO | WO2004/045464 | 6/2004 |
| WO | WO99/49928 | 10/1999 | | WO | WO2004/045668 | 6/2004 |
| WO | WO99/52471 | 10/1999 | | WO | WO2004/058100 | 7/2004 |
| WO | WO99/62432 | 12/1999 | | WO | WO2004/060428 | 7/2004 |
| WO | WO00/01322 | 1/2000 | | WO | WO2004/064911 | 8/2004 |
| WO | WO00/10622 | 3/2000 | | WO | WO2004/071548 | 8/2004 |
| WO | WO00/25841 | 5/2000 | | WO | WO2004/072104 | 8/2004 |
| WO | WO00/27303 | 5/2000 | | WO | WO2004/073768 | 9/2004 |
| WO | WO00/30710 | 6/2000 | | WO | WO2004/080579 | 9/2004 |
| WO | WO00/48660 | 8/2000 | | WO | WO2004/087251 | 10/2004 |
| WO | WO00/64506 | 11/2000 | | WO | WO2004/096176 | 11/2004 |
| WO | WO01/35928 | 5/2001 | | WO | WO2004/105639 | 12/2004 |
| WO | WO01/41827 | 6/2001 | | WO | WO2004/108021 | 12/2004 |
| WO | WO01/45862 | 6/2001 | | WO | WO2004/108186 | 12/2004 |
| WO | WO01/45763 | 7/2001 | | WO | WO2004/108346 | 12/2004 |
| WO | WO01/66036 | 9/2001 | | WO | WO2004/110302 | 12/2004 |
| WO | WO01/80920 | 11/2001 | | WO | WO2005/004754 | 1/2005 |
| WO | WO01/87263 | 11/2001 | | WO | WO2005/006325 | 1/2005 |
| WO | WO01/87342 | 11/2001 | | WO | WO2005/011529 | 2/2005 |
| WO | WO01/87374 | 11/2001 | | WO | WO2005/014892 | 2/2005 |
| WO | WO01/89417 | 11/2001 | | WO | WO2005/027794 | 3/2005 |
| WO | WO01/89420 | 11/2001 | | WO | WO2005/032456 | 4/2005 |
| WO | WO 02/74431 A1 | 3/2002 | | WO | WO2005/034806 | 4/2005 |
| WO | WO02/26162 | 4/2002 | | WO | WO2005/042049 | 5/2005 |
| WO | WO02/30487 | 4/2002 | | WO | WO2005/044361 | 5/2005 |
| WO | WO02/38827 | 5/2002 | | WO | WO 2005/115496 A1 | 5/2005 |
| WO | WO02/42521 | 5/2002 | | WO | WO2005/049520 | 6/2005 |
| WO | WO02/43796 | 6/2002 | | WO | WO2005/051450 | 6/2005 |
| WO | WO02/47581 | 6/2002 | | WO | WO2005/053766 | 6/2005 |
| WO | WO02/058753 | 8/2002 | | WO | WO2005/063318 | 7/2005 |
| WO | WO02/060349 | 8/2002 | | WO | WO2005/072437 | 8/2005 |
| WO | WO02/060350 | 8/2002 | | WO | WO2005/082277 | 9/2005 |
| WO | WO02/060506 | 8/2002 | | WO | WO2005/082283 | 9/2005 |
| WO | WO02/064019 | 8/2002 | | WO | WO2005/086733 | 9/2005 |
| WO | WO02/065947 | 8/2002 | | WO | WO2005/089825 | 9/2005 |
| WO | WO02/069848 | 9/2002 | | WO | WO2005/091834 | 10/2005 |
| WO | WO02/074431 | 9/2002 | | WO | WO2005/099621 | 10/2005 |
| WO | WO02/076525 | 10/2002 | | WO | WO2005/099626 | 10/2005 |
| WO | WO02/078668 | 10/2002 | | WO | WO2005/110285 | 11/2005 |
| WO | WO02/083039 | 10/2002 | | WO | WO2005/115276 | 12/2005 |
| WO | WO02/085253 | 10/2002 | | WO | WO2005/115496 | 12/2005 |
| WO | WO02/085424 | 10/2002 | | WO | WO2005/117752 | 12/2005 |
| WO | WO02/085532 | 10/2002 | | WO | WO2006/014969 | 2/2006 |
| WO | WO02/096389 | 12/2002 | | WO | WO2006/015161 | 2/2006 |
| WO | WO03/009779 | 2/2003 | | WO | WO2006/020742 | 2/2006 |
| WO | WO03/022178 | 3/2003 | | WO | WO2006/029364 | 3/2006 |
| WO | WO03/024357 | 3/2003 | | WO | WO2006/029708 | 3/2006 |
| WO | WO03/026713 | 4/2003 | | WO | WO2006/036801 | 4/2006 |
| WO | WO03/035131 | 5/2003 | | WO | WO2006/055237 | 5/2006 |
| WO | WO03/037220 | 5/2003 | | WO | WO2006/061598 | 6/2006 |
| WO | WO03/037221 | 5/2003 | | WO | WO2006/063157 | 6/2006 |
| WO | WO03/037223 | 5/2003 | | WO | WO2006/063158 | 6/2006 |
| WO | WO03/037398 | 5/2003 | | WO | WO2006/083418 | 8/2006 |
| WO | WO03/039407 | 5/2003 | | WO | WO2006/104644 | 10/2006 |
| WO | WO03/045582 | 6/2003 | | WO | WO2006/104976 | 10/2006 |
| WO | WO03/047463 | 6/2003 | | WO | WO2006/105256 | 10/2006 |
| WO | WO03/051233 | 6/2003 | | WO | WO2006/107677 | 10/2006 |
| WO | WO03/055414 | 7/2003 | | WO | WO2006/116752 | 11/2006 |
| WO | WO03/061755 | 7/2003 | | WO | WO2006/124365 | 11/2006 |
| WO | WO03/072287 | 9/2003 | | WO | WO2007/016961 | 2/2007 |
| WO | WO03/077802 | 9/2003 | | WO | WO2007/034167 | 3/2007 |
| WO | WO03/083181 | 10/2003 | | WO | WO2007/070666 | 6/2007 |
| WO | WO03/094774 | 11/2003 | | WO | WO2007/095167 | 8/2007 |
| WO | WO2004/004602 | 1/2004 | | WO | WO2007/124137 | 11/2007 |
| WO | WO2004/004603 | 1/2004 | | WO | WO2007/126768 | 11/2007 |
| WO | WO2004/006491 | 1/2004 | | WO | WO2007/130786 | 11/2007 |
| WO | WO2004/006807 | 1/2004 | | WO | WO2007/133520 | 11/2007 |
| WO | WO2004/006976 | 1/2004 | | WO | WO2007/143433 | 12/2007 |
| WO | WO2004/006983 | 1/2004 | | WO | WO2007/145961 | 12/2007 |

| | | |
|---|---|---|
| WO | WO2007/147246 | 12/2007 |
| WO | WO2008/002586 | 1/2008 |
| WO | WO2008/002778 | 1/2008 |
| WO | WO2008/024149 | 2/2008 |
| WO | WO2008/024477 | 2/2008 |
| WO | WO2008/024669 | 2/2008 |
| WO | WO2008/033711 | 3/2008 |
| WO | WO2008/034048 | 3/2008 |
| WO | WO2008/036549 | 3/2008 |
| WO | WO2008/039319 | 4/2008 |
| WO | WO2008/045184 | 4/2008 |
| WO | WO2008/057991 | 5/2008 |
| WO | WO2008/061017 | 5/2008 |
| WO | WO2008/063539 | 5/2008 |
| WO | WO2008/082698 | 7/2008 |
| WO | WO2008/106223 | 9/2008 |
| WO | WO2008/108987 | 9/2008 |
| WO | WO2008/124513 | 10/2008 |
| WO | WO2008/124519 | 10/2008 |
| WO | WO2008/140482 | 11/2008 |
| WO | WO2008/147848 | 12/2008 |
| WO | WO2008/147853 | 12/2008 |
| WO | WO2009/009627 | 1/2009 |
| WO | WO2009/009628 | 1/2009 |
| WO | WO2009/012353 | 1/2009 |
| WO | WO2009/014692 | 1/2009 |
| WO | WO2009/014696 | 1/2009 |
| WO | WO2009/020520 | 2/2009 |
| WO | WO2009/059081 | 5/2009 |
| WO | WO2009/059085 | 5/2009 |
| WO | WO2009/059086 | 5/2009 |
| WO | WO2009/059098 | 5/2009 |
| WO | WO2009/059129 | 5/2009 |
| WO | WO2009/059141 | 5/2009 |
| WO | WO2009/059146 | 5/2009 |
| WO | WO2009/059165 | 5/2009 |
| WO | WO2009/059166 | 5/2009 |
| WO | WO2009/059180 | 5/2009 |
| WO | WO2009/059196 | 5/2009 |
| WO | WO2009/089382 | 7/2009 |
| WO | WO2009/091384 | 7/2009 |
| WO | WO2009/094270 | 7/2009 |
| WO | WO2009/126766 | 10/2009 |
| ZA | 9710342 | 6/1998 |

OTHER PUBLICATIONS

N. Fujisawa et al., "A novel textured surface for blood-contact", *Biomaterials*, vol. 20, (1999), pp. 955-962.

MicroFab: Technology: Research and Development: Biomedical Applications: Stents, downloaded Mar. 23, 2007 from http://www.microfab.com/technology/biomedical/Stents.html.

G. Kickelbick, "Concepts for the incorporation of inorganic building blocks into organic polymers on a nanoscale", *Prog. Polym. Sci.*, vol. 28, (2003), pp. 83-114.

R.G. Flemming et al., "Effects of synthetic micro- and nano-structured surfaces on cell behavior", *Biomaterials*, vol. 20, (1999), pp. 573-588.

W.Y. Leung et al., "Fabrication of photonic band gap crystal using microtransfer molded templates", *Journal of Applied Physics*, vol. 93, No. 10, May 15, 2003, pp. 5866-5870.

"Functionalization of Polymer Surfaces," *Europlasma Technical Paper*, May 8, 2004, pp. 1-29.

M. S. Kumar et al., "Influence of electric field type on the assembly of single walled carbon nanotubes", *Chemical Physics Letters*, vol. 383, (2004), pp. 235-239.

J.G. Qasem et al., "Kinetics of Paclitaxel 2'-N-methylpyridinium Mesylate Decomposition", *AAPS PharmSciTech*, vol. 4, No. 2, Article 21, (2003), 8 pgs.

M. J. Jensen et al., "Low-temperature preparation of nanocrystalline anatase films through a sol-gel route", *J. Sol-Gel-Sci. Techn.*, vol. 39, (2006), pp. 229-233.

K. Sasahara et al., "Macroporous and nanosized ceramic films prepared by modified sol-gel method with PMMA microsphere templates", *Journal of the European Ceramic Society*, vol. 24, (2004), pp. 1961-1967.

M. Spasova et al., "Magnetic and optical tunable microspheres with a magnetite/gold nanoparticle shell", *J. Mater. Chem.*, vol. 15, (2005), pp. 2095-2098.

S. C. Daxini et al., "Micropatterned polymer surfaces improve retention of endothelial cells exposed to flow-induced shear stress", *Biorheology*, vol. 43, (2006), pp. 45-55.

J. Park et al., "Multilayer Transfer Printing for Polyelectrolyte Multilayer Patterning: Direct Transfer of Layer-by-Layer Assembled Micropatterned Thin Films", *Ad. Mater.*, vol. 16, No. 6, Mar. 18, 2004, pp. 520-525.

Next-generation drug-eluting stents tackle shortcomings of Cypher, Taxus, downloaded Mar. 26, 2007 from http://www.theheart.org/article/641591.do.

E.W.P. Damen et al., "Paclitaxel Esters of Malic Acid as Prodrugs with Improved Water Solubility", *Bioorganic & Medicinal Chemistry*, vol. 8, (2000), pp. 427-432.

N. Kumar et al., "Polyanhydrides: an overview", *Advanced Drug Delivery Reviews*, vol. 54, (2002), pp. 889-910.

D. Wang et al., "Polyelectrolyte-Coated Colloid Spheres as Templates for Sol-Gel Reactions", *Chem. Mater.*, vol. 14, (2002), pp. 1909-1913.

H. Kong et al., "Polyelectrolyte-functionalized multiwalled carbon nanotubes: preparation, characterization and layer-by-layer self-assembly", *Polymer*, vol. 46, (2005), pp. 2472-2485.

R. Duncan et al., "Polymer-drug conjugates, PDEPT and PELT: basic principals for design and transfer from the laboratory to clinic", *Journal of Controlled Release*, vol. 74, (2001), pp. 135-146.

C. Li, "Poly(L-glutamic acid)-anticancer drug conjugates", *Advanced Drug Delivery Reviews*, vol. 54, (2002), pp. 695-713.

H. Imai et al, "Preparation of Porous Anatase Coating from Sol-Gel Derived Titanium Dioxide and Titanium Dioxide-Silica by Water-Vapor Exposure", *J. Am. Ceram. Soc.*, vol. 82, No. 9, (1999), pp. 2301-304.

S. Kidambi et al., "Selective Depositions on Polyelectrolyte Multilayers: Self-Assembled Monolayers of m-dPEG Acid as Molecular Template", *J. Am. Chem. Soc.*, vol. 126, (2004), pp. 4697-4703.

E. K. F. Yim et al., "Significance of synthetic nanostructures in dictating cellular response", *Nanomedicine: Nanotechnology, Biology, and Medicine*, vol. 1, (2005), pp. 10-21.

"Biomaterials to Promote Tissue Regeneration" in Standard handbook of biomedical engineering and design, Meyer Kutz, Ed., 2003 ISBN 0-07-135637-1, p. 16.13-16.29.

R. Viitala et al., "Surface properties of in vitro bioactive and non-bioactive sol-gel derived materials", *Biomaterials*, vol. 23, (2002), pp. 3073-3086.

M. Advincula et al., "Surface modification of surface sol-gel derived titanium oxide films by self-assembled monolayers (SAMs) and non-specific protein adsorption studies", *Colloids and Surfaces B: Biointerfaces*, vol. 42, (2005), pp. 29-43.

D. Wang et al., "Synthesis of Macroporous Titania and Inorganic Composite Materials from Coated Colloidal Spheres —A Novel Route to Tune Pore Morphology", *Chem. Mater.*, vol. 13, (2001), pp. 364-371.

J. Y. Lim et al., "Systematic variation in osteoblast adhesion and phenotype with substratum surface characteristics", *J. Biomed. Mater. Res.*, vol. 68A, No. 3, (2004), pp. 504-512.

"Terumo Europe N. V. Enrols First Patient in Clinical Trial of the Nobori™ Drug-eluting Coronary Stent", downloaded on Mar. 26, 2007 from http://www.terumo-europe.com/_press_releases/may_26_2005.html.

J. M. Caves et al., "The evolving impact of microfabrication and nanotechnology on stent design", *J. Vasc. Surg.*, vol. 44, (2006), pp. 1363-1368.

R. Duncan, The Dawning Era of Polymer Therapeutics, *Nature Reviews/Drug Discovery*, vol. 2, May 2003, pp. 347-360.

S. L. Goodman et al., "Three-dimensional extracellular matrix textured biomaterials", *Biomaterials*, vol. 17, (1996), pp. 2087-2095.

I. Ichinose et al., "Ultrathin composite films: An indispensable resource for nanotechnology", *Riken Review*, No. 37, Jul. 2001, pp. 34-37.

U.S. Appl. No. 11/694,436, filed Mar. 30, 2007, Atanasoska et al.

"Cyclic voltammetry"—from Wikipedia, (http://en.wikipedia.org/wiki/Cyclic_voltammetry), pp. 1-3, (downloaded [2007]).
"Electrophoretic deposition"—from Wikipedia, (http://en.wikipedia.org/wiki/electrophoretic_deposition), pp. 1-8, (downloaded [2007]).
"Impressive Progress In Interventional Cardiology—From 1st Balloon Inflation To First Bioabsorbable Stent," Medical News Today, pp. 1-2, May 15, 2006, (http://www.medicalnewstoday.com/articles/43313.php).
"JOMED Starts Clinical Studies on Tacrolimus-Eluting Coronary Stents," Jomed Press Release, 2 pages, Jan. 14, 2002.
"Nano PLD," PVD Products, Inc. Wilmington, MA, pp. 1-2, (2003).
"Sputtering," Wikipedia.com, (http://en.wikipedia.org/wiki/Sputtering), pp. 1-5, (downloaded [2009]).
"Ultraviolet-Ozone Surface Treatment," Three Bond Technical News #17, pp. 1-10, Issued Mar. 20, 1987, (http://www.threebond.co.jp/en/technical/technicalnews/pdf/tech17.pdf).
Abbott et al., "Voltammetric and impedance studies of the electropolishing of type 316 stainless steel in a choline chloride based ionic liquid," Electrochimica Acta, vol. 51, pp. 4420-4425, (2006).
Abstract: "Edelstahlfreier stent aus niobium mit iridiumoxyd (IrOx)-beschichtung: Erste Ergebnisse der LUSTY-studie", (Stainless steel-free Stent out of niobium with iridiumoxyd (IrOx)-coating: Initial results of the LUSTY-study), Annual Meeting of the German Society for Cardiology, Apr. 24-26, 2003.
Adanur et al., "Nanocomposite Fiber Based Web and Membrane Formation and Characterization," Journal of Industrial Textiles, vol. 36, No. 4, pp. 311-327, Apr. 2007.
Advincula et al., "Surface modification of surface sol-gel derived titanium oxide films by self-assembled monolayers (SAMs) and non-specific protein adsorption studies," Colloids and Surfaces B: Biointerfaces, vol. 42, pp. 29-43, (2005).
Akhras, "Bare metal stent, lunar IrOx2 coated or drug-eluting stent for patients with CAD?", PowerPoint presentation, pp. 1-20, Oct. 2006.
Akhras, Comparison of Iridiumoxide Coated Stent with Paclitaxel-Eluting Stent and a Bare Metal Stent in Patients With Coronary Artery Disease; Abstract, 1 page, Oct. 2006.
Al-Lamee, "Programmable Elution Profile Coating for Drug-Eluting Stents," Medical Device Technology: Materials, pp. 12-15, Mar. 2005.
Amanatides et al., "Electrical and optical properties of CH4/H2 RF plasmas for diamond-like thin film deposition," Diamond & Related materials, vol. 14, pp. 292-295, (2005).
Amberg et al., "Silver Deposition on Temperature Sensitive Substrates by Means of an Inverted Cylindrical Magnetron," Poster, 1 page, 2003.
Anders, "Ion Plating and Beyond: Pushing the Limits of Energetic Deposition," Vacuum Technology & Coating, pp. 41-46, Dec. 2002.
Andersson et al., "Influence of Systematically Varied Nanoscale Topography on the Morphology of Epithelial Cells," IEEE Transactions on Nanobioscience, vol. 2, No. 2, pp. 49-57, Jun. 2003.
Andersson et al., "Nanoscale features influence epithelial cell morphology and cytokine production," Biomaterials, 2003. vol. 24, No. 20, pp. 3427-3436, (2003).
Annis et al., "An Elastomeric Vascular Prosthesis," Transactions—American Society for Artificial Internal Organs. vol. XXIV, pp. 209-214, (1978).
Ansell et al., "X-Ray Rhotoelectron Spectroscopic Studies of Tin Electrodes after Polarization in Sodium Hydroxide Solution," Journal of Electrochemical Society: Electrochemical Science and Technology, vol. 124, No. 9, pp. 1360-1364, Sep. 1977.
Antunes et al., "Characterization of Corrosion Products Formed on Steels in The First Months of Atmospheric Exposure", Materia, vol. 8, No. 1, pp. 27-34, (2003).
Armani et al., "Microfabrication Technology for Polycaprolactone, a Biodegradable Polymer," Journal of Micromechanics and Microengineering, vol. 10, pp. 80-84, (2000).
Arnold et al., "Activation of Integrin Function by Nanopatterned Adhesive Interface," ChemPhysChem, vol. 5, pp. 383-388, (2004).
Ashfold et al., "Pulsed laser ablation and deposition of thin films," Chem. Soc. Rev., vol. 33, pp. 23-31, (2004).

Asoh et al., "Conditions for Fabrication of Ideally Ordered Anodic Porous Alumina Using Pretextured A1," Journal of The Electrochemical Society, vol. 148, pp. B152-B156, (2001).
Atanasoska et al., "XPS Studies on Conducting Polymers: Polypyrrole Films Doped with Perchlorate and Polymeric Anions," Chemistry Materials vol. 4, pp. 988-994, (1992).
Aughenbaugh et al., "Silica sol-gel for the controlled release of antibiotics. II. The effect of synthesis parameters on the in vitro release kinetics of vancomycin," Journal of Biomedical Materials Research, vol. 57, No. 3, pp. 321-326, Dec. 5, 2001.
Awad et al., "Deposition of duplex A1203/TiN coatings on aluminum alloys for tribological applications using a combined microplasma oxidation (MPO) and arc ion plating (AIP)," Wear, vol. 260, pp. 215-222, (2006).
AxynTec product review, AxynTec Dunnschichttechnik GmbH (www.axyntec.de), pp. 1-8, (2002).
Ayon et al., "Drug loading of nonopouros TiO2 films," Institute of Physics Publishing, Biomedical Materials, vol. 1, pp. L11-L15, (2006).
Azom, "Porous Coatings for Improved Implant Life—Total Hip Replacements," pp. 1-7, [downloaded Sep. 1, 2005], (http://www.azom.com/Details.asp?ArticleID=1900).
Bak et al., "Electrodeposition of polymer next to the three-phase boundary," Electrochemisty Communications, vol. 7, pp. 1098-1104, (2005).
Balamuguran et al., "Bioactive Sol-Gel Hydroxyapatite Surface for Biomedical Applications-In Vitro Study," Trends in Biomaterials & Artificial Organs, vol. 16, No. 1, pp. 18-20, (2002).
Balas et al., "Formation of Bone-Like Apatite on Organic Polymers Treated with a Silane-Coupling Agent and a Titania Solution," Biomaterials, vol. 27, pp. 1704-1710, (2006).
Balaur et al., "Tailoring the wettability of TiO2 nanotube layers," Electrochemistry Communications, vol. 7, pp. 1066-1070, (2005).
Banks et al., "Femtosecond Laser-Induced Forward Transfer (LIFT): A Technique for Versatile Micro-Printing Applications," European Conference on Lasers and Electro-Optics and the International Quantum Electronics Conference, 1 page, Jun. 17-22, 2007.
Banks et al., "Nano-droplets Deposited in Microarrays by Femtosecond Ti: Saphire Laser-Induced Forward Transfer," Optoelectronics Reaserch Centre, University of Southhampton, Applied Physics Letters, vol. 89, Issue 19, pp. 1-12, (2006).
Barbucci et al, Micro and nano-structured surfaces,: Journal of Materials Science: Materials In Medicine, vol. 14, No. 8, pp. 721-725, (2003).
Bates et al. "Description of research activites: Block copolymers," Organization for Minnesota Nanotechnology Institute, University of Minnesota, pp. 1-2, (2002).
Bayoumi et al., "Formation of self-organized titania nano-tubes by dealloying and anodic oxidation," Electrochemistry Communications, vol. 8, pp. 38-44, (2006).
Békési et al., "Efficient Submicron Processing of Metals with Femtosecond UV Pulses," Applied Physics A, vol. 76, pp. 355-357 (2003).
Benson, "Drug Delivery Technology and Access," Polygenetics, Inc., pp. 1-10, Oct. 2005.
Benson, "Highly Porous Polymers," American Laboratory, pp. 1-14, Apr. 2003.
Berg et al., "Controlled Drug Release from Porous Polyelectrolyte Multilayers," Biomacromolecules, vol. 7, pp. 357-364, (2006).
Berkland et al., "Controlling surface nano-structure using flow-limited field-injection electrostatic spraying (FFESS) of poly(D,L-lactide-co-glycolide)," Biomaterials, vol. 25, pp. 5649-5658, (2004).
Berry et al., "The fibroblast response to tubes exhibiting internal nanotopography," Biomaterials, vol. 26, No. 24, pp. 4985-4992, (2005).
Biederman et al. "Plasma Polymer-Metal Composite Films," Plasma Deposition, Treatment and Etching of Polymers, pp. 269-320, (1990).
Bock et al., "Anion and water involvement in hydrous Ir oxide redox reactions in acidic solutions," Journal of Electroanalytical Chemistry, vol. 475, pp. 20-27, (1999).

Bolle et al., "Characterization of submicrometer periodic structures produced on polymer surfaces with low-fluence ultraviolet laser radiation," Journal of Applied Physics, vol. 73, No. 7, pp. 3516-3524, Apr. 1, 1993.

Bolzán et al., "The Potentiodynamic behaviour of iridium electrodes in aqueous 3.7 M H2SO4 in the 293-195 K Range," Journal of Electroanalytical Chemistry, vol. 461, pp. 40-51, (1999).

Boulmedais et la., "Controlled Electrodissolution of Polyelectrolyte Multilayers: A Platform Technology Towards the Surface-Initiated Delivery of Drugs," Advanced Functional Materials, vol. 63, pp. 63-70, (2006).

Boura et al., "Endothelial cell—interactions with polyelectrolyte multilayer films," Biomaterials, vol. 26. pages 4568-4575, (2005).

Bradley et al., "Visuotopic Mapping Through a Multichannel Stimulating Implant in Primate V1," Journal of Neurophysiology, vol. 93, pp. 1659-1670, (2005).

Bretagnol et al., "Functional Micropatterning Surface by Combination of Plasma Polymerization and Lift-Off Process," Plasma Process and Polymers, vol. 3, pp. 30-38, Nov. 14, 2005.

Bretagnol et al., "Surface Functionalization and Patterning Techniques to Design Interfaces for Biomedical and Biosensor Applications," Plasma Processes and Polymers, vol. 3, pp. 443-455, (2006).

Brody et al., "Characterization Nanoscale topography of the Aortic Heart Valve Basement Membrane for Tissue Engineering Heart Valve Scaffold Design," Tissue Engineering, vol. 12, No. 2, pp. 413-421, Nov. 2, 2006.

Bruckner et al., "Metal plasma immersion ion implantation and deposition (MPIIID): chromium on magnesium," Surface and Coatings Technology vol. 103-104, pp. 227-230, (1998).

Brunetti et al., "Oxide/hydroxide films on tin. Part I: Kinetic aspects of the electroformation and electroreductions of the films," Journal of Electroanalytical Chemisty, pp. 1-7, (2007).

Bu et al., "Preparation of nanocrystalline TiO2 porour films from terpineol-ethanol-PEG system," Journal of Materials Science, vol. 41, pp. 2067-2073, (2006).

Bu et al., "Synthesis of TiO2 Porous Thin Films by Polythylene Glycol Templating and Chemistry of the Process," Journal of the European Ceramic Society, vol. 25, pp. 673-679 (2005).

Burmeister et al., "Colloid Monolayers as Versatile Lithographic Masks," Langmuir, vol. 13, pp. 2983-2987, (1997).

Buster et al., "Crystal habits of the Magnesium Hydroxide mineral Brucite within Coral Skeletons," American Geophysical Union Annual Meeting, Abstract and Poster, pp. 1-3, (2006).

Buttiglieri et al., "Endothelization and adherence of leucocytes to nanostructured surfaces," Biomaterials, vol. 24, pp. 2731-2738, (2003).

Calcagno et al., "Structural modification of polymer films by ion irradiation," Nuclear Instruments and Methods in Physics Research, vol. B65, pp. 413-422, (1992).

Carp et al., "Photoinduced Reactivity of Titanium Dioxide," Progress in Solid State Chemistry, vol. 32, pp. 33-177, (2004).

Caruso, "Nanoscale Particle Modifications via Sequential Electrostatic Assembly," Colloids and Colloid Assemblies: Synthesis, Modification, Organization and Utilization of Colloid Particles, pp. 266-269, Mar. 19, 2004.

Cassak, "ART: Bucking the Trend in Bioabsorbable Stents", Windhover Information Inc., In Vivo Jun., pp. 1-14, 2008.

Catledge et al, "Structure and Mechanical Properties of Functionally-Graded Nanostructured Metalloceramic Coatings," Mat. Res. Soc. Symp. Proc. vol. 778, pp. U7.8.1-U7.8.6, (2003).

Catledge et al., "Structural and mechanical properties of nanostructured metalloceramic coatings on cobalt chrome alloys," Applied Physics Letters, vol. 82, No. 10, pp. 1625-1627, Mar. 10, 2003.

Caves et al., "The evolving impact of microfabrication and nanotechnology on stent design," Journal of Vascular Surgery, pp. 1363-1368, Dec. 2006.

Caves et al., "The evolving impact of microfabrication and nanotechnology on stent design," Journal of Vascular Surgury, vol. 44, pp. 1363-1368, (2006).

Cernigoj et al., "Photocatalytically Active TiO2 Thin Films Produced by Surfactant-Assistant Sol-Gel Processing," Thin Solid Films, vol. 495, pp. 327-332, (2006).

Ceruti et al., "Preparation, characterization, cytotoxicity and pharmacokinetics of liposomes containing water-soluble prodrugs of paclitaxel," Journal of Controlled Release, vol. 63, pp. 141-153, (2000).

Champagne et al., "Nanometer-scale scanning sensors fabricated using stencil lithography," Applied Physics Letters, vol. 82, No. 7, pp. 1111-1113, Feb. 17, 2003.

Chandra et al., "Biodegradable Polymers," Progress in Polymer Science, vol. 23, pp. 1273-1335, (1998).

Chang et al., "Preparation and Characterization of Nanostructured Tin Oxide Films by Electrochemical Deposition," Electrochemical and Solid-State Letters, vol. 5, No. 8, pp. C71-C74, (2002).

Chen et al., "Blood compatiblity and sp3/sp2 contents of diamond-like carbon (DLC) synthesized by plasma immersion ion implantation-deposition," Surface and Coatings Technology, vol. 156, pp. 289-294, (2002).

Chen et al., "Fabrication of micro-field emitters on ceramic substrates," Microelectronic Engineering, vol. 84, pp. 94-100, (2007).

Chen et al., "Behavior of Cultured Human Umbilical Vein Endothelial Cells on Titanium Oxie Films Fabricated by Plasma Immersion Ion Implantation and Deposition," Surface & Coatings Technology, vol. 186, pp. 270-276, (2004).

Cheng et al., "Anatase Coating on NiTi Via a Low-Temperature Sol-Gel Route for Improving Corrosion Resistance," Scripta Materialia, vol. 51, pp. 1041-1045, (2004).

Cho et al., "A Novel Route to Three-Dimensionally Ordered Macroporous Polymers by Electron Irradiation of Polymer Colloids" Advanced Materials, vol. 17, No. 1, pp. 120-125, Jan. 6, 2005.

Cho et al., "Influence of Silica on Shape Memory Effect and Mechanical Properties of Polyurethane-Silica Hybrid," European Polymer Journal, vol. 40, pp. 1343-1348, (2004).

Cho et al., "Preparation and Characterization of Iridium Oxide Thin Films Grown by DC Reactive Sputtering," Japanese Journal of Applied Physics, vol. 36, Part 1, No. 3B, pp. 1722-1727, Mar. 1997.

Choi et al., "Synthesis and Characterization of Diamond-Like Carbon Protective AR Coating," Journal of the Korean Physical Society, vol. 45, p. S864, Dec. 2004.

Chougnet et al., "Substrates do influence the ordering of mesoporous thin films," Journal of Materials Chemistry, vol. 15, pp. 3340-3345, (2005).

Chougnet et al., "The Influence of the Nature of the Substrate on the Ordering of Mesoporous Thin Films," Thin Solid Films, vol. 495, pp. 40-44, (2006).

Chow et al., "Nanostructured Films and Coating by Evaporation, Sputtering, Thermal Spraying, Electro and Electroless Deposition," Handbook of Nanophase and Nanostructured Materials, vol. 1, Chapter 9, pp. 246-272, (2003).

Chow et al., "Preliminary Evaluation of KEM for Fabrication," Proceedings of the 12th General Meeting of JOWOG 31, Livermore, CA, University of California, pp. 1-7, (1996).

Chronakis, "Novel nanocomposites and nanoceramics based on polymer nanofibers using electrospinning process—A review," Journal of Materials Processing Technology, vol. 167, pp. 283-293, (2005).

Chu, "Recent developments and applications of plasma immersion ion implantation," Journal of Vacuum Science Technology, vol. B22, No. 1, pp. 289-296, Jan./Feb. 2004.

Chuang et al., "Titanium Oxide and Polyaniline Core-Shell Nanocomposites," Synthetic Metals, vol. 152, pp. 361-364, (2005).

Chung et al., "Roles of discontinuities in bio-inspired adhesive pads," Journal of The Rolyal Society: Interface, vol. 2, pp. 55-61, Feb. 8, 2005.

Clark, "Micropatterning Cell Adhesiveness", Immobilized Biomolecules in Analysis, Oxford University Press, pp. 95-111, (1998).

Clevy et al., "Micromanipulation and Micro-Assembly Systems," IEEE/RAS International Advanced Robotics Program, IARP'06, Paris, France, pp. 1-6, (2006).

Colina et al., "DNA deposition through laser induced forward transfer," Biosensors and Bioelectronics, vol. 20, pp. 1638-1642, (2005).

Costanzo et al., "Model-Based Simulations to Engineer Nanoporous Thin Films," LPCM Research, Pennsylvania State University, pp. 1-3, (2004), (http://1pcm.esm.psu.edu/~tjy107/research.htm).

Course: C-103, "An Introduction to Physical Vapor Deposition (PVD) Processes," Society of Vacuum Coaters, SVS Education Programs: course description and syllabus, pp. 1-4, Apr. 19, 2008.

Course: C-208, "Sputter Deposition in Manufacturing" Society of Vacuum Coaters, SVC Education Programs: course description and syllabus, pp. 1-5, Apr. 22, 2008.

Csete et al., "The existence of sub-micrometer micromechanical modulation generated by polarized UV laser illumination on polymer surfaces," Materials Science and Engineering C, vol. 23, pp. 939-944, (2003).

Csete et al., "The role of original surface roughness in laser-induced periodic surface structure formation process on poly-carbonate films," Thin Solid Films, vol. 453-454, pp. 114-120, (2004).

Curtis et al. "Cells react to nanoscale order and symmetry in their surroundings," IEEE Transactions on Nanobioscience, vol. 3, No. 1, pp. 61-65, Mar. 2004.

Curtis et al., "Nantotechniques and approaches in biotechnology," Trends in Biotechnology, vol. 19, No. 3, pp. 97-101, Mar. 2001.

Curtis et al., "New Depths in Cell Behaviour: Reactions of Cells to Nanotopography," Biochem, Soc, Symp, vol. 65, pp. 15-26, (1999).

Curtis et al., "New depths in cell behaviour: Reactions of cells to nanotopography," Biochemical Society Symposium, No. 65, pp. 15-26 (1997).

Curtis et al., "Topographical Controls of Cells," Biomaterials, vol. 18, pp. 1573-1583, (1997).

Curtis, "Tutorial on the biology of nanotopography," IEEE Transactions on Nanobioscience, vol. 3, No. 4, pp. 293-295, Dec. 2004.

Cyster et al., "The effect of surface chemistry and nanotopography of titanium nitride (TiN) films on 3T3-L1 fibroblasts," Journal of Biomedical Materials Research: A., vol. 67, No. 1, pp. 138-147, Oct. 2003.

Cyster et al., "The effect of surface chemistry and nanotopography of titanium nitride (TiN) films on primary hippocampal neurones," Biomaterials, vol. 25, pp. 97-107, (2004).

da Cruz et al., "Preparation, structure and electrochemistry of a polypyrrole hybrid film with [Pd(dmit)2]2-, bis(1,3-dithiole-2-thione-4,5-dithiolate)palladate(II)," Electrochimica Acta, vol. 52, pp. 1899-1909, (2007).

Dalby et al., "In vitro reaction of endothelial cells to polymer demixed nanotopography," Biomaterials, vol. 23, No. 14, pp. 2945-2954, (2002).

Dalby, "Topographically induced direct cell mechanotransduction," Medical Engineering & Physics, vol. 27, No. 9, pp. 730-742, (2005).

Damen et al., "Paclitaxel Esters of Malic Acid as Prodrugs with Improved Water Solubility," Bioorganic & Medicinal Chemistry, vol. 8, pp. 427-432, (2000).

D'Aquino, "Good Drug Therapy: It's Not Just the Molecule—It's the Delivery," CEP Magazine, (www.cepmagazine.org), 3 pages, Feb. 2004.

Datta et al., "Fundamental aspects and applicatio of electrochemical microfabrication," Electrochimica Acta, vol. 45, pp. 2535-2558, (2000).

Daxini et al., "Micropatterned polymer surface inprove retention of endothelial cells exposed to flow-induced shear stress," Biorheology, vol. 43, pp. 45-55, (2006).

De Aza et al., "Crack growth resistance of alumina, zirconia and zirconia toughened alumina ceramics for joint prostheses," Biomaterials, vol. 23, No. 3, pp. 937-945, Feb. 2002.

Deakin et al., "De-alloying of type 316 stainless steel in hot, concentrated sodium hydroxide solution," Corrosion Science, vol. 46, pp. 2117-2133, (2004).

Debiotech, "Debiostar, An Innovative Solution for Sustained Drug Delivery," pp. 1-4, Copyright 2001, (http://www.debiotech.com/products/drugdd/stent_page_1.html).

Debiotech, "Debiostent: An Innovatice Ceramic Coating for Implantable Medical Devices," pp. 1-2, [first downloaded on Sep. 1, 2005], (http://www.debiotech.com/products/drugdd/stent_page_1.html).

Debiotech, "Debiostent: Polymer free drug eluting coating," Jun. 14, 2007, pp. 1-2, (www.debiotech.com/products/dmggd/stent_page_1.html).

Debiotech, "Debiotech Obtains Exclusive Rights to an Innovative Drug Eluting Stent Technology," Press release, 1 page, Mar. 7, 2003.

Demisse, "Computational Investigation of Conducting Polythiophenes and Substituted Polythiophenes," A Thesis Submitted to the School of Graduate Studies of Addis Ababa University, Ethiopia, pp. 1-86, Jun. 2007.

Deniau et al., "Study of the polymers obtained by electroreduction of methacrylonitrile," Journal of Electroanalytical Chemistry, vol. 505, pp. 33-43, (2001).

Desai et al., "Characterization of micromachined silicon membranes for imrnunoisolation and bioseparation applications," Journal of Membrane Science, vol. 159, pp. 221-231, (1999).

Desai et al., "Use of Microfabricated 'Nanopore' Membranes as a Rate-Limiting Barrier to Diffusion of Small and Large Molecules: Possible Role in Drug Delivery" BioMEMs and Nanotechnology World, pp. 1-2, (2001).

Desai, Integrating Cells with Microsystems: Application in Tissue Engineering and Cell-Based Delivery, PowerPoint presentation, pp. 1-41, May 10, 2002.

Di Mario et al., "Drug-eluting bioabsorbable magnesium stent," Journal of Interventional Cardiology, vol. 17, Issue 6, pp. 1-5, Dec. 2004.

Di Mario et al., "Moonlight: a controlled registry of an iridium oxide-coated stent with angographic follow-up," International Journal of Cardiology, vol. 95, pp. 329-331, (2004).

Di Mario, The Moonlight Study: Multicenter Objective Observational Lunar Iridium Oxide Intimal Growth Trial, PowerPoint presentation, pp. 1-10, (2002).

Dibra et al., "Influence of the stent surface topology on the outcomes of patients undergoing coronary stenting: a randomized double-blind controlled trial", Catheterization and Cardiovascular Interventions, vol. 65, pp. 374-380, (2005).

Dittmar et al., "Nanostructured Smart Drug Delivery Coatings," European Cells and Materials, vol. 31, Supplement 2, p. 73, (2007).

Dong et al., "Preparation of Submicron Polypyrrole/Poly(methly methacrylate) Coaxial Fibers and conversion to Polypyrrole Tubes and Carbon Tubes," Langmuir, vol. 22, pp. 11384-11387, (2006).

Doraiswamy et al., "Excimer laser forward transfer of mammalian cells using a novel triazene absorbing layer," Applied Surface Science, vol. 252, pp. 4743-4747, (2006).

DTI Technology Group: Materials-Coating, "Kinetic spray coating method," www.delphi.com, 1 page, Jul. 2004.

Dumas et al., "Characterization of magnesium fluride thin films produced by argon ion beam-assisted deposition," Thin Solid Films, vol. 382, pp. 61-68, (2001).

Duncan et al., "Polymer-drug conjugates, PDEPT and PELT: basic principals for design and transfer from laboratory to clinic," Journal of Controlled Release, vol. 74, pp. 135-146, (2001).

Duncan, "The Dawning Era of Polymer Therapeutics," Nature Reviews: Drug Discovery, vol. 2, pp. 347-360, May 2003.

Dutta et al., "Self-Organization of Colloidal Nanoparticles," Encyclopedia of Nanoscience and Nanotechnology, vol. 9, pp. 617-640, (2003).

Duwez et al., "Mechanochemistry: targeted delivery of single molecules," Nature Nanotechnology, vol. 1, pp. 122-125, (2006).

EAG Technical Note, "Functional Sites on Non-polymeric Materials: Gas Plasma Treatment and Surface Analysis," Evans Analytical Group, pp. 1-2, (2003).

Eberli et al., "The Lunar Coronary Stent System," Handbook of coronary stents, 4th edition, Chapter 17, 11 pages, (Martin Dunitz Ltd 2002).

Eesley et al., "Thermal properties of kinetics spray Al-SiC metal-matrix composite," Journal of Materials Research, vol. 18, No. 4, pp. 855-860, Apr. 2003.

Egerhazi et al., "Thickness distribution of carbon nitride films grown by inverse-pulsed laster deposition," Applied Surface Science, vol. 247, pp. 182-187, (2005).

Electropolymerization, (http://intel.ucc.ie/sensors/Electropolym.htm), pp. 1-2, (downloaded [2007]).

Erlebacher et al., "Evolution of nonoporosity in dealloying," Nature, vol. 410, pp. 450-453, Mar. 22, 2001.

Esrom et al., "New approach of a laser-induced forward transfer for deposition of patterned thin metal films," Applied Surface Science, vol. 86, pp. 202-207, (1995).

Faupel et al., "Microstructure of pulsed laser deposited ceramic-metal and polymer-metal nanocomposite thin films," Applied Physics A, vol. 79, pp. 1233-1235 (2004).

Faust et al., "Biofunctionalised Biocompatible Titania Coatings for Implants," Euro Ceramics VIII, Key Engineering Materials, vol. 206, No. 2, pp. 1547-1550, (2006).

Fernandez-Pradas et al., "Laser-induced forward transfer of biomolecules," Thin Solid Films, vol. 453-454, pp. 27-30, (2004).

Ferraz et al., "Influence of nanoporesize on platelet adhesion and activation," Journal of Materials Science: Materials in Medicine, vol. 19, pp. 3115-3121, (2008).

Figallo et al., "Micropatterned Biopolymer 3D Scaffold for Static and Dynamic Culture of Human Fibroblasts," Biotechnology Progress, vol. 23, pp. 210-216, (2007).

Flemming et al., "Effects of synthetic micro- and nano-structured surfaces on cell behavior," Biomaterials, vol. 20, No. 6, pp. 573-588, (1999).

Fogarassy et al., "Laser-induced forward transfer: A new approach for the deposition of high Tc superconducting thin films," Journal of Materials Research, vol. 4, No. 5, pp. 1082-1086, Sep./Oct. 1989.

Fonseca et al., "Paclitaxel-loaded PLGA nanoparticles: preparation, physicochemical characterization and in vitro anti-tumoral activity," Journal of Controlled Release, vol. 83 pp. 273-286, (2002).

Forty, "Corrosion micromorphology of noble metal alloys and depletion gilding," Nature, vol. 282, pp. 597-598, Dec. 6, 1979.

Frechet, "Functional Polymers: from Plastic Electronics to Polymer-Assisted Therapeutics," Progress in Polymer Science, vol. 30, pp. 844-857, (2005).

Free Online Dictionary, "Aperture," definition, [first viewed Oct. 9, 2009].

Freitas et al., "Nimesulide PLA microsphere as a potential sustained release system for the treatment of inflammatory diseases," International Journal of Pharmaceutics, Vo. 295, pp. 201-211, (2005).

Freitas, "Nanomedicine, vol. I: Basic Capabilities," Landes Bioscience, pp. 87, 90, 255 and 265, (1999).

Friedrich et al., "Developing Interdisciplinary Undergraduate and Graduate Courses Through the Integration of Recent Research Results into the Curricula," (http://www.ineer.org/Events/ICEE1997/Proceedings/paper326.htm), 10 pages, [first downloaded Mar. 10, 2005.].

Fu et al., "Effects of mesh-assisted carbon plasma immersion ion implantation on the surface propoerties of insulating silicon carbide ceramics," Journal of Vacuum Science Technology, vol. A22, No. 2, pp. 356-360, Mar./Apr. 2004.

Fu et al., "Influence of thickness and dielectric properties on implantation efficacy in plasma immersion ion implantation of insulators," Journal of Applied Physics, vol. 95, No. 7, pp. 3319-3323, Apr. 1, 2004.

Fujisawa et al., "A novel textured surface for blood-contact," Biomaterials, vol. 20, pp. 955-962, (1999).

Fulton, "Ion-Assisted Filtered Cathodic Arc Deposition (IFCAD) System for Volume Production of Thin-Film Coatings," Society of Vacuum Coaters, 42nd Annual Technical Conference Proceedings, (1999).

Gabel et al., "Solid-State Spray Forming of Aluminum Near-Net Shapes," Journal of Metals, vol. 49, No. 8, pp. 31-33, (1997).

Gabel, "Low Temperature Metal Coating Method," Lawrence Livermore National Laboratory, p. 1-4, Apr. 3, 2000.

Gadegaard et al., "Tubes with Controllable Internal Nanotopography," Advanced Materials, vol. 16, No. 20, pp. 1857-1860, Oct. 18, 2004.

Galinski et al., "Ionic liquids as electrolytes," Electrochimica Acta, vol. 51, 5567-5580, (2006).

Gao, "Chemical Vapor Deposition," Handbook of Nanophase and Nanostructured Materials, vol. 1: Synthesis, Chapter 5, (2003).

Geretovszky et al., "Correlation of compositional and structural changes during pulsed laser deposition of tantalum oxide films," Thin Solid Films, vol. 453-454, pp. 245-250, (2004).

Gillanders et al., "A Composite Sol-Gel/Fluoropolymer Matrix for Dissolved Oxygen Optical Sensing," Journal of Photochemistry and Photobiology A: Chemistry, vol. 163, pp. 193-199, (2004).

Glocker et al., "AC Reactive Sputtering with Inverted Cylindrical Magnetrons," Society of Vacuum Coaters, 43rd Annual Technology Conference Proceedings—Denver, pp. 81-85, Apr. 15-20, 2000.

Glocker et al., "Recent developments in inverted cylindrical magnetron sputtering," PowerPoint presentation, pp. 1-21, (2001).

Glocker et al., "Recent developments in inverted cylindrical magnetron sputtering," Surface and Coatings Technology, vol. 146-147, pp. 457-462, (2001).

Goddard et al., "Polymer surface modification for the attachmend of bioactive compounds," Progress in Polymer Science, vol. 32, pp. 698-725, (2007).

Goh et al., "Nanostructuring Titania by Embossing with Polymer Molds Made from Anodic Alumina Templates," Nano Letters, vol. 5, No. 8, pp. 1545-1559, (2005).

Gollwitzer et al., "Titania Coating as Local "Drug" Delivery System with Antibacterial and Biocompatible Properties," 1 page, (2003).

Gong et al., "Controlled molecular release using nanopourous alumina capsules," Biomedical Microdevices, vol. 5, No. 1, pp. 75-80, Mar. 2003.

Gong et al., "Titanium oxide nanotube arrays prepared by anodic oxidation," Journal of Material Research, vol. 16, No. 12, pp. 3331-3334, (2001).

Goodison et al., "CD44 cell adhesion molecules," Journal of Clinical Pathology: Molecular Pathology, vol. 52, pp. 189-196, (1999).

Goodman et al., "Three-dimensional extracellular matrix textured biomaterials," Biomaterials, vol. 17, pp. 2087-295, (1996).

Gorb et al., "Biological microtribology: anisotropy in frictional forces of orthopteran attachment pads reflects the unitrastructure of a highly deformable material," Proceeding of the Royal Society, London series B, vol. 267, pp. 1239-1244, (2000).

Gotszalk et al., "Diagnostics of micro- and nanostructure using the scanning probe microscopy," Journal of Telecommunications and Information Technology, pp. 41-46, (2005).

Granqvist et al., "Biodegradable and bioactive hybrid organic-inorganic PEG-siloxane fibers: Preparation and Characterization," Colloid Polymer Science, vol. 282, pp. 495-501, (2004).

Greeley et al., "Electrochemical dissolution of surface alloys in acids: Thermodynamic trends from first-principles calculations," Electrochimica Acta, vol. 52, pp. 5829-5836, (2007).

Green et al., "XPS Characterisation of Surface Modified Ni-Ti Shape Memory Alloy," Materials Science and Engineering, vol. A224, pp. 21-26, (1997).

Gressel-Michel et al., "From a Microwave Flash-Synthesized TiO2 Colloidal Suspension to TiO2 Thin Films," Journal of Colloid and Interface Science, vol. 285, pp. 674-679, (2005).

Groth et al., "Layer-by-Layer Deposition of Polyelectrolytes—A Versatile Tool for the In Vivo Repair of Blood Vessels," Angewandte Chemie, International Edition, vol. 43, pp. 926-928, (2004).

Grubmuller, "What happens if the Room at the Bottom Runs Out? A Close Look at Small Water Pores," PNAS, vol. 100, No. 13, pp. 7421-7422, Jun. 24, 2003.

Gu et al., "Biomimetic titanium dioxide film with structural color and extremely stable hydrophilicity," Applied Physics Letters, vol. 85, No. 21, pp. 5067-5069 (2004).

Guangliang et al., "The effects of current density on the phase composition and microstructure properties of micro-arc oxidation coating," Journal of Alloys and Compounds, vol. 345, pp. 169-200, (2002).

Guo et al., "Formation of oxygen bubbles and its influence on current efficiency in micro-arc oxidation process of AZ91D magnesium alloy," Thin Solid Films, vol. 485, pp. 53-58, (2005).

Guo et al., "Growth of ceramic coatings on AZ91D magnesium alloys by micro-arc oxidation in aluminate-fluoride solutions and evalucation of corrosion resistance," Applied Surface Science, Col. 246, pp. 229-238, (2005).

Guo et al., "Investigation of corrosion behaviors of Mg-6Gd-3Y-0.4Zr alloy in NaCl aqueous solutions," Electrochimica Acta, vol. 52, pp. 2570-2579, (2007).

Guo et al., "Sol gel derived photocatalytic porous TiO2 thin films," Surface & Coatings Technology, vol. 198, pp. 24-29, (2005).

GVD Corporation, "Nanocoatings for a New Era," pp. 1-3, [first downloaded Nov. 12, 2003].

Haag et al., "Polymer Therapeutics: Concepts and Applications," Angewandte Chemie, vol. 45, pp. 1198-1215, (2006).

Haberland et al., "Filling of micron-sized contact holes with copper by energetic cluster impact," Journal of Vacuum Science Technology A, vol. 12, No. 5, pp. 2925-2930, Sep./Oct. 1994.

Haery et al., "Drug-eluting stents: The beginning of the end of restenosis?," Cleveland Clinic Journal of Medicine, vol. 71, No. 10, pp. 815-824, (2004).

Hahn et al., "A novel approach for the formation of Mg(OH)2/MgO nanowhiskers on magnesium: Rapid anodization in chloride containing solutions", Electrochemistry Communications, vol. 10, pp. 288-292, (2008).

Halme et al., "Spray Deposition and Compression of TiO2 Nanoparticle Films for Dye-Sensitized Solar Cells on Plastic Substrates," Solar Energy Materials & Solar Cells, vol. 90, pp. 887-899, (2006).

Hamley et al., "Nanostructure fabrication using block copolymers," Nanotechnology, vol. 14, pp. R39-R54, (2003).

Han et al., "Electron injection enhancement by diamond-like carbon film in organic electroluminescence devices," Thin Solid Films, vol. 420-421, pp. 190-194, (2002).

Han et al., "Pourous nanocrystalline titania films by plasma electrolytic oxidation," Surface and Coatings Technology, vol. 154, pp. 314-318, (2002).

Han et al., "Structure and in vitro bioactivity of titania-based films by micro-arc oxidation," Surface and Coatings Technology, vol. 168, pp. 249-258, (2003).

Han et al., "Synthesis of nanocrystalline titaniaa films by micro-arc oxidation," Materials Letters, vol. 56, pp. 744-747, (2002).

Hanley et al., "The growth and modification of materials via ion-surface processing," Surface Science, vol. 500, pp. 500-522, (2002).

Harris et al., "Fabrication of Perforated Thin Films with Helical and Chevron Pore Shapes," Electrochemical and Solid-State Letters, vol. 4, pp. C39-C42, (2004).

Harvard Nanopore, "Ion Beam Sculpting: Material Science—Fabricating Nanopores and Other Nanoscale Feature," pp. 1-5, [first downloaded Jul. 2, 2003], (http://www.mcb.harvard.edu.branton/projects-IonBeam/htm).

Hattori et al., "Photoreactivity of Sol-Gel TiO2 Films Formed on Soda-Lime Glass Substrates: Effect of SiO2 Underlayer Containing Fluorine," Langmuir, vol. 15, pp. 5422-5425, (1999).

Hau et al., "Surface-chemistry technology for microfluidics," Journal of Micromechanics and Microengineering, vol. 13, pp. 272-278, (2003).

Hausleiter et al., "Prvention of restenosis by a novel drug-eluting stent system with a dose-adjustable, polymer-free, on-site stent coating," European Heart Journal, vol. 26, pp. 1475-1481, (2005).

He et al., "Electrochemical Fabrication of Metal Nanowires," Encyclopedia of Nanoscience and Nanotechnology, vol. X, pp. 1-18, (2003).

He et al., "Optical properties of diamond-like carbon synthesized by plasma immersion ion processing," Journal of Vacuum Science Technology, vol. B17, No. 2, pp. 822-827, Mar./Apr. 1999.

Heidenau et al., "Structured Porous Titania as a Coating for Implant Materials," Key Eng Mater. vol. 192-195, pp. 87-90, (2001).

Heinig et al., "Modeling and Simulation of Ion Beam Sythesis of Nanoclusters," 6 pages, [first downloaded Jan. 3, 2000], (http://www.fz-rossendorf.de/pls/rois/Cms?pOId=10960&pFunc=Print&pLang=de).

Helmersson et al., "Ionized physical vapor deposition (IPVD): A review of technology and applications," Thin Solid Films, vol. 513, pp. 1-24, (2006).

Helmus et al. "Surface Analysis of a Series of Copolymers of L-Glutamic Acid and L-Leucine," Journal of Colloid and Interface Science, vol. 89, No. 2, pp. 567-570, (1982).

Helmus et al., "Plasma Interaction on Block Copolymers as Determined by Platelet Adhesion," Biomaterials: Interfacial Phenomena and Applications: Chapter 7, pp. 80-93, (1981).

Helmus et al., "The Effect of Surface Charge on Arterial Thrombosis," Journal of Biomedical Materials Research, vol. 18, pp. 165-183, (1984).

Hentze et al., "Porous polymers and resins for biotechnological and biomedical applications," Reviews in Molecular Biology, vol. 90, pp. 27-53, (2002).

Hoa et al., "Preparation of porous meterials with ordered hole structure," Advances in Colloid and Interface Science, vol. 121, pp. 9-23, (2006).

Hoffman, "Non-Fouling Surface Technologies," Journal of Biomaterials Science, Polymer Edition, vol. 10, No. 10, pp. 1011-1014, (1999).

Hoglund, "Controllable Degradation Product Migration From Biomedical Polyester-ethers," KTH Chemical Science and Engineering, Stockholm, pp. 1-52, May 24, 2007.

Holland et al., "Synthesis of Macroporous Minerals with Highly Ordered Three-Dimensional Arrays of Spheroidal Voids," Science, vol. 281, pp. 538-540, Jul. 24, 1998.

Hong et al., "The super-hydrophilicities of Bi-TiO2, V-TiO2, and Bi-V-TiO2 nano-sized particles and their benzene photodecompositions with H2O addition," Materials Letters, vol. 60, pp. 1296-1305, (2006).

Hopp et al., "Absorbing film assisted laser induced forward transfer of fungi (*Trichoderma conidia*)," Journal of Applied Physics, vol. 96, No. 6, pp. 3478-3481, Sep. 15, 2004.

Houbertz, "Laser interaction in sol-gel based materials - 3-D lithography for photonic applications," Applied Surface Science, vol. 247, pp. 504-512, (2005).

Houdayer et al., "Preparation of new antimony(0)/polyaniline nanocomposites by a one-pot solution phase method," Materials Letter, vol. 61, pp. 171-176, (2007).

Hrudey et al., "Organic Alq3 Nanostructures Fabricated with Glancing Angle Depostion," Vacuum Technology & Coating, pp. 1-6, May 2006.

Hsiao et al., "Soluble aromatic polyamides bearing asymmetrical diaryl ether groups," Polymer, vol. 45, pp. 7877-7885, (2004).

Hu et al., "Cyclic voltammetric deposition of hydrous ruthenium oxide for electrochemical capacitors: effects of codeposting iridium oxide," Electrochimica Acta, vol. 45, pp. 2684-2696, (2000).

Hu et al., "Voltammetric investigation of platinum oxides II. Efect of hydration on the reduction behavior," Electrochimica Acta, vol. 45, pp. 3063-3068, (2000).

Hüppauff et al., "Valency and Structure of Iridium in Anodic Iridium Oxide Films," Journal of Electrochemical Society, vol. 140, No. 3, pp. 598-602, Mar. 1993.

Hurley et al., "Nanopatterning of Alkynes on Hydrogen-Terminated Silicon Surfaces by Scanning Probe-Induced Cathodic Eletrografting," Journal of American Chemistry Society, vol. 125, pp. 11334-11339, (2003).

Hussain et al., "Atomic force microscope study of three-dimensional nanostructure sidewalls," Nanotechnology, vol. 18, pp. 1-8, (2007).

Ichinose et al., "A surface sol-gel process of TiO2 and other metal oxide films with molecular precision," Chem. Mater. vol. 9, pp. 1296-1298, (1997).

Ichinose et al., "Ultrathin composite films: An indispensable resource for nanotechnology ," Riken Review, No. 37, pp. 34-37, Jul. 2001.

Ignatova et al., "Combination of Electrografting and Aton-Transfer Radical Polymerization for Making the Stainless Steel Surface Antibacterial and Protein Antiadhesive," Langmuir, vol. 22, pp. 255-262, (2006).

Imai et al., "Preparation of Porous Anatase Coatings from Sol-Gel-Derived Titanium Dioxide and Titanium Dioxide-Silica by Water-Vapor Exposure," Journal of American Ceramics Society, vol. 82, No. 9, pp. 2301-2304, (1999).

Inflow Dynamics starts "LUSTY" Study, Company Press Release: First clinical trial with Niobium stents, (www.tctmd.com/industry-news/one.html?news_id=3364), 1 page, Jun. 25, 2002.

Inoue et al., "Corrosion rate of magnesium and its alloys in buffered chloride solutions," Corrosion Science, vol. 44, pp. 603-610, (2002).

Inovati, "Award Winning—Environmentally-Safe, High-Quality, Metal Spray Process," Press Release, pp. 1-6, (2002), (http://www.inovati.com/papers/KM-PressRelease.doc).

Inovati, "Inovati to Develop Green Metal Coating Technology" Press Release, 1 page, [first downloaded Sep. 1, 2005], (http://www.inovati.com/papers/bmdopr.html).

Inovati, "Low temperature, high-speed sprays make novel coatings," 1 pages, [first downloaded on Mar. 18, 2003], (http://www.inovati.com/papers/ampmar01.html).

Introduction to the Metal Printing Process: Future manufacturing equipment of advanced materials and complex geometrical shapes, (www.mpp.no/intro/intro.htm), pp. 1-2, downloaded Mar. 18, 2002.

Irhayem et al., "Glucose Detection Based on Electrochemically Formed Ir Oxide Films," Journal of Electroanalytical Chemisty, vol. 538-539, pp. 153-164, (2002).

Irvine et al., Nanoscale clustering of RGD peptides at surfaces using Comb polymers. 1. Synthesis and characterization of Comb thin films, Biomacromolecules, vol. 2, No. 1, pp. 85-94, Spring 2001.

Irvine et al., "Nanoscale clustering of RGD peptides at surfaces using comb polymers. 2. Surface segregation of comb polymers in polylactide," Biomacromolecules, vol. 2, No. 2, pp. 545-556, Summer 2001.

Ishizawa et al., "Characterization of thin hydroxyapatite layers formed on anodic titanium oxide films containing Ca and P by hydrothermal treatment," Journal of Biomedical Materials Research, vol. 29, pp. 1071-1079, (1995).

Ishizawa et al., "Histomorphometric evaluation of the thin hydroxyapatite layer formed through anodization followed by hydrothermal treatment," Journal of Biomedical Materials Research, vol. 35, pp. 199-206, (1997).

Isoflux Inc., "Isoflux specializes in vacuum coating equipment and coating process," http://www.isofluxinc.com/about.shtml, 1 page, Jul. 2009.

Iurhayem et al. "Glucose detection based on electrochemically formed Ir oxide films," Journal of Electroanalytical Chemistry, vol. 539-539, pp. 153-164, (2002).

Jensen et al., "Low-temperature preparation of nanocrystalline anatase films through a sol-gel rout," Journal of Sol-Gel Science and Technology, vol. 39, pp. 229-233, (2006).

Jewell et al., "Multilayered polyelectrolyte films promote the direct and localized delivery of DNA to cells," Journal of Controlled Release, vol. 106, pp. 214-223, (2005).

JMAR LLC, "Collimated Plasma Lithography (CPL)," 1 page, [first downloaded Jul. 2, 2003], (http://www.jmar.com/co451.html).

Johnson, "What's an Ionic Liquid?," The Electrochemical Society: Interface, pp. 38-41, Spring 2007.

Juodkazis et al., "Alternative view of anodic surface oxidation of nobel metals," Electrochimica Acta, vol. 51, pp. 6159-6164, (2006).

Kamei et al., "Hydrophobic drawings on hydrophilic surfaces of single crystalline titanium dioxide: surface wettability control by mechanochemical treatment," Surface Science Letters, vol. 463 pp. L609-L612, (2000).

Kanda et al., "Characterization of Hard Diamond-Like Carbon Films Formed by Ar Gas Cluster Ion Beam-Assisted Fullerene Deposition," Japanese Journal of Applied Physics, vol. 41, Part 1, No. 6B, pp. 4295-4298, Jun. 2002.

Kang et al., "Controlled drug release using nanoporous anodic aluminum oxide on stent," Thin Solid Films, vol. 515, pp. 5184-5187, (2007).

Kaplan, "Cold Gass Plasma and Silanes," Presented at the 4th International Symposium on Silanes and Other Coupling Agents, Jul. 11-13, 2003.

Karuppuchamy et al., "Cathodic Electrodeposition of Oxide Semiconductor Thin Films and their Application to Dye-Sensitized Solar Cells," Solid State Ionics, vol. 151, pp. 19-27, (2002).

Karuppuchamy et al., "Photoinduced Hydrophilicity of Titanium Dioxide Thin Films Prepared by Cathodic Electrode position," Vacuum, vol. 80, pp. 494-498, (2006).

Karuppuchamy et al., "Super-hydrophilic amorphous titanium dioxide thin film deposited by cathodic electrodeposition," Materials Chemisty and Physics, vol. 93, pp. 251-254, (2005).

Karuri et al., "Biological length scale topography enhances cell-substratum adhesion of human corneal epithelial cells," Journal of Cell Science, vol. 117, No. 15, pp. 3153-3164, (2004).

Kasemo et al., "Implant surfaces and interface processes," Adv. Dent. Res. vol. 13, pp. 8-20 Jun. 1999.

Kasemo, "Biological surface science," Surface Science, vol. 500, pp. 656-677, (2002).

Kato et al., "N-succinyl-chitosan as a drug carrier: water-insoluble and water-soluble conjugates," Biomaterials, vol. 25, pp. 907-915, (2004).

Katsumata et at., "Effect of Microstructure on Photoinduced Hydrophilicity of Transparent Anatase Thin Films," Surface Science, vol. 579, pp. 123-130, (2005).

Katz, "Developments in Medical Polymers for Biomaterials Applications," Medical Device Link, pp. 1-9, Jan. 2001, (http://www.devicelink.com/mddi/archive/01/01/003.html).

Kean et al. "The Analysis of Coatings Produced by Accelerated Nanoparticles," Mantis Deposition Ltd., Presentaction at NSTI Nano Tech 2006, Boston, May 7th-11th, pp. 1-4, 2006.

Kesapragada et al., "Two-component nanopillar arrays grown by Glancing Angle Deposition," Thin Solid Films, vol. 494, pp. 234-239, (2006).

Kesler et al., "Enhanced Strength of Endothelial Attachment on Polyester Elastomer and Polytetrafluoroethylene graft Surfaces with Fibronectin Substrate," Journal of Vascular Surgery, vol. 3, No. 1, pp. 58-64, (1986).

Kesting, "Synthetic Polymeric Membranes—A Structural Perspective", Chapters 6-7, pp. 225-286, Oct. 1985.

Kickelbick, "Concepts for the incorporation of inorganic building blocks into organic polymers on a nanoscale," Progress in Polymer Science, vol. 28, pp. 81-114, (2003).

Kidambi et al., "Selective Depositions on Polyelectrolyte Multilayers: Self-Assembled Monolayers on m-dPEG Acid as Molecular Template," Journal of the American Chemistry Society, vol. 82, No. 9, pp. 4697-4703, (2004).

Kilian et al., "Plasma transglutaminase factor XIII induces microvessel ingrowth into biodegradable hydroxyapatite implants in rats," Biomaterials, vol. 26, pp. 1819-1827, (2005).

Kim et al. "Porous ZrO2 bone scaffold coated with hydroxyapatite with fluorapatite intermediate layer," Biomaterials, vol. 24, pp. 3277-3284, (2003).

Kim et al., "Adhesion of RF bias-sputtered Cr thin films onto photosensitivepolyimide substrates," IEEE, International Symposium on Eelectrical Materials and Pakaging, pp. 202-207, (2001).

Kim et al., "Fabrication of WC-Co coatings by cold spray deposition," Surface & Coatings Technology, vol. 191, pp. 335-340, (2005).

Kim et al., "Hollow Silica Spheres of Controlled Size and Porosity by Sol-Gel Processing," Journal of Americal Ceramic Society, vol. 74, Nol. 8, pp. 1987-1992, (1991).

Kim et al., "Proton conducting polydimethylsiloxane/metal oxide hybrid membranes added with phosphotungstic acid(II)," Electrochimica Acta, vol. 49, pp. 3429-3433, (2004).

Kim et al., "Fabrication and Characterization of TiO2 Thin Film Prepared by a Layer-By-Layer Self-Assembly Method," Thin Solid Films, vol. 499, pp. 83-89, (2006).

Kitagawa et al., "Near-Edge X-Ray Absorption Fine Structure Study for Optimization of Hard Diamond-Like Carbon Film Formation with Ar Cluster Ion Beam," Japanese Journal of Applied Physics, vol. 42, pp. 3971-3975, (2003).

Kitagawa et al., Optimum Incident Angle of Ar Cluster Ion Beam for Superhard Carbon Film Deposition, Japanese Journal of Applied Physics, vol. 43, No. 6B, pp. 3955-3958, (2004).

Kittaka et al., "The Structure of Water Monolayers on a Hydroxylated Chromium Oxide Surface," Adsorption, vol. 11, pp. 103-107, (2005).

Kleinertz et al., "LUSTY Studie: Lunar STF Study," PowerPoint presentation, pp. 1-24, Sep. 4, 2004.

Kleisner et al., "A system based on metal alkyl species that forms chemically bound organic overlays on hydroxylated planar surfaces," Thin Solid Films, vol. 381, pp. 10-14, (2001).

Kogure et al., "Microstructure of nemalite, fibrous iron-bearing brucite", Mineralogical Journal, vol. 20, No. 3, pp. 127-133, Jul. 1998.

Kohli et al., "Arrays of lipid bilayers and liposomes on patterned polyelectrolyte templates," Journal of Colloid and Interface Science, vol. 301, pp. 461-469, (2006).

Kokubo et al., "Novel bioactive materials with different mechanical properties," Biomaterials, vol. 24, pp. 2161-2175, (2003).

Kommireddy et al., "Layer-by-Layer Assembly of TiO2 Nanoparticles for Stable Hydrophilic Biocompatible Coatings" Journal of Nanoscience and Nanotechnology, vol. 5, pp. 1081-1087, (2005).

Kondyurin et al., "Plasma Immersion ion implantation of polyethylene," Vacuum, vol. 64, pp. 105-111, (2002).

Kong et al., "Polyelectrolyte-functionalized multiwalled carbon nanotubes: preparation, characterization and layer-by-layer self-assembly," Polymer, vol. 46, pp. 2472-2485, (2005).

Konig et al., "Nanoprocessing with nanojoule near-infrared femtosecond laser pulses," Medical Laser Application, vol. 20, pp. 169-184, (2005).

Konishi et al., "Morphology Control of Dy-Ni Alloy Films by Electrochemical Displantation," Electrochemical and Solid-State Letters, vol. 5, No. 12, pp. B37-B39, (2002).

Koo et al., "Co-regulation of cell adhesion by nanoscale RGD organization and mechanical stimulus," Journal of Cellular Science, vol. 115, Part 7, pp. 1423-1433, Apr. 1, 2002.

Kopanski et al., "Scanning Kelvin Force Microscopy For Characterizing Nanostructures in Atmosphere," Characterization and Metrology for Nanoelectronics: 2007 International Conference on Frontiers of Characterization and Metrology. American Institute of Physics Conference Proceedings, vol. 931, pp. 530-534, Septem 26, 2007.

Kostov et al., "Two Dimensional Computer Simulation of Plasma Immersion Ion Implantation," Brazilian Journal of Physics, vol. 34, No. 4B, pp. 1689-1695, Dec. 2004.

Kötz et al., "XPS Studies of Oxygen Evolution on Ruand RuO2 Anodes," Journal of Electrochemical Society: Electrochemical Science and Technology, pp. 825-829, Apr. 1983.

Kowalski et al., "Corrosion protection of steel by bi-layered polypyrrole doped with molybdophosphate and naphthalenedisulfonate anions," Corrosion Science, Vo. 49, pp. 1635-1644, ( 2007).

Kraft et al., "Thin films from fast clusters: golden TiN layers on a room temperature substrate" Surface and Coatings Technology 158-159, pp. 131-135, (2002).

Krumeich et al., "HyFraSurf-Advanced Surface Technology for Superior Electrode Performance," European Cells and Materials, vol. 1, Suppl. 1, p. 43, (2001).

Kumar et al., "Influence of electric field type on the assembly of single walled carbon nanotubes," Chemical Physics Letters, vol. 383, pp. 235-239, (2004).

Kumar et al., "Polyanhydrides: an overview," Advanced Drug Delivery Reviews, vol. 54, pp. 889-910, (2002).

Kunitake et al., "Molecular imprinting in ultrathin titania gel films via surface sol-gel process," Analytica Chimica Acta, vol. 504, pp. 1-6, (2004).

Kurth et al., "Multilayers on Solid Planar Substrates: From Structure to Function," Multilayer Thin Films: Sequential Assembly of Nanocomposite Materials, Chapter 14, pp. 393-426, Mar. 7, 2003.

Kutsenko et al., "Structural changes in Mg alloy induced by plasma immersion ion implantation of Ag," Acta Materialia, vol. 52, pp. 4329-4335, (2004).

Kutz, "Biomaterials to Promote Tissue Regeneration," in Standard Handbook of Biomedical Engineering and Design, ISBN 0-07-135637-1, pp. 16.13-16.29, (2003).

Kvastek et al., "Electochemical properties of hydrous rithenium oxide films formed and measured at different potentials," Journal of Electroanalytical Chemistry, vol. 511, pp. 65-78, (2001).

Lakard et al., "Adhesion and proliferation of cells on new polymers modified biomaterials," Bioelectrochemistry, vol. 62, pp. 19-27, (2004).

Lakatos-Varsanyi et al., "Cyclic voltammetry measurements of different single-, bi- and multilayer TiN and single layer CrN coatings on low-carbon-steel substrates," Corrosion Science, vol. 41, pp. 1585-1598, (1999).

Lamaka et al., "TiOx self-assembled networks prepared by templating approach as nanostructured reservoirs for self-healing anticorrosion pre-treatments," Electrochemistry Comunications, vol. 8, pp. 421-428, (2006).

Larner et al., "The Challenge of Plasma Processing—Its Diversity," Presented at the ASM Materials and Processes for Medical Devices Conference, Aug. 25-27, 2004.

Laser-Induced Forward Transfer (LIFT): Paul Scherrer Institut, (http://materials.web.psi.ch/Research/Thin_Films/Methods/Lift.htm), pp. 1-2, downloaded Dec. 7, 2006.

Lau et al., "Hot-wire chemical vapor deposition (HWCVD) of fluorocarbon and organosilicon thin films," Thin Solid Films, vol. 395, pp. 288-291, (2001).

LaVan et al., Small-scale systems for in vivo drug delivery, Nature Biotechnology, vol. 21, No. 10, pp. 1184-1191, Oct. 2003.

Leary-Swan et al., "Fabrication and evaluation of nanoporous alumina membranes for osteoblast culture," Journal of Biomedical Materials Research: Part A, vol. 72A, pp. 288-295, (2005).

Lee et al., "A Template-Based Electrochemical Method for the Synthesis of Multisegmented Metallic Nanotubes," Angewandte Chemie, vol. 44, pp. 6050-6054, (2005).

Lee et al., "Biocompatibility and Charge Injection Property of Iridium Film Formed by Ion Beam Assisted Deposition," Biomaterials, vol. 24, pp. 2225-2231, (2003).

Lee et al., "Structural characterization of porous low-k thin films prepared by different techniques using x-ray porosimetry," Journal of Applied Physics, vol. 95, No. 5, Mar. 1, 2004.

Lee et al., "A study on electrophoretic deposition of Ni nanoparticles on pitted Ni alloy 600 with surface fractality", Journal of Colloid and Interface Science, vol. 308, pp. 413-420, (2007).

Lefaux et al., "Polyelectrolyte Spin Assembly: Influence of Ionic Strenght on the Growth of Multilayered Thin Films," Journal of Polymer Science Part B: Polymer Physics, vol. 42, pp. 3654-3666, (2004).

Lei et al., "Fabrication of Highly Ordered Nanoparticle Arrays Using Thin Porous Alumina Masks," Advanced Materials for Micro- and Nano-Systems (Ammns), pp. 1-6, Jan. 2001.

Leng et al., "Mechanical properties and platelet adhesion behavior of diamond-like carbon films synthesized by pulsed vacuum arc plasma deposition," Surface Science, vol. 531, pp. 177-184, (2003).

Lenza et al., "In vitro release kinetics of proteins from bioactive foams," Journal of Biomedical Materials Research: A, vol. 67, No. 1, pp. 121-129, Oct. 2003.

Leoni et al., "Characterization of Nanoporous Membranes for immunoisolation: Diffusion Properties and Tissue Effects," Biomedical Microdevices, vol. 4, No. 2, pp. 131-139, (2002).

Leoni et al., "Nanoporous Platforms for Cellular Sensing and Delivery," Sensors, 51(2), pp. 111-120, (2002).

Leung et al., "Fabrication of photonic band gap crystal using microtransfer molded templates," Journal of Applied Physics, vol. 93, No. 10, pp. 5866-5870, May 15, 2003.

Lewis et al., "Silicon nonopillars formed with gold colloidal partical masking," Journal of Vacuum Science Technology B, vol. 16, No. 6, pp. 2938-2941, Nov./Dec. 1998.

Li et al., "A simple approach to fabricate amorphous silicon pattern on single crystal silicon," Tribology International, vol. 40, pp. 360-364, (2007).

Li et al., "Bioactive Hydroxyapatite Composite Coating Prepared by SOL-Gel Process," Journal of Sol-Gel Science and Technology, vol. 7, pp. 27-34, (1996).

Li et al., "Fabrication and Microstructuring of Hexagonally Ordered Two-Dimensional Nanopore Arrays in Anodic Alumina," Advanced Materials, vol. 11, pp. 483-487, (1999).

Li et al., "Hexagonal pore arrays with a 50-420 nm interpore distance formed by self-organization in anodic alumina," Journal of Applied Physics, vol. 84, No. 11, pp. 6023-6026, Dec. 1, 1998.

Li et al., "Improved biological performance of Ti implants due to surface modification by micro-arc oxidation," Biomaterials, vol. 25, pp. 2867-2875, (2004).

Li et al., "On the growth of highly ordered pores in anodized aluminum oxide," Chem. Mater., vol. 10, pp. 2470-2480, (1999).

Li et al., "pH-compensation effect of bioactive inorganic fillers on the degradation of PLGA," Composites Science and Technology, vol. 65, pp. 2226-2232, (2005).

Li et al., "Polycrystalline nanopore arrays with haxagonal ordering on aluminum," Journal of Vacuum Science Technology: A, vol. 17, pp. 1428-1431, (1999).

Li et al., "A novel method for preparing surface-modified Mg(OH)2 nanocrystallines," Materials Science and Engineering A, 452-453, pp. 302-305, (2007).

Li, "Poly(L-glutamic acid)-anticancer drug conjugates," Advanced Drug Delivery Reviews, vol. 54, pp. 695-713, (2002).
Liaw et al., "Process Monitoring of Plasma Electrolytic Oxidation," presented at the 16th World Conference on Nondestructive Testing, Montreal, Canada, pp. 1-7, Aug. 30-Sep. 3, 2004.
Liebling et al., "Optical Properties of Fibrous Brucite from Asbestos, Quebec", American Mineralogist, vol. 57, pp. 857-864, (1972).
Lim et al., "Systematic variation in osteoblast adheasion and phenotype with substratum surface characteristics," Journal of Biomedical Materials and Research, vol. 68A, No. 3, pp. 504-511, (2004).
Lim et al., "UV-Driven Reversible Switching of a Roselike Vanadium Oxide Film between Superhydrophobicity and Superhydrophilicity," Journal of American Chemical Society, vol. 129, pp. 4126-4129, Mar. 15, 2007.
Lin et al., "PWA-doped PEG/SiO2 proton-conducting hybrid membranes for fuel cell applications," Journal of Membrane Science, vol. 254, pp. 197-205, (2005).
Lindstrom et al., "A New Method for Manufacturing Nanostructured Electrodes on Glass Substrates," Solar Energy Materials & Solar Cells, vol. 73, pp. 91-101 (2002).
Lippert et al., "Chemical and Spectroscopic Aspects of Polymer Ablation: Special Features and Novel Directions," Chemical Reviews, vol. 103, pp. 453-485, (2003).
Liu et al., "A metal plasma source ion implantation and deposition system," American Institute of Physics, Review of Scientific Instruments, vol. 70, No. 3, pp. 1816-1820, Mar. 1999.
Liu et al., "Electrodeposition of Polypyrrole Films on Aluminum from Tartrate Aqueous Solution," Journal of Brazilian Chemical Society, vol. 18, No. 1, pp. 143-152, (2007).
Liu et al., "Surface modification of titanium, titanium alloys, and related materials for biomedical applications," Materials Science and Engineering R, vol. 47, pp. 49-121, (2004).
Lu et al., "Fabricating Conducting Polymer Electrochromic Devices Using Ionic Liquids," Journal of The Electrochemical Society, vol. 151, No. 2, pp. H33-H39, (2004).
Lu et al., "Micro and nano-fabrication of biodegradable polymers for drug delivery," Advanced Drug Delivery Reviews, vol. 56, pp. 1621-1633, (2004).
Lv et al., "Controlled growth of three morphological structures of magnesium hydroxide nanoparticles by wet precipitation method," Journal of Crystal Growth, vol. 267, pp. 676-684, (2004).
Lv et al., "Controlled synthesis of magnesium hydroxide nanoparticles with different morphological structures and related properties in flame retardant ethyolene-vinyl acetate blends", Nanotechnology, vol. 15, pp. 1576-1581, (2004).
Lv et al., "In situ synthesis of nanolamellas of hydrophobic magnesium hydroxide", Colloids and Surfaces A: Physicochemical and Engineering Aspects, vol. 296, pp. 97-103, (2007).
Maeda et al., "Effect of Silica Addition on Crystallinity and Photo-Induced Hydrophilicity of Titania-Silica Mixed Films Prepared by Sol-Gel Process," Thin Solid Films, vol. 483, pp. 102-106, (2005).
Maehara et al., "Buildup of Multilayer Structures of Organic-Inorganic Hybrid Ultra Thin Films by Wet Process," Thin Solid Films, vol. 438-439, pp. 65-69, (2003).
Maheshwari et al., "Cell adhesion and motility depend on nanoscale RGD clustering," Journal of Cell Science, vol. 113, Part 10, pp. 1677-1686, May 2000.
Maitz et al., "Blood Compatibility of Titanium Oxides with Various Crystal Structure and Element Doping," Journal of Biomaterials Applications, vol. 17, pp. 303-319, Apr. 2003.
Manna et al., "Microstructural Evalution of Laser Surface Alloying of Titanium with Iridium," Scripta Materialia, vol. 37, No. 5, pp. 561-568, (1997).
Manoharan et al., "Ordered macroporous rutile titanium dioxide by emulsion templating," Proceedings of SPIE, vol. 3937, pp. 44-50, (2000).
Mantis Deposition Ltd., "Nanocluster Deposition," Thame, Oxforshire, United Kingdom, pp. 1-2, [downloaded on Feb. 2, 2007], (http://www.mantisdeposition.com/nanocluster.html).
Martin et al., "Microfabricated Drug Delivery Systems: Concepts to Improve Clinical Benefit," Biomedical Microdevices, vol. 3, No. 2, pp. 97-107, Jun. 2001.

Martin, "Pulsed Laser Deposition and Plasma Plume Investigations," Andor Technology, Ltd. pp. 1-3, (2003).
Masuda et al., "Highly ordered nanochannel-array architecture in anodic alumina," Applied Physics Letters, vol. 71, pp. 2770-2772, (1997).
MatijeviO, "Colloid Chemical Aspects of Corrosion of Metals", Pure & Applied Chemisty, vol. 52, pp. 1179-1193, (1980).
Mattox, "Introduction: Physical Vapor Deposition (PVD) Processes," Vacuum Technology & Coating, pp. 60-63, Jul. 2002.
Mattox, "The History of Vacuum Coating Technology: Part V," Vacuum Technology & Coating, pp. 32-37, Oct. 2002.
Mattox, "The History of Vacuum Coating Technology: Part VI," Vacuum Technology & Coating, pp. 52-59, Oct. 2002.
Mauritz Group Homepage, "Sol-Gel Chemistry and Technology," (htty://www.psrc.usin.edu/mauritz/solgel.html), pp. 1-10, (downloaded [2006]).
McGuigan et al., "The influence of biomaterials on endothelial cell thrombogenicity," Biomaterials, vol. 28, pp. 2547-2571, (2007).
McNally et at., "Cathodic Electrodeposition of Cobalt Oxide Films Using Polyelectrolytes," Materials Chemistry and Physics, vol. 91, pp. 391-398, (2005).
Meijer et al., "Laser Machining by short and ultrashort pulses, state of the art and new opportunities in the age of the photons," Annals of CIRP 2002: Manufacturing Technology, vol. 51, No. 2, pp. 531-550, (2002).
Meletis et al., "Electrolytic plasma processing for cleaning and metal-coating of steel surfaces," Surface and Coatings Technology, vol. 150, pp. 246-256, (2002).
Merriam-Webster's Dictionary Website: For definition of Strut, 1 page,[first cited Jul. 21, 2010], (http://www.merriam-webster.com/dictionary/strut).
MicroFab Technologies Inc. "MicroFab: Biomedical Applications—Stents," pp. 1-4, [first downloaded Mar. 23, 2007], (http://www.microfab.com/technology/biomedical/Stents.html).
Mikhaylova et al., "Nanowire formation by electrodeposition in modified nanoporous polycrystalline anodic alumina templates," Mat. Res. Soc. Symp. Proc., vol. 704, pp. w6.34.1-W6.34.6, (2002).
Miller et al., "Endothelial and vascular smooth muscle cell function on poly(lactic-co-glycolic acid) with nano-structured surface features," Biomaterials, vol. 25, No. 1, pp. 53-61, (2004).
Miller et al., "Mechanism(s) of increased vascular cell adhesion on nanostructured poly(lactic-coglycolic acid) films," Journal of Biomedical Materials Research A, vol. 73, No. 4, pp. 476-484, (2005).
Miv Therapeutics, "Hydroxyapatite Coating," pp. 1-4, [first downloaded Jun. 25, 2003], (http://www.mivtherapeutics.com/technology/hap/).
Mobedi et al., "Studying the Degradation of Poly(L-lactide) in Presence of Magnesium Hydroxide", Iranian Polymer Journal, vol. 15, No. 1, pp. 31-39, (2006).
Mu et al., "A novel controlled release formulation for the anticancer drug paclitaxel (Taxol): PLGA nanoparticles containing vitamin E TPGS," Journal of Controlled Release, vol. 86, pp. 33-48, (2003).
Mu et al., "Vitamin E TPGS used as emulsifier in the solvent evaporation/extraction technique for fabrication of polymeric nanospheres O for controlled release of paclitaxel (Taxol)", Journal of Controlled Release, vol. 80, pp. 129-144, (2002).
Muller et al., "Solid lipid nanoparticles (SLN) for controlled drug delivery: a review of the state of the art," European Journal of Pharmaceutics and Biopharmaceutics, vol. 50, pp. 161-177, (2000).
Munchow et al., "Poly[(oligoethylene glycol) Dihydroxytitanate] as Organic-Inorganic Polymer-Electrolytes," Electrochimica Acta, vol. 45, pp. 1211-1221, (2000).
Murray et al., "Electrosynthesis of novel photochemically active inherently conducting polymers using an ionic liquid electrolyte," Electrochimica Acta, vol. 51, pp. 2471-2476, (2006).
Naganuma et al., "Preparation of Sol-Gel Derived Titanium Oxide Thin Films Using Vacuum Ultraviolet irradiation with a Xenon Excimer Lamp," Japanese Journal of Applied Physics, vol. 43, No. 9A, pp. 6315-6318, (2004).
Nair et al., "Biodegradable polymers as biomaterials", Progress in Polymer Science, vol. 32, pp. 732-798, (2007).

Nakajima et al., "Effect of Vacuum Ultraviolet Light Illumination on the Crystallization of Sol-Gel-Derived Titanium Dioxide Precursor Films," Surface & Coatings Technology, vol. 192, pp. 112-116, (2005).

Nakayama et al., "Fabrication of drug-eluting covered stents with micropores and differential coating of heparin and FK506," Cardiovascular Radiation Medicine, vol. 4, pp. 77-82, (2003).

NanoBiotech News, vol. 2, No. 26, pp. 1-9, Jun. 30, 2004.

Nanoparticle coatings: Application note, "Antimicrobial Coatings," MANTIS Deposition Ltd, pp. 1-2, (2006).

Nanu, "Nanostructured TiO2-CuInS2 based solar cells," Symposium D, Thin Film and Nano-Structured Materials for Photovoltaics, E-MRS Spring Meeting 2003, pp. 1-2, Jun. 10-13, 2003.

NASA Glenn Research Center, "Fast Three-Dimensional Method of Modeling Atomic Oxygen Undercutting of Protected Polymers," pp. 1-6, [first downloaded on Jul. 3, 2003], (http://www.grc.nasa.gov/WWW/epbranch/suurtxt/surfaceabs.htm).

Neves et al., "The morphology, mechanical properties and ageing behavior of porous injection molded starch-based blends for tissue engineering scafolding," Materials Science and Engineering, vol. C25, pp. 195-200, (2005).

Newman et al., "Alloy Corrosion," MRS Bulletin, pp. 24-28, Jul. 1999.

Ngaruiya et al., "Structure formation upon reactive direct current magnetron sputtering of transition metal oxide films," Applied Physics Letters, vol. 85, No. 5, pp. 748-750, Aug. 2, 2004.

Ngaruiya et al., "The reactive DC-Magnetron Sputtering Process,", pp. 1-5, (circa 2004).

Nicoll et al., "In vitro release kinetics of biologically active transforming growth factor-beta 1 from a novel porous glass carrier," Biomaterials, vol. 18, Issue 12, pp. 853-859, (1997).

Nicoll et al., "Nanotechnology and Biomaterials - Drugs, Drug Delivery Systems, Quantum Dots and Disease Treatment," Azom.com, pp. 1-5, [first downloaded Mar. 22, 2004], (http://www.azom.com/details.asp?ArticleID=1853).

Nie et al., "Deposition of layered bioceramic hydroxyapatite/TiO2 coatings on titanium alloys using a hybrid technique of micro-arc oxidation and electrophoresis," Surface Coatings Technology, vol. 125, pp. 407-414, (2000).

Nishio et al., "Preparation and properties of electrochromic iridium oxide thin film by sol-gel process," Thin Solid Films, vol. 350, pp. 96-100, (1999).

Noguera et al., "3D fine scale ceramic components formed by ink-jet prototyping process," Journal of the European Ceramic Society, vol. 25, pp. 2055-2059, (2005).

O'Brien et al., "Passivation of Nitinol Wire for Vascular Implants-A Demonstration of the Benefits," Biomaterials, vol. 23, pp. 1739-1748, (2002).

Oh et al., "Microstructural characterization of biomedical titanium oxide film fabricated by electrochemical method," Surface & Coatings Technology, vol. 198, pp. 247-252, (2005).

Orloff et al., "Biodegradable implant strategies for inhibition of restenosis," Advanced Drug Delivery Reviews, vol. 24, pp. 3-9, (1997).

Oxford Applied Research, "Nanocluster Deposition Systems—Nanodep60," 1 page, [first downloaded Nov. 3, 2006], (http://www.oaresearch.co.uk.nanodep60.htm).

Paik et al., "Micromachining of mesoporous oxide films for microelectromechanical system structures," Journal of Materials Research, vol. 17, pp. 2121-2129, (2002).

Palasis et al., "Analysis of Adenoviral Transport Mechanisms in the Vessel Wall and Optimization of Gene Transfer Using Local Delivery Catheters," Human Gene Therapy, vol. 11, pp. 237-246, Jan. 20, 2000.

Palasis et al., "Site-Specific Drug Delivery from Hydrogel Coated Angioplasty Catheters," Proceedings of the International Symposium on Controlled Release: Bioactive Materials, vol. 24, pp. 825-826, (1997).

Palmaz et al., "Influence of surface topography on endothelialization of intravascular metallic material," Journal of Vascular and Interventional Radiology, vol. 10, No. 4, pp. 439-444, (1999).

Pang et al., "Electrodeposition of composite hydroxyapatite-chitosan films," Materials Chemistry and Physics, vol. 94, pp. 245-251, (2005).

Pang et al., "Electropolymerization of high quality electrochromic poly(3-alkyl-thiophene)s via a room termperature ionic liquid," Electrochimica Acta, vol. 52, pp. 6172-6177, (2007).

Park et al., "Multilayer Transfer Printing for Polyelectrolyte Multilayer Patterning. Direct Transfer of Layer-by-Layer Assembled Micropatterned Thin Films," Advanced Materials, vol. 16, No. 6, pp. 520-525, Mar. 18, 2004.

Park et al., "Novel Phenylethynyl Imide Silanes as Coupling Agents for Titanium Alloy," The 22nd Annual Meeting of the Adhesion Society, pp. 1-5, Feb. 21-24, 1999.

Park et al., "Cathodic electrodeposition of RuO2 thin films from Ru(III)C13 solution", Materials Chemistry and Physics, vol. 87, pp. 59-66, (2004).

Park et al., "Microstructural change and precipitation hardeningin melt-spun Mg-X-Ca alloys," Science and Technology of Advanced Materials, vol. 2, pp. 73-78, (2001).

Pathan et al., "A chemical route to room-temperature synthesis of nanocrystalline TiO2 thin films," Applied Surface Science, vol. 246, pp. 72-76, (2005).

Pelletier et al., "Plasma-based ion implantation and deposition: A review for physics, technology, and applications," Lawrence Berkeley and National Laboratory, pp. 1-68, May 16, 2005.

Peng et al., "Role of polymers in improving the results of stenting in coronary arteries," Biomaterials, vol. 17, No. 7, pp. 658-694 (1996).

Perlman et al., "Evidence for rapid onset of apoptosis in medial smooth muscle cells after balloon injury," Circulation, vol. 95, No. 4, pp. 981-987, Feb. 18, 1997.

Pharmaceutical Science Technology, Chapter 6: Electropolymerization, pp. 24-28, (2007).

Piazza et al., "Protective diamond-like carbon coatings for future optical storage disks," Diamond & Related Materials, vol. 14, pp. 994-999, (2005).

Pitt et al., "Attachment of hyaluronan to metallic surfaces," Journal of Biomedical Materials Research, vol. 68A, pp. 95-106, (2004).

Polygenetics, "Advanaced Drug Delivery," [first downloaded on May 4, 2007], 5 pages, (http://www.polygenetics.com/drug_delivery.htm).

Ponte et al., "Porosity determination of nickel coatings on copper by anodic voltammetry," Journal of Applied Electrochemistry, vol. 32, pp. 641-646, (2002).

Prior Clinicals, Boston Scientific memo, pp. 1-2, (more than a year prior to May 23, 2007).

Prokopowicz et al., "Synthesis and Application of Doxorubicin-Loaded Silica Gels as Solid Materials for Spectral Analysis," Talanta, vol. 65, pp. 663-671, (2005).

Prokopowicz et al., "Utilization of Standards Generated in the Process of Thermal Decomposition Chemically Modified Silica Gel or a Single Point Calibration of a GC/FID System," Talanta, vol. 44, pp. 1551-1561, (1997).

Pulsed Laser Deposition, (http://www.physandtech.net), pp. 1-7, Apr. 28, 2001.

PVD Materials—Materials Available for Physical Vapour Deposition (PVD) from Williams Advanced Materials. (www.azom.com), pp. 1-8, [first downloaded Apr. 28, 2006].

Qasem et al., "Kinetics of Paclitaxel 2'-N-Methylpyridinium Mesylate Decomposition," AAPS PharmaSciTech, vol. 4, No. 2, Article 21, pp. 1-8, (2003).

Qian et al., "Preparation, characterization and enzyme inhibition of methylmethacrylate copolymer nanoparticles with different hydrophilic polymeric chains," European Polyer Journal, vol. 42, pp. 1653-1661, (2006).

Qiang et al., "Hard coatings (TiN, Ti$\chi$All-$\chi$N) deposited at room temperature by energetic cluster impact," Surface and Coatings Technology, 100-101, pp. 27-32, (1998).

Qiu et al., "Self-assembled growth of MgO nanosheet arrays via a micro-arc oxidations technique," Applied Surface Science vol. 253, pp. 3987-3990, (2007).

Radin et al., "Biocompatible and Resorbable Silica Xerogel as a Long-Term Controlled Release Carrier of Vancomycin," Orthopaedic Research Society, 47th Annual Meeting, Feb. 25-28, 2001, San Francisco, CA.

Radin et al., "Silica sol-gel for the controlled release of antibiotics. I. Synthesis, characterization, and in vitro release," Journal of Biomedical Materials Research, vol. 27, No. 2, pp. 313-320, Nov. 2001.

Radin, S. et al., "In vitro bioactivity and degradation behavior of silica xerogels intended as controlled release materials," Biomaterials. vol. 23, No. 15, pp. 3113-3122, Aug. 2002.

Radtchenko et al., "A Novel Method for Encapsulation of Poorly Water-Soluble Drugs: precipitation in Polyelectrolyte multilayer shells", International Journal of Pharmaceutics, vol. 242, pp. 219-223, (2002).

Razzacki et al., "Integrated microsystems for controlled drug delivery," Advanced Drug Delivery Reviews, vol. 56, pp. 185-198, (2004).

Rees et al., "Glycoproteins in the Recognition of Substratum by Cultured Fibroblasts," Symposia of the Society for Experimental Biology: Cell-Cell Recognition, No. 32, pp. 241-260 (1978).

Reyna-Gonzales et al., "Influence of the acidity level on the electropolymerization of N-vinylcarbazole: Electrochemical study and characterization of poly(3,6-N-vinylcarbazole)," Polymer, vol. 47, pp. 6664-6672, (2006).

Rice, "Limitations of pore-stress concentrations on the mechanical properties of porous materials," Journal of Material Science, vol. 32, pp. 4731-4736, (1997).

Ristoscu, "Thin Films and Nanostructured Materials." pp. 1-2, [first downloaded Jul. 3, 2003], (http://www..fisica.unile.it/radiazioni/ThinY02Ofilms%20and%2Onanostmctured%20materials.htm).

Robbie et al., "Advanced techniques for glancing angle deposition," Journal of Vacuum Science and Technology B, vol. 16, No. 3, pp. 1115-1122, (May/Jun. 1998).

Robbie et al., "Sculptured thin films and glancing angle deposition: Growth mechanics and applications," Journal of Vacuum Science Technology: A., vol. 15, pp. 1460-1465, (1997).

Roder et al., "Tuning the microstructure of pulsed laser deposited polymer-metal nanocomposites," Applied Physics A. vol. 85, pp. 15-20 (2006).

Rosen et al., "Fibrous Capsule Formation and Fibroblast Interactions at Charged Hydrogel Interfaces," Hydrogels or Medical and Related Applications, Chapter 24, pp. 329-343, Jun. 1, 1976.

Rossi et al., "Pulsed Power Modulators for Surface Treatment by Plasma Immersion Ion Impantantion," Brazilian Journal of Physics, vol. 34, No. 4B, pp. 1565-1571, Dec. 2004.

Routkevitch, "Nano- and Microfabrication with Anodic Alumina: A Route to Nanodevices," Foresight Institute 9th Conference on Molecular Nanotechnology, pp. 1-20, Nov. 8-11, 2001, Santa Clara, CA.

Ryu et al., "Biomimetic apatite induction on Ca-containing titania," Current Applied Physics, vol. 5, pp. 512-515, (2005).

Santos et al., "Si-Ca-P xerogels and bone morphogenetic protein act synergistically on rat stromal marrow cell differentiation in vitro," Journal of Biomedical Materials Research, vol. 41, No. 1, pp. 87-94, Jul. 1998.

Santos et al., "Sol-Gel Derived Carrier for the Controlled Release of Proteins," Biomaterials, vol. 20, pp. 1695-1700, (1999).

Sardella et al., "Plasma-Aided Micro- and Nanopatterning Processes for Biomedical Applications," Plasma Processes and Polymers, vol. 3, pp. 456-469, (2006).

Sasahara et al., "Macroporous and nanosized ceramic films prepared by modified sol-gel methods with PMMA microsphere templates," Journal of the European Ceramic Society, vol. 24, pp. 1961-1967, (2004).

Sawitowski, "Nanoporous alumina for implant coating—A novel approach towards local therapy," NanoMed 3rd Workshop, Medical Applications of Nanotechnology, Berlin, 1 page, Feb. 17-18, 2003.

Sawyer et al., "The Role of Electrochemical Surface Properties in Thrombosis at Vascular Interfaces: Cumulative Experience of Studies in Animals and Man," Bulletin of the New York Academy of Medicine, Second Series, vol. 48, No. 2, pp. 235-256, (1972).

Sawyer, "Electrode-Biologic Tissue Interreactions at Interfaces—A Review;" Biomat. Med. Dev. Art. Org., 12(3-4), pp. 161-196 (1984).

Schetsky, "Shape Memory Alloys", Encyclopedia of Chemical Technology (3rd ed.), John Wiley & Sons, vol. 20, pp. 726-736, (1982).

Schlottig et al., "Characterization of nanoscale metal structures obtained by template synthesis," Fresenius' Journal of Analytical Chemistry, vol. 361, pp. 684-686, (1998).

Schneider, "Laser Cladding with Powder: Effect of some machining parameters on clad properties," Doctoral Thesis—University of Twente, The Netherlands, pp. 1-176, ISBN 9036510988, Mar. 1998.

Schnitzler et al., "Organic/Inorganic Hybrid Materials Formed From TiO2 Nanoparticles and Polyaniline," Journal of Brazilian Chemistry Society, vol. 15, No. 3, pp. 378-384, (2004).

Selective laser sintering, from Wikipedia, (http://en.wikipedia.org/wiki/Selective_laser_sintering), pp. 1-2, downloaded on Sep. 28, 2007.

Senior et al., "Synthesis of tough nanoporous metals by controlled electrolytic dealloying," Nanotechnology, vol. 17, pp. 2311-2316, (2006).

Serra et al., "Preparation of functional DNA microarrays through laser-induced forward transfer," Applied Physics Letters, vol. 85, No. 9, pp. 1639-1641, Aug. 30, 2004.

Serruys et al., "The Effect of Variable Dose and Release Kinetics on Neointimal Hyperplasia Using a Novel Paclitaxel—Eluting Stent Platform," Journal of the American College of Cardiology, vol. 46, No. 2, pp. 253-260, Jul. 19, 2005.

Sgura et al., The Lunar Stent: characteristics and clinical results, Herz, vol. 27, pp. 1-14, (2002).

Shabalovskaya et al., "Surface Conditions of Nitinol Wires, Tubing, and As-Cast Alloys. The Effect of Chemical Etching, Aging in Boiling Water, and Heat Treatment," Wiley Periodicals, Inc., Journal of Biomedical Materials Research Part B: Appiled Biomaterials, vol. 65B: pp. 193-203, (2003).

Shamiryan et al., "Comparative study of SiOCH low-k films with varied porosity interacting with etching and cleaning plasma," Journal of Vacuum Science Technology B, vol. 20, No. 5, pp. 1923-1928, Sep./Oct. 2002.

Shang et al., "Structure and photocatalytic characters of TiO2 film photocatalyst coated on stainless steel webnet," Journal of Molecular Catalysis a: Chemical, vol. 202, pp. 187-1995, (2003).

Shao et al., "Fiber mats of poly(vinyl alcohol)/silica composite via Electrospinning," Materials Letters, vol. 57, pp. 1579-1584, (2003).

Shchukin et al., "Micron-scale hollow polyelectrolyte capsules with naosized magnetic Fe304 inside," Materials Letters, vol. 57, pp. 1743-1747, (2003).

Shevchenko et al., "Porous Surface of NiTi Alloy Produced by Plasma Ion Implantation," Institute of Ion Beam Physics and Materials Research, 1 page, May 2005.

Shevchenko, "Formation of nonoporous structures on stainless steel surface," Report, pp. 1-6, Apr. 2007.

Shibli et al., "Development of phosphate inter layered hydroxyapatite coating for stainless steel implants", Applied Surface Science, vol. 254, pp. 4103-4110, (2008).

Shockravi et al., "Soluable and thermally stable polyamides bearing 1,1'-thiobis(2-naphthoxy) groups," European Polymer Journal, vol. 43, pp. 620-627, (2007).

Shustak et al., "n-Alkanoic Acid Monolayers on 316L Stainless Steel Promote the Adhesion of electropolymerized Polypyrrole Films," Langmuir, vol. 22, pp. 5237-5240, (2006).

Siegfried et al., "Reactive Cylindrical Magnatron Deposition of Titanium Nitride and Zirconium Nitride Films," Society of Vacuum Coaters, 39th Annual Technical Conference Proceedings, pp. 97-101, (1996).

Silber et al., "A new stainless-steel-free stent with a potential of artifact free magnetic resonance compatibility: first clinical experience (Ein neuer Edelstahl-freier Stent mit Potential zur artefaktfreien MR-Kompatibilitat: Erste klinische Erfahrungen)," German Society for Cardiology—Heart and Cardiovascular Research (Deutche Gesellschaft fur Kardiologie—Herz and Kreislauffforschung), 1 page, Oct. 30, 2005.

Silber et al., "A new stainless-steel-free stent with a potential of artifact free magnetic resonance compatibility: first clinical experience," Abstract and Poster, pp. 1-3, May 2006.

Silber, "LUSTY-FIM Study: Lunar Starflex First in Man Study," PowerPoint presentation at the Paris Course on Revascularization, pp. 1-11, May 2003.

Silber, "Ein edelstahfreier stent aus niobium mit iridiumoxyd (IrOx)-beschichtung: Erste Ergebnisse der LUSTY-studie" (Stainless steel-free Stent out of niobium with iridiumoxyd (IrOx)-coating: Initial results of the LUSTY-study), PowerPoint presentation, pp. 1-16, Oct. 15, 2004.

Silber, "LUSTY-FIM Study: Lunar Starflex First in Man Study," PowerPoint presentation, pp. 1- 16, 2003.

Silber, "Niobium/iridiumoxide Stents: LUSTY randomized trial, LUNAR ROX registry," PowerPoint presentation, pp. 1-33, 2003.

Silva et al., "Electrochemical characterisation of oxide films formed on Ti-6Al-4V alloy implanted with Ir for Bioengineering applications," Electrochimica Acta, vol. 43, Nos. 1-2, pp. 203-211, (1998).

Simon et al., "Influence of topography on endothelialization of stents: Clues for new designs," Journal of Long-Term Effects Of Medical Implants, Voo. 10, No. 1-2, pp. 143-151, (2000).

Singer, "Paclitaxel Poliglumex (XYOTAX, CT-2103): A Macromolecular Taxane," Journal of Controlled Release, vol. 109, 120-126, (2005).

Singh et al., "Review: Nano and macro-structured component fabrication by electron beam-physical vapor deposition (EB-PVD)," Journal of Materials Science, vol. 40, pp. 1-26, (2005).

Sniadecki et al., "Nanotechnology for Cell-Substrate Interactions," Annals of Biomedical Engineering, vol. 34, No. 1, pp. 59-74, Jan. 1, 2006.

Sofield et al., "Ion beam modification of polymers," Nuclear Instruments and Methods in Physics Research, vol. B67, pp. 432-437, (1992).

Soler-Illia et al., "Block Copolymer-Templated Mesoporous Oxides," Current Opinion in Colloid and Interface Science, vol. 8, pp. 109-126, (2003).

Song et al., "Biomimetic apatite coatings on micro-arc oxidized titania," Biomaterials, vol. 25, pp. 3341-3349, (2004).

Sousa et al., "New Frontiers in Cardiology: Drug-Eluting Stents: Part I," Circulation: Journal of the Americal Heart Associate, vol. 107, pp. 2274-2279, http/www.circ.ahajournals.org, (2003).

Spasova et al., "Magnetic and optical tunable microspheres with a magnetite/gold nanoparticle shell," Journal of Material Chemisty, vol. 115, pp. 2095-2098, (2005).

Sprague et al., "Endothelial cell migration onto metal stent surfaces under static and flow conditions," Journal of Long-Term Effects of Medical Implants, vol. 10, No. 1-2, pp. 97-110, (2000).

Startschuss fur "lusty"—studie, (Launch of "lusty"—study), Cardio News, 1 page, Oct. 2002.

Stucky "High Surface Area Materials," pp. 1-5, Published: Jan. 1998, WTEC Hyper-Librarian, (http://www.wtec.org/loyola/nano/US.Review/07_03.htm).

Studart et al., "Colloidal Stabilization of Nanoparticles in Concentrated Suspensions," Langmuir, vol. 23, pp. 1081-1090, (2007).

Sun et al., "Construction of Size-Controllable Hierarchical Nanoporous TiO2 Ring Arrays and Their Modifications," Chem. Mater, vol. 18, pp. 3774-3779, (2006).

Sun et al., "Non-Fouling Biomaterial Surfaces: II Protein Adsorption on Radiation Grafted Polyethylene Glycol Methacrylate Copolymers," Polymer Preprints, vol. 28, No. 1, pp. 292-294, Apr. 1987.

Sundararajan et al., "Mechanisms underlying the formation of thick alumina coatings through the MAO coating technology," Surface and Coatings Technolgy, vol. 167, pp. 269-277, (2003).

Sung et al., "Formation of Nanoporous and Nanocrystalline Anatase Films by Pyrolysis of PEO-TiO2 Hybrid Films," Journal of Crystal Growth, vol. 286, pp. 173-177, (2006).

Szycher et al., "Drug-Eluting Stents to Prevent Coronary Restenosis," CardioTech International, pp. 1-10, (2002).

Tabata et al., "Generalized Semiempirical Equations for the Extrapolated Range of Electronics," Nuclear Instruments and Methods, vol. 103, pp. 85-91, Mar. 28, 1972.

Takitani et al., "Desorption of Helium from Austenitic Stainless Steel Heavily Bombarded by Low Energy He Ions," Journal of Nuclear Materials, vol. 329-333, pp. 761-765, (2004).

Tamura et al., "Surface Hydroxyl Site Densities on Metal Oxides as a Measrure for the Ion-Exchange Capacity," Journal of Colloid and Interface Science, vol. 209, pp. 225-231, (1999).

Tan et al., "Corrosion and wear-corrosion behavior of NiTi modified by plasma source ion implantation," Biomaterials, vol. 24, pp. 3931-3939, (2003).

Tanaka et al., "Micrometer-scale fabrication and assembly using focused ion beam," Thin Solid Films, vol. 509, pp. 113-117, (2006).

Tang et al., "Electrochemical Study of a Polarized Electrochemical Vapor Deposition Process," Journal of The Electrochemical Society, vol. 147, No. 9, pp. 3338-3344, (2000).

Tang et al., "Fabrication of Macroporous Alumina with Tailored Porosity," Jornal of American Ceramic Society, vol. 86, No. 12, pp. 2050-2054, (2003).

Tang et al., "Preparation of Porous anatase titania film," Materials Letters, vol. 58, pp. 1857-1860, (2004).

Tapphorn et al., "The Solid-State Spray Forming of Low-Oxide Titanium Components," Journal of Metals, vol. 50, No. 9, pp. 45-46,76, (1998).

Tassin et al., "Improvement of the Wear Resistance of 316 L Stainless Steel by Laser Surface Alloying," Surface and Coatings Technology, vol. 80, No. 9, pp. 207-210, (1996).

Terlingen, "Functionalization of Polymer Surfaces," Europlasma Technical Paper, pp. 1-29, May 8, 2004.

Terumo Europe, "Terumo Europe N.V. Enrols First Patient in Clinical Trial of the Nobori Drug-Eluting Coronary Stent," Press Release, 1 page, May 26, 2005, (http://www.terumo-europe.com/_press_release/may_26_2005.html.).

Thierry et al., "Bioactive Coatings of Endovascular Stents Based on Polyelectrolyte Multilayers," Biomacromolecules, vol. 4, pp. 1564-1571, (2003).

Thompson et al., "Tuning compliance of nanoscale polyelectrolyte multilayers to modulate cell adhesion," Biomaterials, vol. 26, pp. 6836-6845, (2005).

Tierno et al., "Using Electroless Deposition for the Preparation of Micron Sized Polymer/Metal Core/Shell Particles and Hollow Metal Spheres," Journal of Physics Chemistry B, vol. 110, pp. 3043-3050, (2006).

Tollon, "Fabrication of coated biodegradable polymer scaffolds and their effects on murin embryonic stem cells," Thesis presented to the University of Florida, pp. 1-7, (2005).

Tonosaki et al., "Nano-indentation testing for plasma-based ion-implanted surface of plastics," Surface and Coatings Technology, vol. 136, pp. 249-251, (2001).

Tones-Costa et al., "RBS Characterization of Porous Silicon Multilayer Interference Filters," Electrochemical and Solid-State Letters, vol. 7, No. 11, pp. G244-G249 (2004).

Toth et al., "Ar+ laser-induced forward transfer (LIFT): a novel method for micrometer-size surface patterning," Applied Surface Science, vol. 69, pp. 317-320, (1993).

Tsyganov et al., "Blood compatibilty of titanium-bases coatings prepared by metal plasma immersion ion implantation and deposition," Applied Surface Science, vol. 235, pp. 156-163, (2004).

Tsyganov et al., "Structure and Properties of Titanium Oxide Layers prepared by Metal Plasma Immersion Ion Implantation and Deposition," Surface & Coatings Technology, vol. 174-175, pp. 591-596, (2003).

Tsyganov et al., "Correlation between blood compatibility and physical surface properties of titanium-based coatings," Surface & Coatings Technology, vol. 200, pp. 1041-1044, (2005).

Uchida et al., "Apatite-forming ability of a zirconia/alumina nanocomposite induced by chemical treatment," Journal of Biomedical Materials Research, vol. 60, No. 2, pp. 277-282, May 2002.

University of Wisconsin, "Effect of Nano-Scale Textured Biomimetic Surfaces on Proliferation and Adhesion of Corneal Epithelial Cells," Materials Research Science and Engineering Center, pp. 1-2, (1997), (http://mrsec.wisc.edu/Past_proiects/seedproi4/Seedproi4.html).

Uyama et al., "Surface Modifications of Polymers by Grafting," Advances in Polymer Science, vol. 139, pp. 1-39, (1998).

Valsesia et al., "Selective immobilization of protein clusters on polymeric nanocraters," Advanced Functional Materials, vol. 16, pp. 1242-1246, (2006).

Valsesia, a. et al., "Fabrication of nanostructured polymeric surfaces for biosensing devices," Nanoletters, vol. 4, No. 6, pp. 1047-1050, (2004).

Van Alsten, "Self-Assembled Monolayers on Engineering Metals: Structure, Derivatization, and Utility," Langmuir, vol. 15, pp. 7605-7614, (1999).

Van Den Berg, "Nano particles play with electrons," pp. 1-9, [first downloaded on Nov. 12, 2003], (http://www.delftoutlook.tudelft.nl/info/index21fd.html?hoofdstuk=Article&ArtID=2243).

van der Eijk et al., " Metal Printing Process Development of a New Rapid Manufacturing Process for Metal Parts," Proceedings of the World PM2004 Conference held in Vienna, pp. 1-5, Oct. 17-21, 2004.

Van Steenkiste et al., "Kinetic spray coatings," Surface & Coatings Technology, vol. 111, pp. 62- 71, (1999).

Vayssieres, "On the design of advanced metal oxide nanomaterials," International Journal of Nanotechnology, vol. 1, Nos. 1/2, pp. 1-41, (2004).

Velev et al., "Colloidal crystals as templates for porous materials," Current Opinion in Colloid & Interface Science, vol. 5, pp. 56-63, (2000).

Velev et al., "Porous silica via colloidal crystallization," Nature, vol. 389, pp. 447-448, Oct. 2, 1997.

Verheye et al., "Reduced Thrombus Formation by Hyaluronic Acid Coating of Endovascular Devices," Arteriosclerosis, Thrombosis, and Vascular Biology: Journal of The American Heart Association, vol. 20, pp. 1168-1172, (2000).

Vidal et al., "Electropolymerization of pyrrole and immobilization of glucose oxidase in a flow system: influence of the operating conditions on analytical performance," Biosensors & Bioelectronics, vol. 13, No. 3-4, pp. 371-382, (1998).

Vigil et al., "TiO2 Layers Grown from Flowing Precursor Solutions Using Microwave Heating," Langmuir, vol. 17, pp. 891-896, (2001).

Viitala et al., "Surface properties of in vitro bioactive and non-bioactive sol-gel derived materials," Biomaterials, vol. 23, pp. 3073-3086, (2002).

Vitte et al., "Is there a predictable relationship between surface physical-chemical properties and cell behaviour at the interface?" European Cells and Materials, vol. 7, pp. 52-63, (2004).

Volkel et al., "Electrodeposition of coppeer and cobalt nanostructures using self-assembled monolayer templates," Surface Science, vol. 597, pp. 32-41, (2005).

Vu et al., "Eletrophoretic deposition of nanocomposites formed from polythiophene and metal oxides," Electrochimica Acta, vol. 51, pp. 1117-1124, (2005).

VukoviO et al., "Anodic stability and electrochromism of electrodeposited ruthenium-iridium coatings on titanium," Journal of Electroanalytical Chemisty, vol. 330, pp. 663-673 (1992).

Walboomers et al., "Effect of microtextured surfaces on the performance of percutaneous devices," Journal of Biomedical Materials Research Part A, vol. 74A, No. 3, pp. 381-387, (2005).

Wang et al., "Deposition of in-plane textured MgO on amorphous Si3N4 substrates by ion-beam-assisted deposition and comparisons with ion-beam-assistend deposidted yttria-stabilized-zirconia," Applied Physics Letters, vol. 71, No. 17, Issue 20, pp. 2955-2957, Nov. 17, 1997.

Wang et al., "Effect of substrate temperature on structure and electrical resistivity of laser ablated IrO2 thin films," Applied Surface Science, vol. 253, pp. 2911-2914, (2006).

Wang et al., "Effect of the discharge pulsating on microarc oxidation coating formed on Ti6A14V alloy," Materials Chemistry and Physics, vol. 90, pp. 128-133, (2005).

Wang et al., "Novel Poly(3-nonylthiophene)-TiO2 Hybrid Materials for Photovoltaic Cells," Synthetic Metals, vol. 155, pp. 677-680, (2005).

Wang et al., "Polyelectrolyte-Coated Colloid Spheres as Templates for Sol-Gel Reactions," Chem. Mater., vol. 14, pp. 1909-1913, (2002).

Wang et al., "Pulsed laser deposition of organic thin films," This Solid Films, vol. 363, pp. 58-60, (2000).

Wang et al., "Synthesis of Macroporous Titania and Inorganic Composite Materials from Coated Colloidal Spheres—A Novel Route to Tune Pore Morphology," Chem. Mater., vol. 13, pp. 364-371, (2001).

Webster et al."Enhanced functions of osteoblasts on nanophase ceramics," Biomaterials, vol. 21, No. 17, pp. 1803-1810, Sep. 2000.

Webster et al., "Increased osteoblast adhesion on nanophase metals: Ti, Ti6A14V, and CoCrMo," Biomaterials, vol. 25, No. 19, pp. 4731-4739, (2004).

Webster et al., "Specific proteins mediate enhanced osteoblast adhesion on nanophase ceramics," Journal of Biomedical Materials Research, vol. 5, No. 51, pp. 475-483, Sep. 2000.

Wei et al., "Structural Characterisation of Doped and Undoped Nanocrystalline Zinc Oxides Deposited by Ultrasonic Spray Assisted Chemical Vapour Deposition," Journal of Physics: Conference Series, vol. 26, pp. 183-186 (2006).

Wells, "Patterned Plasma Immersion Exposure of Insulating Materials for the Purpose of Modifying Optical Properties," thesis submitted to the college of William and Mary, Williamsburg, Vriginia, pp. 1-59, Apr. 2000.

Wesolowski et al., "Surface Charge and Ion Adsorption on Metal Oxides to 290° C.," Division of Chemical Sciences, Geosciences, and Biosciences, Office of Basic Energy Sciences, U.S. Department of Energy, pp. 1-6, (2001).

Wessling et al., "RF-sputtering of iridium oxide to be used as stimulation material in functional medical implants," Journal of Micromechanics and Microengineering, vol. 16, pp. S142-S148 (2006).

Whelan, "Targeted Taxane Therapy for Cancer," Drug Discovery Today, vol. 7, No. 2, pp. 90-92, Jan. 2002.

Which stent is right for you? pp. 1-3, (circa 2004).

Wieneke et al., "Synergistic Effects of a Novel Nanoporous Stent Coating and Tacrolimus on Intima Proliferation in Rabbits," Catheterization and Cardiovascular Interventions, vol. 60, pp. 399-407, (2003).

Wilkinson et al., "Nanofabrication in cellular engineering," Journal of Vacuum Science & Technology B, vol. 16, No. 6, pp. 3132-3136, (1998).

Wilkinson et al., "The use of materials patterned on a nano- and micro-metric scale in cellular engineering," Materials Science & Engineering C, vol. 19, No. 1-2, pp. 263-269, (2002).

Wilson et al., "Mediation of biomaterial-cell interactions by adsorbed proteins: A review," Tissue Engineering, vol. 11, No. 1-2, pp. 1-18, (2005).

Wong et al., "Balance of chemistry, topography, and mechanics at the cell-biomaterial interface: Issues and challenges for assessing the role of substrate mechanics on cell response," Surface Science, vol. 570, No. 1-2, pp. 119-133, (2004).

Wong et al., "Polymer segmental alignment in polarized pulsed laser-induced periodic surface structures," Applied Physics A, vol. 65, pp. 519-523, (1997).

Wood, "Next-generation drug-eluting stents tackle shortcomings of Cypher, Taxus," Heart Wire, pp. 1-6, Feb. 7, 2006, (http://www.theheart.org/article/641591.do.).

World Reference definition, "Interconnected," WorldReference.com, 1 page, [downloaded Jan. 21, 2010].

Wu et al., "Characterization of Mesoporous Nanocrystalline TiO2 Photocatalysts Synthesized Via a Sol-Solvothermal Process at a Low Temperature," Journal of Solid State Chemistry, vol. 178, pp. 321-328, (2005).

Wu et al., "Chitosan-Mediated and Spatially Selective Electrodeposition of Nanoscale Particles," Langmuir, vol. 21, pp. 3641-3646, (2005).

Wu et al., "Corrosion resistance of BaTiO3 films prepared by plasma electrolytic oxidation," Surface and Coatings Technology, vol. 166, pp. 31-36, (2002).

Wu et al., "Design of Doped Hybrid Xerogels for a Controlled Release of Brilliant Blue FCF," Journal of Non-Crystalline Solids, vol. 342, pp. 46-53, (2004).

Wu et al., "The effects of cathodic and anodic voltages on the characteristics of purous nanocrystalline titania coatings fabricated by microarc oxidation," Materials Letters, vol. 59, pp. 370-375, (2005).

Xia et al., "Monodispersed Colloidal Spheres: Old Materials with New Applications," Advanced Materials, vol. 12, No. 10, pp. 693-713, (2000).

Xu et al., "An Improved Method to Strip Aluminum from Porous Anodic Alumina Films," Langmuir, vol. 19, pp. 1443-1445, (2003).

Xu et al., "Cold spay deposition of thermoplastic powder," Surface & Coatings Technology, vol. 2001, pp. 3044-3050, (2006).

Xu et al., "Synthesis of porosity controlled ceramic membranes," Journal of Material Research, vol. 6, No. 5, pp. 1073-1081, May 1991.

Yamato et al. "Nanofabrication for micropatterned cell arrays by combining electron beam-irradiated polymer grafting and localized laser ablation," Journal of Biomedical Materials Research, vol. 67, No. 4, pp. 1065-1071, Dec. 15, 2003.

Yan et al., "New MOCVD precursor for iridium thin films deposition," Materials Letters, vol. 61, pp. 216-218, (2007).

Yan et al., "Sol-gel Processing," Handbook of Nanophase and Nanostructured Materials, vol. 1: Synthesis, Chapter 4, pp. 1-27, (2003).

Yang et al., "Laser spray cladding of porous NiTi coatings on NiTi substrates," The Hong Kong Polytechnic University, 1 page, Dec. 28, 2006.

Yang et al., "Poly(L,L-lactide-co-glycolide)/tricalcium phosphate composite scaffold and its various changes during degradation in vitro," Polymer Degradation and Stability, vol. 91 pp. 3065-3073, (2006).

Yang et al., "Thermal oxidation products and kinetics of polyethylene composites," Polymer Degradation and Stability, vol. 91, pp. 1651-1657, (2006).

Yang et al., "Solution phase synthesis of magnesium hydroxide sulfate hydrate nanoribbons", Nanotechology, vol. 15, pp. 1625-1627, (2004).

Yankov et al., "Reactive plasma immersion ion implantation for surface passivation," Surface and Coatings Technology, vol. 201, pp. 6752-6758, (2007).

Yap et al., "Protein and cell micropatterning and its integration with micro/nanoparticles assembley," Biosensors and Bioelectronics, vol. 22, pp. 775-788, (2007).

Yerokhin et al., "Kinetic aspects of aluminium titanate layer formation on titanium alloys by plasma electrolytic oxidation," Applied Surface Science, vol. 200, pp. 172-184, (2002).

Yerokhin et al., "Plasma electrolysis for surface engineering," Surface Coatings Technology, vol. 122, pp. 73-93, (1999).

Yim et al., "Nanopattern-induced changes in morphology and motility of smooth muscle cells," Biomaterials, vol. 26, pp. 5405-5413, (2005).

Yim et al., "Significance of synthetic nanostructures in dictating cellular response," Nanomedicine: Nanotechnology, Biology and Medicine, vol. 1, No. 1, pp. 10-21, Mar. 1, 2005.

Yoldi et al., "Electrophoretic deposition of colloidal crystals assisted by hydrodynamic flows," Journal of Materials Science, vol. 41, pp. 2964-2969, (2006).

Yoshida et al., "Impact of Low Energy Helium Irradiation on Plasma Facing Metals," Journal of Nuclear Materials, vol. 337-339, pp. 946-950, (2005).

Young et al., "Polarized electrochemical vapor deposition for cermet anodes in solid oxide fuel cells," Solid State Ionics, vol. 135, pp. 457-462, (2000).

Yu et al., "Encapsulated cells: an atomic force microscopy study," Biomaterials, vol. 25, pp. 3655-3662, (2004).

Yu et al., "Enhanced photocatalytic activity of mesoporous and ordinary TiO2 thin films by sulfuric acid treatment," Applied Catalysis B: Environmental, vol. 36, pp. 31-43, (2002).

Yu et al., "Enhanced photoinduced super-hydrophilicity of the sol-gel-derived TiO2 thin films by Fe-doping," Materials Chemistry and Physics, vol. 95, pp. 193-196, (2006).

Yu et al., "Light-induced super-hydrophilicity and photocatalytic activity of mesoporous TiO2 thin films," Journal of Photochemistry and Photobiology A: Chemistry, vol. 148, pp. 331-339, (2002).

Yun et at., "Low-Temperature Coating of Sol-Gel Anatase Thin Films," Materials Letters, vol. 58, pp. 3703-3706, (2004).

Zakharian et al., "A Fullerene—Paclitaxel Chemotherapeutic: Synthesis, Characterization, and Study of Biological Activity in Tissue Culture," Journal of American Chemistry Society, vol. 127, pp. 12508-12509, (2005).

Zbroniec et al., "Laser ablation of iron oxide in various ambient gases," Applied Surface Science, vol. 197-198, pp. 883-886, (2002).

Zeng et al., "Biodegradable electrospun fibers for drug delivery," Journal of Controlled Release, vol. 92, pp. 227-231, (2003).

Zhang et al., "Surface analyses of micro-arc oxidized and hydrothermally treated titanium and effect on osteoblast behavior," Journal of Biomedical Materials Research, vol. 68A, pp. 383-391, (2004).

Zhang et al., "Surface treatment of magnesium hydroxide to improve its dispersion in organic phase by the ultrasonic technique", Applied Surface Science, vol. 253, pp. 7393-7397, (2007).

Zhao et al., "Coating deposition by the kinetic spray process," Surface & Coatings Technology, vol. 200, pp. 4746-4754, (2006).

Zhao et al., "Designing Nanostructions by Glancing Angle Deposition," Proceedings of SPIE, vol. 5219: Nanotubes and Nanowires, pp. 59-73, (2003).

Zhao et al., "Formulation of a ceramic ink for a wide-array drop-on-demand ink jet printer," Ceramics International, vol. 29, pp. 887-892, (2003).

Zheng et al., "Substrate temperature dependent morphology and resistivity of pulsed laser deposited iridium oxide thin films," Thin Solid Films, vol. 496, pp. 371-375, (2006).

Zheng et al., "Synthesis of Mesoporous Silica Materials via Nonsurfactant Templated Sol-Gel Route Using Mixture of Organic Compounds as Template," Journal of Sol-Gel Science and Technology, vol. 24. pp. 81-88, (2002).

Zhitomirsky et al., "Cathodic electrodeposition of MnOx films for electrochemical supercapacitors," Electrochimica Acta, vol. 51, pp. 3039-3045, (2006).

Zhitomirsky et al., "Electrodeposition of composite hydroxyapatite-chitosan films," Materials Chemistry and Physics, vol. 94, pp. 245-251, (2005).

Zhou et al., "Branched Ta nanocolumns grown by glancing angle deposition," Applied Physics Letters, vol. 88, p. 203117, (2006).

Zoppi et al., "Hybrid Films of Poly(ethylene oxide-b-amide 6) Containing Sol-Gel Silicon or Titanium Oxide as Inorganic Fillers: Effect of Morphology and Mechanical Properties on Gas Permeability," Polymer, vol. 41, pp. 5461-5470, (2000).

Zou et al., "Highly textural lamellar mesostructured magnesium hydroxide via a cathodic electrodeposition process", Materials Letters, vol. 61, pp. 1990-1993, (2007).

US 6,533,715, 03/2003, Hossainy et al. (withdrawn)

* cited by examiner

US 7,931,683 B2

ARTICLES HAVING CERAMIC COATED SURFACES

FIELD OF THE INVENTION

The present invention relates to articles, including medical articles, which have ceramic coated surfaces.

BACKGROUND OF THE INVENTION

Articles are provided with ceramic surfaces for use in myriad applications. Accordingly there is continuing demand for novel ceramic-coated articles and for methods of making the same.

SUMMARY OF THE INVENTION

According to an aspect of the present invention, articles are provided which comprise a substrate and a ceramic coating that covers at least a portion of the substrate surface. The ceramic coating includes raised ceramic shells connected by an underlying ceramic layer that is conformal with the substrate. The shells may be partially or completely filled, or they may be hollow.

According to another aspect of the present invention, carbon nanotubes are provided, which comprise a ceramic coating covering at least a portion of the carbon nanotubes.

The above and other aspects, as well as various embodiments and advantages of the present invention will become immediately apparent to those of ordinary skill in the art upon review of the Detailed Description and Claims to follow.

DETAILED DESCRIPTION OF THE INVENTION

According to an aspect of the present invention, articles are provided which comprise a substrate and a ceramic coating that covers at least a portion of the substrate surface. The ceramic coating includes raised ceramic shells connected by an underlying ceramic layer that is conformal with the substrate. The shells may partially or completely filled, or they may be hollow. As discussed in more detail below, in certain embodiments, the ceramic coating constitutes a single ceramic structure extending over the entire substrate surface.

As used herein a "layer" of a given material is a region of that material whose thickness is smaller than both its length and width. For example, the length and width may each be at least 5 times the thickness, for instance, independently ranging from 5 to 10 to 30 to 100 to 300 to 1000 or more times the thickness. As used herein a layer need not be planar, for example, taking on the contours of an underlying substrate. Thus, the ceramic shells described herein are layers. A layer can be discontinuous (e.g., patterned).

As used herein a "ceramic" region, for example, a ceramic layer or a ceramic shell, is a region of material that contains a single ceramic species or a mixture of two or more different ceramic species. For example, a ceramic region in accordance with the invention will typically comprise, for example, from 10 wt % or less to 25 wt % to 50 wt % to 75 wt % to 90 wt % to 95 wt % to 95 wt % or more of one or more ceramic species. A ceramic region in accordance with the invention can thus comprise species other than ceramic species, for example, in some embodiments, comprising from 1 wt % or less to 2 wt % to 5 wt % to 10 wt % to 25 wt % to 50 wt % or more polymeric species.

Ceramic species for use in ceramic regions include metal and semi-metal oxides, metal and semi-metal nitrides, and metal and semi-metal carbides, among others. Examples of metal and semi-metal oxides, nitrides and carbides include oxides nitrides and carbides of Periodic Table Group 14 semi-metals (e.g., Si, Ge), and oxides nitrides and carbides of transition and non-transition metals such as Group 3 metals (e.g., Sc, Y), Group 4 metals (e.g., Ti, Zr, Hf), Group 5 metals (e.g., V, Nb, Ta), Group 6 metals (e.g., Cr, Mo, W), Group 7 metals (e.g., Mn, Tc, Re), Group 8 metals (e.g., Fe, Ru, Os), Group 9 metals (e.g., Co, Rh, Ir), Group 10 metals (e.g., Ni, Pd, Pt), Group 11 metals (e.g., Cu, Ag, Au), Group 12 metals (e.g., Zn, Cd, Hg), Group 13 metals (e.g., Al, Ga, In, Tl), Group 14 metals (e.g., Sn, Pb), Group 15 metals (e.g., Bi). Carbides and nitrides of metal and semi-metal oxides may be formed, for example, using high-temperature carbothermal reduction and nitridation processes, among others.

Figure 3A:
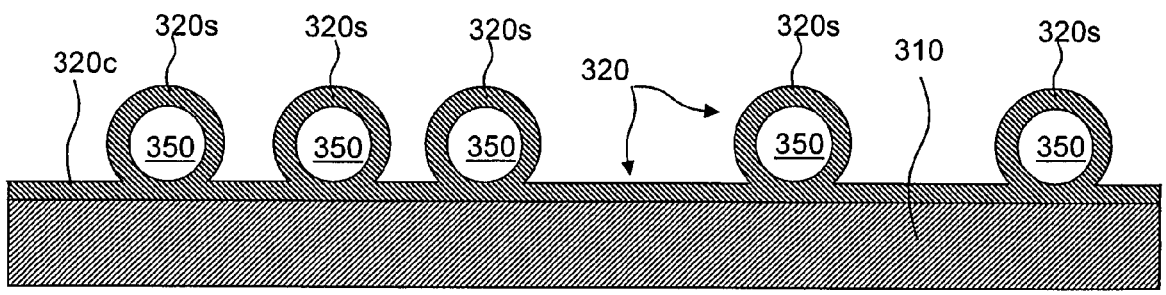
FIG. 3A is a schematic cross-sectional view of an article with a ceramic coating, in accordance with an embodiment of the present invention.

One example of an article in accordance with the invention is illustrated schematically in the cross-section of FIG. 3A, in which is shown a substrate 310, covered with a ceramic coating 320 that includes raised ceramic shells 320s connected by a conformal ceramic layer 320c. The interiors 350 of the ceramic shells 320s are hollow as shown. The conformal ceramic layer 320c can be made very thin (e.g., 100 nm or less), and therefore able to readily deform (e.g., flex or bend) with the underlying substrate. Moreover, the ceramic shells 320 can be evenly spaced (see FIG. 3) such that they do not engage each other during moderate bending/flexing. The height of the ceramic shells 320s can vary by several orders of magnitude and depends on the size of the particles that are used as templates to form the shells, as discussed further below.

Figure 3B:
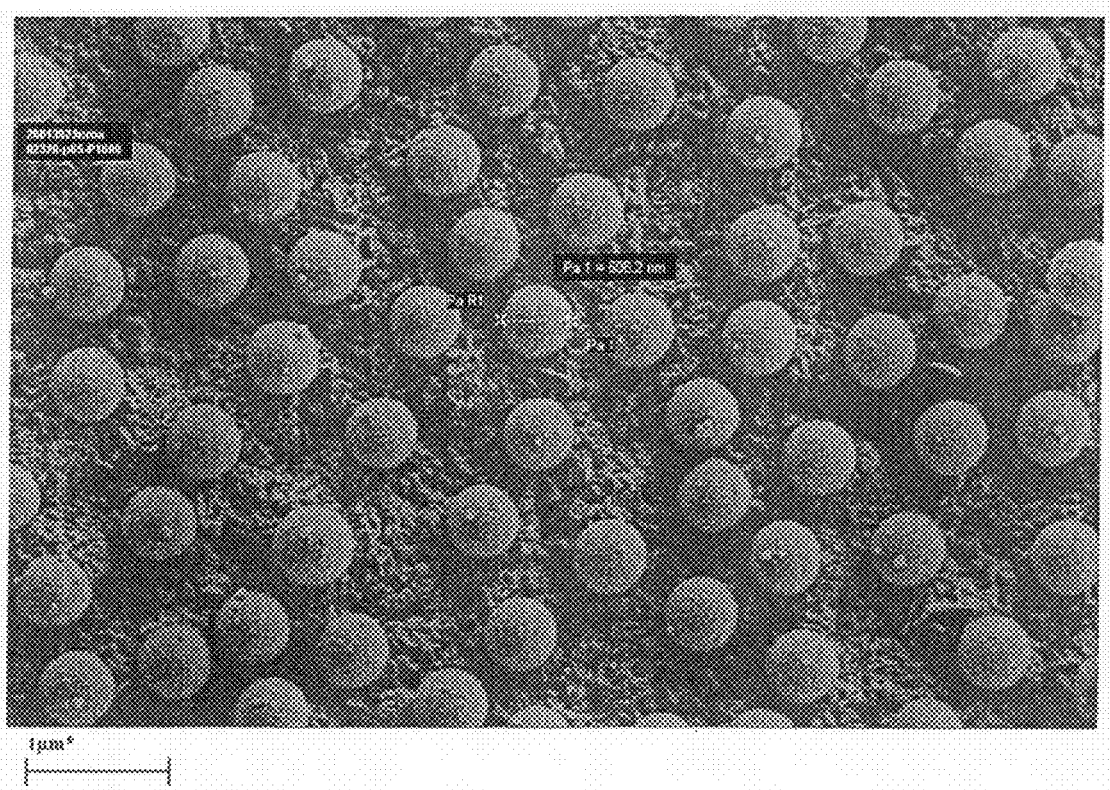
FIGS. 3B and 3C are SEM images of ceramic coatings in accordance with the present invention.
Figure 3C:
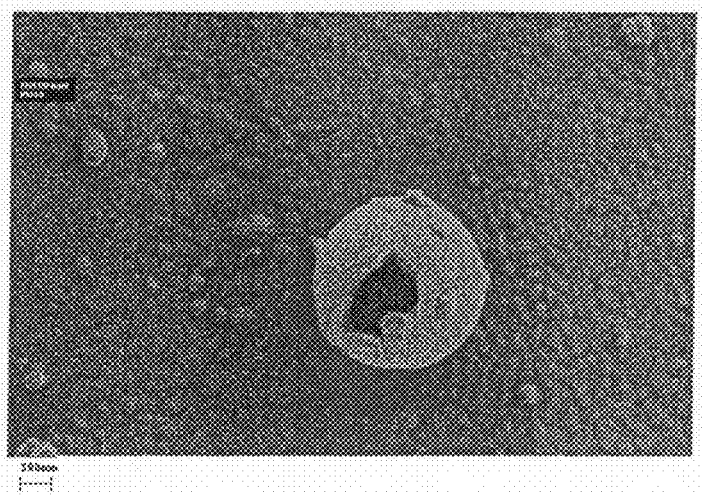

FIG. 3B is an SEM of a structure like that illustrated schematically in FIG. 3A. FIG. 3C is an SEM of a single raised ceramic shell. It is broken, demonstrating that it is hollow. Differences in surface roughness from sample to sample may arise from several parameters, including roughness of the underlying substrate as well as processing variations. Although it is not obvious upon viewing the SEM's, the ceramic layer covering the substrate and the ceramic shell of the spheres is one continuous structure, as schematically illustrated in FIG. 3A.

In FIGS. 3A-3C, the ceramic shells are spherical. However, as discussed further below, the ceramic shells can take on a near infinite range of shapes, depending on the template particles that are used to form the shells. In FIGS. 3A-3C, the interiors ceramic shells are hollow. However, the interiors of the ceramic shells can be partially or wholly filled with a near infinite array of substances, including metals, polymers, ceramics and combinations (hybrids) of the foregoing, among other materials, depending upon the template particle that is used to form the shells, and upon whether or not the template particle is wholly or partially removed during processing. As one specific example, the ceramic shells may comprise carbon nanotubes (e.g., providing mechanical reinforcement, etc.), among many other possibilities.

The present invention is applicable to virtually any article for which a ceramic coating is useful, so long as the substrate being coated is compatible with the processing conditions employed. Coated articles include articles with ceramic coatings that are either provided with or without shell structures, and where shell structures are provided, which shell structures may be hollow or contain reinforcing particles (e.g., carbon nanotubes, etc.). Such coatings may be provided for various reasons, including corrosion resistance, wear resistance, optical properties, anti-viral and anti-bacterial properties (e.g., anatase TiOx coatings, etc.) and photoactive behavior, among others. Example of articles include the following: automobile components, including complete car frames, may be coated with ceramic layers, the inside of transport pipes for gas, oil, other aggressive chemical media, photocatalytic and photovoltaic articles (e.g., by forming photoactive ceramic coatings, such as anatase coatings, on polymer substrates), aerospace articles (e.g., exterior panels of planes, space shuttles, rockets, etc.), metallic firearm components, windows (e.g., nanometer-thick coatings formed in accordance with the invention may act as reflective coatings, etc.), doorknobs and door handles, telephones, floor tiles, vinyl wall paper, plastic banknotes (e.g., such as those used in certain countries such as Australia), coins, furniture, including furniture found in public places, seats (e.g., in cars, trains and buses), railings including stairway railings and the rubber hand belts of escalators, polymer based children toys (including those used in schools, daycare, etc.), and keypads on ATM machines, among many other articles.

In certain embodiments, the coated articles are medical articles. Medical articles include articles for exterior application to the body such as patches for delivery of therapeutic agent to intact skin and broken skin (including wounds) and implantable or insertable devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglilmi detachable coils and metal coils), septal defect closure devices, drug depots that are adapted for placement in an artery for treatment of the portion of the artery distal to the device, myocardial plugs, patches, pacemakers, leads including pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other devices that are implanted or inserted into the body.

The devices of the present invention include, for example, implantable and insertable medical devices that are used for systemic treatment, as well as those that are used for the localized treatment of any tissue or organ of a subject. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone. As used herein, "treatment" refers to the prevention of a disease or condition, the reduction or elimination of symptoms associated with a disease or condition, or the substantial or complete elimination of a disease or condition. "Subjects" include vertebrate subjects, for example, humans, livestock and pets.

Medical devices of the present invention include a variety of implantable and insertable medical devices for insertion into and/or through a wide range of body lumens, several of which are recited above, including lumens of the cardiovascular system such as the heart, arteries (e.g., coronary, femoral, aorta, iliac, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract such as the trachea, bronchi, nasal passages and sinuses, lumens of the gastrointestinal tract such as the esophagus, gut, duodenum, small intestine, large intestine, rectum, biliary and pancreatic duct systems, lumens of the lymphatic system, and the major body cavities (peritoneal, pleural, pericardial), among others.

Medical device substrates which can be provided with ceramic coatings in accordance with the invention may correspond, for example, to an entire medical device (e.g., a metallic stent) or to only a portion of a medical device (e.g., corresponding to a component of a medical device, a material that is adhered to a medical device or device component, etc.).

Several exemplary embodiments of the present invention will now be described in conjunction with vascular stents for purposes of illustrating the invention. However, the invention is in no way limited to stents, or even medical articles, as seen from the above.

Figure 1A:
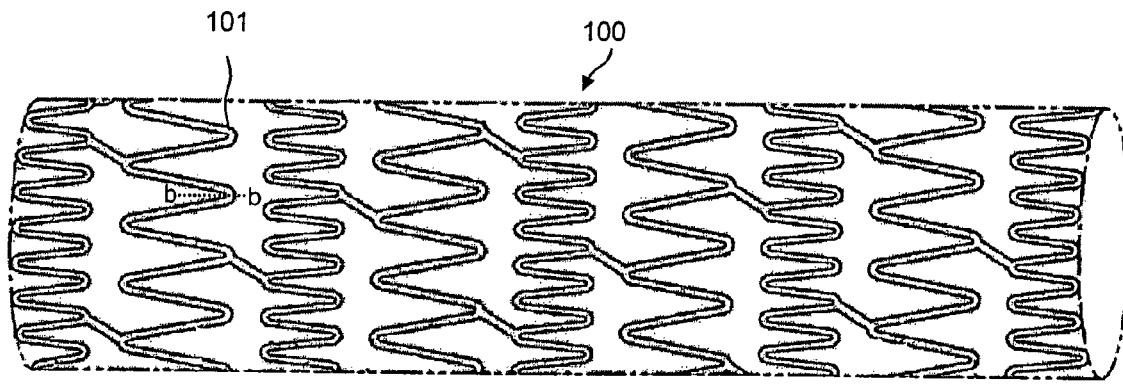
FIG. 1A is a schematic perspective view of a stent in accordance with the prior art.
Figure 1B:
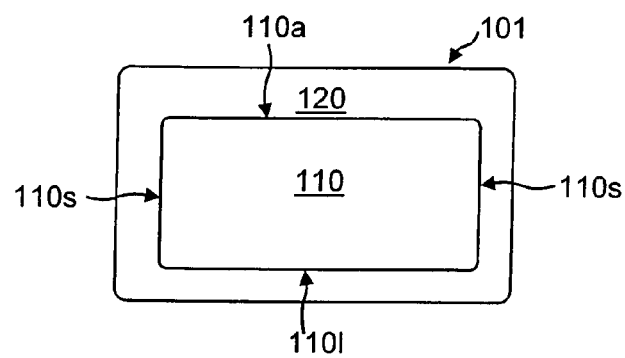
FIG. 1B is a schematic cross-sectional view taken along line b-b of FIG. 1A.

By way of background, coronary stents such as those commercially available from Boston Scientific Corp. (TAXUS and PROMUS), Johnson & Johnson (CYPHER), and others are frequently prescribed for use for maintaining blood vessel patency, for example, after balloon angioplasty. These products are based on metallic balloon expandable stents with biostable polymer coatings, which release antiproliferative therapeutic agents at a controlled rate and total dose, for preventing restenosis of the blood vessel. One such device is schematically illustrated, for example, in FIGS. 1A and 1B. FIG. 1A is a schematic perspective view of a stent 100 which contains a number of interconnected struts 101. FIG. 1B is a cross-section taken along line b-b of strut 101 of stent 100 of FIG. 1A, and shows a stainless steel strut substrate 110 and a therapeutic-agent-containing polymeric coating 120, which encapsulates the entire stent strut substrate 110, covering the luminal surface 110*l* (blood side), abluminal surface 110*a* (vessel side), and side 110*s* surfaces thereof.

While it is desirable to provide the abluminal surface of such a stent with a polymeric coating that is capable of releasing an antiproliferative drug to combat restenosis, such a drug may not be equally desirable on the luminal surface of the stent. If a polymeric coating were to be applied only to the abluminal surface of the stent, good adhesion between the stent surface and the polymeric coating is desired, because the polymeric coating is no longer secured to the stent merely by virtue of the fact that it surrounds the stent struts. Without sufficient adhesion, delamination of the coating from the stent surface may occur, for example, during delivery of the stent.

Moreover, even with good adhesion between the stent surface and the polymeric coating, in the case of a soft polymeric coating, the coating might nonetheless be rubbed from the surface of a self-expanding stent as a result of the high shear forces associated with the sliding removal of the stent from its delivery tube.

What is desired on the luminal surface of the stent, on the other hand, is a surface that promotes the rapid formation of a functional endothelial cell layer, which is known to be effective for purposes of reducing or eliminating inflammation and thrombosis that can occur in conjunction with the implantation of a foreign body in the vasculature. See, e.g., J. M. Caves et al., *J. Vasc. Surg.* (2006) 44: 1363-8.

One or more of the above goals, among others, may be achieved using ceramic coatings in accordance with the invention, which as noted above, in some embodiments, include raised ceramic shells (which may be hollow, or partially or wholly filled with a variety of solid materials) connected by a ceramic layer.

Figure 2A:
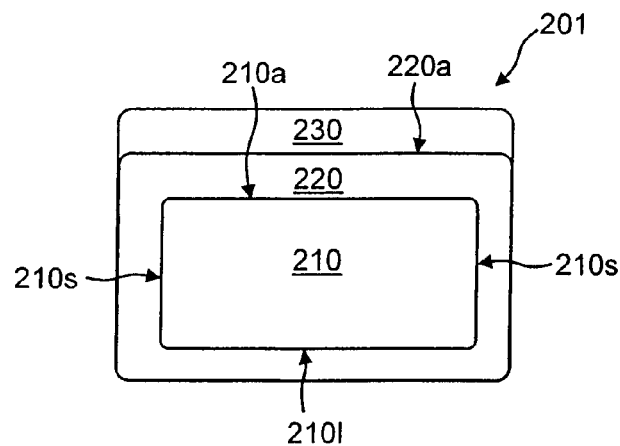
FIGS. 2A and 2B are schematic cross sectional views of stent struts, in accordance with two embodiments of the present invention.
Figure 2B:
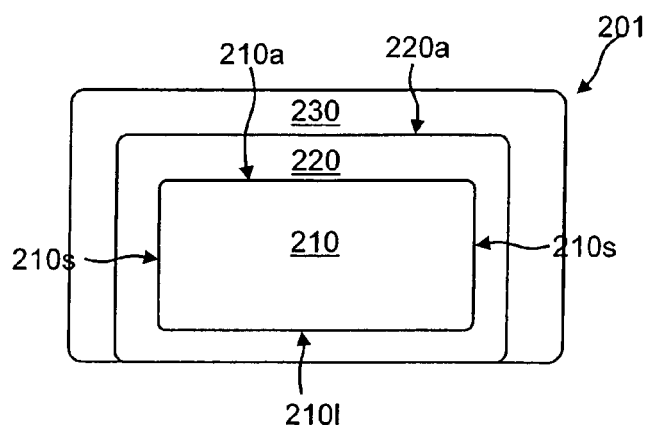

For example, referring now to FIG. 2A, which is a schematic cross sectional view of a stent strut 201, a ceramic coating 220 in accordance with the invention is provided over the luminal surface 210*l*, the abluminal surface 210*a*, and the side surfaces 210*s* of the stent strut substrate 210. A drug-eluting polymeric layer 230 is provided on the ceramic coating 220, but only over the abluminal surface 210*a* of the stent strut substrate 210 (and not over the luminal 210*l* and side 210*s* surfaces). As another example, and with reference to FIG. 2B, a ceramic coating 220 in accordance with the invention is again provided over the luminal 210*l*, abluminal 210*a* and side 210*s* surfaces of the stent strut substrate 210, whereas the drug-eluting polymeric layer 230 is provided over the abluminal surface 210*a* and side 210*s* surfaces of the stent strut substrate 210, but not over the luminal 210*l* surface. Note that in either embodiment, if the polymer used in the polymeric coating 230 is biodisintegrable, one is ultimately left in vivo with a ceramic coating, which can be selected from various materials that are biologically inert or bioactive (e.g., titanium oxide, zirconium oxide, iridium oxide, etc.).

With respect to addressing the above-mentioned goals, ceramic coatings 220 in accordance with the present invention, particularly those embodiments where the ceramic structure comprises a plurality of ceramic shells, promote polymer coating adhesion, for example, by increasing the interfacial surface area between the polymeric coatings 230 and the underlying ceramic coating 220 (i.e., relative to the interfacial surface area that would otherwise exist between the between the polymeric coating 230 and the substrate 210, in the absence of the ceramic structure 220). In addition, ceramic coatings in accordance with the invention interlock with the adjacent polymeric coating 230 to a lesser or greater degree.

Figure 4A:
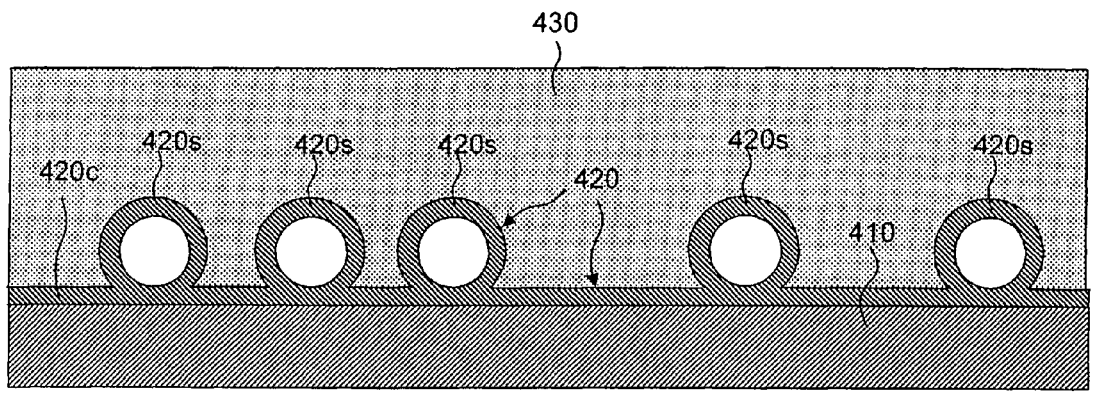
FIGS. 4A and 4B are schematic cross-sectional views of articles with ceramic coatings, which are further comprise polymeric layers, in accordance with two embodiments of the present invention.

This can be better seen with reference to FIG. 4A, which is a schematic illustration of a substrate 410 (e.g., a stent strut, among innumerable other possibilities), having disposed thereon a ceramic coating 420 in accordance with the invention. The coating 420 includes raised ceramic shells 420*s* connected by a ceramic layer 420*c* that is conformal with the substrate 410. As previously noted, the raised ceramic shells 420*s* and ceramic layer 420*c* constitute a single ceramic structure. A polymeric coating 430 is shown, disposed over the ceramic coating 420. Due to the undercut beneath the ceramic shells 420*s*, the polymeric coating 430 interlocks to a degree with the ceramic coating 420. As seen from FIGS. 7H and 8C (discussed further below), more complex, ceramic coatings can be formed which are capable of creating even greater degrees of interlock between the ceramic coatings of the invention and polymeric layers overlying them.

Figure 4B:
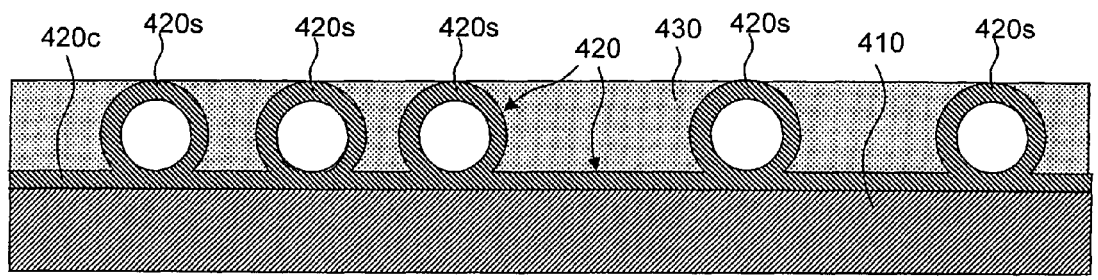

With regard to the ability of the ceramic coatings of the invention to protect polymeric coatings (e.g., against shear forces, abrasion, etc.), one such embodiment can be seen with reference to FIG. 4B, which like FIG. 4A is a schematic illustration of a substrate 410, having disposed thereon a ceramic coating 420 in accordance with the invention, which includes raised ceramic shells 420*s* connected by a ceramic layer 420*c* that is conformal with the substrate 420. A polymeric coating 430 is shown, disposed over the ceramic coating 420. Unlike FIG. 4A, however, the polymeric coating 430 does not extend substantially beyond the height of the raised ceramic shells 420*s*. Consequently, the ceramic shells 420*s* are able to protect the polymeric coating 430 from being rubbed off, for example, as a result of abrasion, shear forces, and so forth.

Figure 4C:
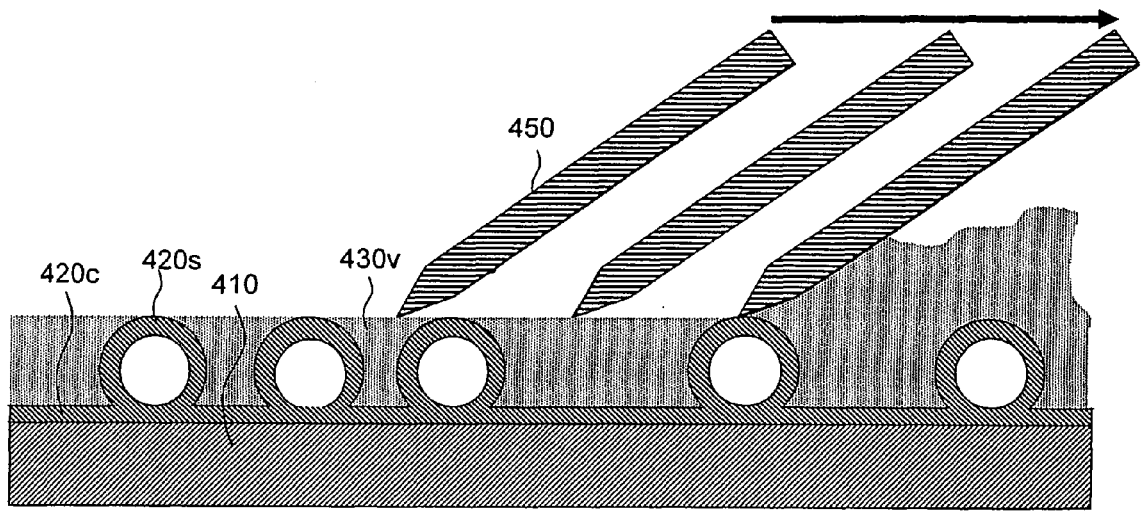
FIG. 4C is schematic cross-sectional view illustrating a process for forming a polymeric layer like that of FIG. 4B.

One example of a process for producing a polymeric coating 430 like that of FIG. 4B is schematically illustrated in FIG. 4C. After covering the ceramic coating 420*c*,420*s* with a viscous polymer solution 430*v*, a blade is run over the structure (three blades 450 are illustrated in FIG. 4C, arranged in a manner analogous to a triple-edge razor). The ceramic shells 420*s* act to limit the extent to which the blades 450 can approach the ceramic layer 420*c*. Consequently, a polymeric layer is created that is essentially of the same height as the ceramic shells 420*s*. Because the viscous polymer solution 430*v* will loose volume upon evaporation of the solvent contained therein, one may repeat the process, as desired, to increase the thickness of the final polymeric layer. Of course other liquid polymeric compositions can be employed in the polymeric coating process, including polymer melts and curable polymeric compositions.

Thus, where employed in conjunction with a stent, a ceramic coating like that shown in FIG. 4B allows a soft polymeric coating to be protected against mechanical forces, without affecting the mechanical qualities of the stent. With respect to the latter advantage, another option for protecting a polymer coating from mechanical forces would be to form depressions within the stent surface, which would shield the polymeric coating. However, the amount polymeric coating (and thus therapeutic agent) that can be loaded within these depressions is limited to the amount of material that is removed, with significant removal of material potentially weakening the stent.

Another advantage of a ceramic coating like that shown in FIG. 4B, is that the coating allows for very good control over the height and total volume of any therapeutic-agent-containing polymer layer, and therefore over therapeutic agent content. More particularly, the coating height is dependent on the height of the spherical shell, and this is defined by the size of the original template particles (e.g., polystyrene balls) which one can obtain with a variance in size of better than 2.0%. One has to take into account the volume taken up by the spheres. However, this can be done by taking into account the diameter and average density of the spherical shells, which are uniformly dispersed on the surface, as can be seen from FIG. 3B.

With respect to the goal of providing a stent surface that promotes the rapid formation of a functional endothelial cell layer, ceramic coatings of the invention are readily formed with micron-scale and/or nanometer-scale features, which have been widely reported to promote cell attachment and/or cell proliferation as discussed below. In this regard, ceramic coatings can be produced with topographical features having a wide variety of shapes and sizes. The surface features generally have widths that are less than 100 microns (µm), ranging, for example, from 100 microns or more to 50 microns to 25 microns to 10 microns to 5 microns to 2 microns to 1 micron to 500 nm to 250 nm to 100 nm to 50 nm to 25 nm or less. As discussed below, the shapes and sizes of the surface features are dictated by the particles that are used as templates for the creation of the ceramic shells.

As noted above, cell attachment and cell growth (proliferation) on surfaces have both been reported to be influenced by the texturing found on the surface. For instance, literature has shown that endothelial cells cultured on textured surfaces spread faster and appear more like cells in native arteries. See R. G. Flemming et al., *Biomaterials* 20 (1999) 573-588. It has been reported that textured surfaces promote stabilized pseudo-neointima formation. In this regard, N. Fujisawa et al., *Biomaterials* 20 (1999) 955-962 found that, upon implantation in ovine carotid arteries, textured polyurethane surfaces consisting of regularly spaced, protruding micro-fibers on a smooth base plane (length, pitch and diameter at the base of the fibers were 250, 100 and 25 µm, respectively) promoted the formation of a stabilized thrombus base onto which subsequent cellular migration and tissue healing occurred more rapidly than onto a smooth surface. Others have noted that by creating well-defined micro-textured patterns on a surface, fluid flow at the surface is altered to create discrete regions of low shear stress, which may serve as sanctuaries for cells such as endothelial cells and promote their retention. See S. C. Daxini et al. "Micropatterned polymer surfaces improve retention of endothelial cells exposed to flow-induced shear stress," *Biorheology* 2006 43(1) 45-55.

Texturing in the sub-100 nm range has been observed to increase cell attachment and/or proliferation. See, e.g., the review by E. K. F Yim et al., "Significance of synthetic nanostructures in dictating cellular response," *Nanomedicine: Nanotechnology, Biology, and Medicine* 1 (2005) 10-21, which reported that smooth muscle cells and endothelial cells have improved cell adhesion and proliferation on nanopatterned surfaces. Both types of cells were sensitive to nanotopography. Without wishing to be bound by theory, feature sizes less than 100 nm are believed to allow adhesion of proteins such as fibronectin, laminin, and/or vitronectin to the nanotextured surface, and to provide a conformation for these proteins that better exposes amino acid sequences such as RGD and YGSIR which enhance endothelial cell binding. See, e.g., *Standard handbook of biomedical engineering and design*, Myer Kutz, Ed., 2003 ISBN 0-07-135637-1, p. 16.13. Moreover, nanotexturing increases surface energy, which is believed to increases cell adhesion. See, e.g., J. Y. Lim et al., *J. Biomed. Mater. Res.* (2004) 68A(3): 504-512. In this regard, submicron topography, including pores, fibers, and elevations in the sub-100 nm range, has been observed for the basement membrane of the aortic valve endothelium as well as for other basement membrane materials. See R. G. Flemming et al., *Biomaterials* 20 (1999) 573-588, S. Brody et al., *Tissue Eng.* 2006 Feb.; 12(2): 413-421, and S. L. Goodman et al., *Biomaterials* 1996; 17: 2087-95. Goodman et al. employed polymer casting to replicate the topographical features of the subendothelial extracellular matrix surface of denuded and distended blood vessels, and they found that endothelial cells grown on such materials spread faster and appeared more like cells in their native arteries than did cells grown on untextured surfaces.

An example of a process that may be used to create structures like those shown in FIGS. 3A-3C will now be described. This process is based on a combination of layer-by-layer processing and sol-gel processing. Information on layer-by-layer/sol-gel processing can be found, for example, in "Colloids and Colloid Assemblies," Wiley-VCH, edited by Frank Caruso, ISBN 3-527-30660-9, pp. 266-269; D. Wang and F. Caruso, "Polyelectrolyte-Coated Colloid Spheres as Templates for Sol-Gel Reactions," *Chem. Mater.* 2002, 14, 1909-1913; D. Wang et al., "Synthesis of Macroporous Titania and Inorganic Composite Materials from Coated Colloidal Spheres A Novel Route to Tune Pore Morphology," *Chem. Mater.* 2001, 13, 364-371; and WO 02/074431 to Caruso.

By way of background, it is well known that multilayer coatings can be formed on substrates based on electrostatic self-assembly of charged materials, commonly referred to as the layer-by-layer (LBL) method. In the LBL method, a first layer having a first surface charge is typically deposited on an underlying substrate (in the present invention, a medical device substrate or portion thereof), followed by a second layer having a second surface charge that is opposite in sign to the surface charge of the first layer, and so forth. The charge on the outer layer is reversed upon deposition of each sequential layer. Commonly, 5 to 10 to 25 to 50 to 100 to 200 or more layers are applied in this technique, depending on the desired thickness of the multilayer structure. LBL techniques commonly employ charged species known as "polyelectrolytes," which are polymers having multiple charged groups. Typically, the number of charged groups is so large that the polymers are soluble in polar solvents (including water) when in ionically dissociated form (also called polyions). Depending on the type of charged groups, polyelectrolytes may be classified as polycations (which are generally derived from polyacids and salts thereof) or polyanions (which are generally derived from polybases and salts thereof). Specific examples of polyanions/polyacids include poly(styrene sulfonate) (PSS) (e.g., poly(sodium styrene sulfonate), polyacrylic acid, polyvinylsulfate, polyvinylsulfonate, sodium alginate, eudragit, gelatin, hyaluronic acid, carrageenan, chondroitin sulfate and carboxymethylcellulose, among many others. Specific examples of polycations/polybases include protamine sulfate, poly(allylamine) (e.g., poly(allylamine hydrochloride) (PAH)), polydiallyldimethylammonium species, polyethyleneimine (PEI), polyvinylamine, polyvinylpyridine, chitosan, gelatin, spermidine and albumin, among many others. For further information concerning the LBL process, see, e.g., US 2005/0208100 to Weber et al., and WO/2005/115496 to Chen et al.

It is also well known that ceramic regions may be formed using sol-gel processing techniques. In a typical sol-gel process, precursor materials, typically selected from inorganic metallic and semi-metallic salts, metallic and semi-metallic complexes/chelates, metallic and semi-metallic hydroxides, and organometallic and organo-semi-metallic compounds such as metal alkoxides and alkoxysilanes, are subjected to hydrolysis and condensation reactions in the formation of ceramic materials. Commonly, an alkoxide of choice (e.g., a methoxide, ethoxide, isopropoxide, tert-butoxide, etc.) of a semi-metal or metal of choice (e.g., silicon, aluminum, zirconium, titanium, tin, iron, hafnium, tantalum, molybdenum, tungsten, rhenium, iridium, etc.) is dissolved in a suitable solvent, for example, in one or more alcohols. Subsequently, water or another aqueous solution such as an acidic or basic aqueous solution (which aqueous solution can further contain organic solvent species such as alcohols) is added, causing hydrolysis and condensation to occur. The sol-gel reaction is basically understood to be a ceramic network forming process as illustrated in the following simplified scheme from G. Kickelbick, "*Prog. Polym. Sci.*, 28 (2003) 83-114):

Hydrolysis:

Condensation:

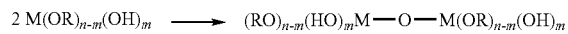

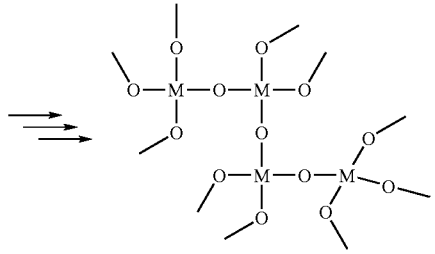

M = Si, Ti, Zr, Sn, Al, ...
R = Me, Et, $^i$Pr, $^n$Pr, $^n$Bu, $^B$Bu, ...

in which the metal/semi-metal atoms (designated generally as M) within the ceramic phases are shown to be linked to one another via covalent linkages, such as M-O-M linkages, although other interactions are also commonly present including, for example, hydrogen bonding due to the presence of hydroxyl groups such as residual M-H groups within the network. Regardless of the exact mechanism, further processing of the so-called "sol" (i.e., a suspension of solid particles within a liquid) enables solid materials to be made in a variety of different forms. For instance, wet "gel" coatings can be produced by spray coating, coating with an applicator (e.g., by roller or brush), ink-jet printing, screen printing, and so forth. The wet gel is then dried to form a ceramic region. Further information concerning sol-gel materials can be found, for example, in G. Kickelbick supra and Viitala R. et al., "Surface properties of in vitro bioactive and non-bioactive sol-gel derived materials," *Biomaterials*, 2002 Aug.; 23(15): 3073-86, and portions of Pub. No. US 2006/0129215 to Helmus et al.

Referring now to FIGS. 5A-5F, a process for the formation of a structure in accordance with the present invention will now be described.

In a first step, a polyelectrolyte multilayer (PML) coating 512 is formed on a substrate 510 using the LBL process. In this regard, certain substrates are inherently charged and thus readily lend themselves to layer-by-layer assembly techniques. To the extent that the substrate does not have an inherent net surface charge, a surface charge may nonetheless be provided. For example, where the substrate to be coated is conductive, a surface charge may be provided by applying an electrical potential to the same. As another example, substrates, including metallic and polymeric substrates, may be chemically treated with various reagents, including reducing agents and oxidizing agents (e.g., sulfur trioxide for sulfonate formation), which modify their surfaces so as to provide them charged groups, such as amino, phosphate, sulfate, sulfonate, phosphonates and carboxylate groups, among many others. Other techniques for providing surface charge include techniques whereby a surface region is treated with a reactive plasma. Surface modification is obtained by exposing a surface to a partially ionized gas (i.e., to a plasma). Because the plasma phase consists of a wide spectrum of reactive species (electrons, ions, etc.) these techniques have been used widely for functionalization of surfaces, including polymeric surfaces among others. Examples include glow discharge techniques (which are conducted at reduced pressure) and coronal discharge techniques (which are conducted at atmospheric pressure), with the former preferred in some cases, because the shape of the object to be treated is of minor importance during glow discharge processes. Lasers may also be used to create a localized plasma in the vicinity of the laser beam (e.g., just above the focal point of the beam). When gases like carbon monoxide (CO), carbon dioxide ($CO_2$), or oxygen ($O_2$) are used, functionalization with —COOH groups (which donate protons to form anionic groups) is commonly observed. When gases like ammonia, a propyl amine, or $N_2/H_2$ are employed, —$NH_2$ groups (which accept protons to form cationic groups) are commonly formed. Functional-group-containing surfaces may also be obtained using plasma polymerization processes in which "monomers" are employed that contain functional groups. Allylamine (which produces —$NH_2$ groups) and acrylic acid (which produces COOH groups) have been used for this purpose. By using a second feed gas (generally a non-polymerizable gas) in combination with the unsaturated monomer, it is possible to incorporate this second species in the plasma deposited layer. Examples of gas pairs include allylamine/$NH_3$ (which leads to enhanced production of —$NH_2$ groups) and acrylic acid/$CO_2$ (which leads to enhanced production of —COOH groups). Further information on plasma processing may be found, for example, in "Functionalization of Polymer Surfaces," Europlasma Technical Paper, May 8, 2004 and in Pub. No. US 2003/0236323. As another example, plasma-based techniques such as those described above may first be used to functionalize a substrate surface, followed by removal of a portion of the functional groups at the surface by exposing the surface to a laser beam, for example, in an inert atmosphere or vacuum in order to minimize deposition. As yet another example, a substrate can be provided with a charge by covalently coupling with species having functional groups with a positive charge (e.g., amine, imine or other basic groups) or a negative charge (e.g., carboxylic, phosphonic, phosphoric, sulfuric, sulfonic, or other acid groups) using methods well known in the art. Further information on covalent coupling may be found, for example, in Pub. No. US 2005/0002865. In many embodiments, a surface charge is provided on a substrate simply by adsorbing polycations or polyanions to the surface of the substrate as a first charged layer. PEI is commonly used for this purpose, as it strongly promotes adhesion to a variety of substrates. Further information can be found in Ser. No. 11/322,905 to Atanasoska et al.

Regardless of the method by which a given substrate is provided with a surface charge, once a sufficient surface charge is provided, the substrate can be readily coated with a layer of an oppositely charged material. Examples of such layers include layers that contain (a) polyelectrolytes, (b) charged particles or (c) both polyelectrolytes and charged particles. Multilayer regions are formed by alternating exposure to solutions containing oppositely charged materials. The layers self-assemble by means of electrostatic layer-by-layer deposition, thus forming a multilayered region over the substrate.

Polyelectrolyte solutions (and particle containing solutions) may be applied by a variety of techniques. These techniques include, for example, full immersion techniques such as dipping techniques, spraying techniques, roll and brush coating techniques, techniques involving coating via mechanical suspension such as air suspension, ink jet techniques, spin coating techniques, web coating techniques and combinations of these processes, among others. Stamping may also be employed, for example, as described in S. Kidambi et al., "Selective Depositions on Polyelectrolyte Multilayers: Self-Assembled Monolayers of m-dPEG Acid as Molecular Templates" *J. Am. Chem. Soc.* 126, 4697-4703, 2004 and Park et al., "Multilayer Transfer Printing for Polyelectrolyte Multilayer Patterning: Direct Transfer of Layer-by-Layer Assembled Micropatterned Thin Films, *Adv. Mater.,*" 2004, 16(6), 520-525.

The choice of the technique will depend on the requirements at hand. For example, deposition or full immersion techniques may be employed where it is desired to apply the species to an entire substrate, including surfaces that are hidden from view (e.g., surfaces which cannot be reached by line-of-sight techniques, such as spray techniques). On the other hand, spraying, roll coating, brush coating, ink jet printing and micro-polymer stamping may be employed, for instance, where it is desired to apply the species only certain portions of the substrate (e.g., on one side of a substrate, in the form of a pattern on a substrate, etc.).

Returning now to FIG. 5A, a substrate 510 is provided with a PML coating 512 as shown, for example, by dipping in consecutive polyelectrolyte regions of opposite charge. The surface charge of the multilayer polyelectrolyte coating 512 at the end of this process is determined by whether the last solution to which the substrate was exposed was a polycationic solution or a polyanionic solution. In some embodiments, at this point, a sol-gel-type process is carried out within the polyelectrolyte layers as described below.

Figure 5A:
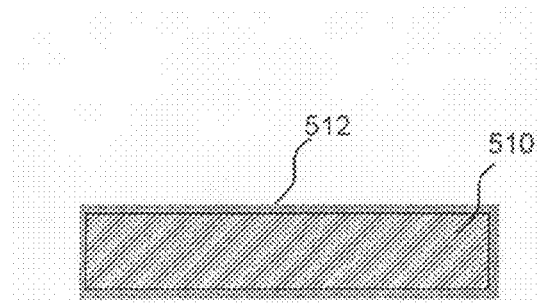
FIGS. 5A-5G are schematic cross-sectional views illustrating articles with ceramic coatings, and processes for forming the same, in accordance with various embodiments of the present invention.
Figure 5B:
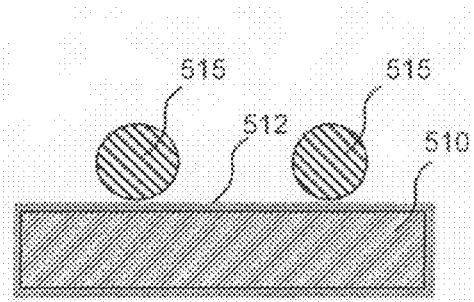
Figure 5C:
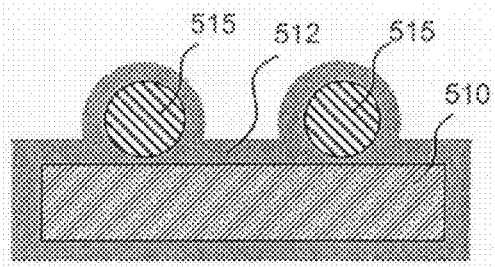

In other embodiments, such as that illustrated in FIGS. 5B-5C, particles of choice are adsorbed to the surface. Typically, a charged particle is used which is either inherently charged or is charged, for example, using one of the techniques described above. For example, particles may be exposed to a solution of PEI to create negatively charged particles. If desired, the charge on a particle can be reversed by exposing it to a solution containing a polyelectrolyte of opposite charge. In some embodiments, a solution of particles may be employed, in which the particles are provided with a polyelectrolyte multilayer coatings. A substrate may, for example, be exposed to a suspension of charged particles using techniques such as those above (e.g., dipping, etc.). The result of this step is illustrated in FIG. 5B, which schematically illustrates the medical device substrate 510, PML coating 512, and charged particles 515. The structure of FIG. 5B is then immersed in further polyelectrolyte solutions of alternating charge, to enclose the charged particles 515 in a PML coating 512. This process also increases the thickness of the polyelectrolyte coating that was previously applied to the substrate 510. The result of this process is illustrated in FIG. 5C.

In some embodiments, a charged therapeutic agent is used to form one or more layers of the PML coating 512. By "charged therapeutic agent" is meant a therapeutic agent that has an associated charge. For example, a therapeutic agent may have an associated charge because it is inherently charged (e.g., because it has acidic and/or or basic groups, which may be in salt form). A therapeutic agent may have an associated charge because it has been chemically modified to provide it with one or more charged functional groups.

For instance, conjugation of water insoluble or poorly soluble drugs, including anti-tumor agents such as paclitaxel, to hydrophilic polymers has recently been carried out in order to solubilize the drug (and in some cases to improve tumor targeting and reduce drug toxicity). Similarly cationic or anionic versions of water insoluble or poorly soluble drugs have also been developed. Taking paclitaxel as a specific example, various cationic forms of this drug are known, including paclitaxel N-methylpyridinium mesylate and paclitaxel conjugated with N-2-hydroxypropyl methyl amide, as are various anionic forms of paclitaxel, including paclitaxel-poly(l-glutamic acid), paclitaxel-poly(l-glutamic acid)-PEO. See, e.g., U.S. Pat. No. 6,730,699; Duncan et al., *Journal of Controlled Release,* 74 (2001)135; Duncan, *Nature Reviews/Drug Discovery*, Vol. 2, May 2003, 347; J. G. Qasem et al, AAPS PharmSciTech 2003, 4(2) Article 21. In addition to these, U.S. Pat. No. 6,730,699, also describes paclitaxel conjugated to various other charged polymers (e.g., polyelectrolytes) including poly(d-glutamic acid), poly(dl-glutamic acid), poly(l-aspartic acid), poly(d-aspartic acid), poly(dl-aspartic acid), poly(l-lysine), poly(d-lysine), poly(dl-lysine), copolymers of the above listed polyamino acids with polyethylene glycol (e.g., paclitaxel-poly(l-glutamic acid)-PEO), as well as poly(2-hydroxyethyl 1-glutamine), chitosan, carboxymethyl dextran, hyaluronic acid, human serum albumin and alginic acid. Still other forms of paclitaxel include carboxylated forms such as 1'-malyl paclitaxel sodium salt (see, e.g. E. W. DAmen et al., "Paclitaxel esters of malic acid as prodrugs with improved water solubility," *Bioorg. Med. Chem.,* 2000 Feb., 8(2), pp. 427-32). Polyglutamate paclitaxel, in which paclitaxel is linked through the hydroxyl at the 2' position to the Δ carboxylic acid of the poly-L-glutamic acid (PGA), is produced by Cell Therapeutics, Inc., Seattle, Wash., USA. (The 7 position hydroxyl is also available for esterification.) This molecule is said to be cleaved in vivo by cathepsin B to liberate diglutamyl paclitaxel. In this molecule, the paclitaxel is bound to some of the carboxyl groups along the backbone of the polymer, leading to multiple paclitaxel units per molecule. For further information, see, e.g., R. Duncan et al., "Polymer-drug conjugates, PDEPT and PELT: basic principles for design and transfer from the laboratory to clinic," *Journal of Controlled Release* 74 (2001) 135-146, C. Li, "Poly(L-glutamic acid)—anticancer drug conjugates," *Advanced Drug Delivery Reviews* 54 (2002) 695-713; Duncan, *Nature Reviews/Drug Discovery, Vol.* 2, May 2003, 347; Qasem et al, AAPS PharmSciTech 2003, 4(2) Article 21; and U.S. Pat. No. 5,614,549.

Using the above and other strategies, paclitaxel and innumerable other therapeutic agents may be covalently linked or otherwise associated with a variety of charged species, including charged polymer molecules (e.g., polyelectrolytes), thereby forming charged drugs and prodrugs which can be assembled in the PML process. Such charged species may be adapted for cleavage from the drug/prodrug prior to administration or upon administration (e.g., due to enzymatic cleavage, etc.).

In a next step, a sol-gel-type process is carried out within the polyelectrolyte layers. For example, the structure of FIG. 5C may be washed in an anhydrous solvent, for example, an anhydrous alcohol. This removes essentially all the water from the structure, except of the water that remains adsorbed within the PML coating 512. The structure is then immersed in a sol-gel precursor solution. For example the structure may be immersed in a solution of a semi-metal or metal alkoxide in anyhydrous alcohol solvent or in a water-alcohol solvent having a high alcohol content (i.e., a solvent in which the water concentration is too low for hydrolysis-condensation reactions to occur). Without wishing to be bound by theory of operation, the high charge density of the polyelectrolyte groups are believed to cause the PML coating 512 to have a water concentration that is higher than that of the surrounding sol-gel precursor solution (e.g., by attracting water molecules out of the sol-gel precursor solution and/or retaining water molecules during washing in anhydrous solvent). Upon diffusion into the PML coating 512, the sol-gel precursor encounters an environment of increase water concentration, in which the hydrolysis and condensation can take place. The PML coating 512 swells, due to the in-situ reaction of the sol-gel precursor within the layers. However, the charge density also decreases due to the swelling, causing a reduction in water concentration, which eventually stops the sol-gel reaction. Regardless of the exact mechanism, the resulting coating, which is a polyelectrolyte/ceramic hybrid coating, is uniformly thick, and its thickness is dependent upon the number of layers within the polyelectrolyte coating (with more layers leading to thicker coatings). The resulting structure is illustrated in FIG. 5D, which shows the substrate 510, particles 515, and polyelectrolyte/ceramic hybrid coating 514.

Figure 5D:
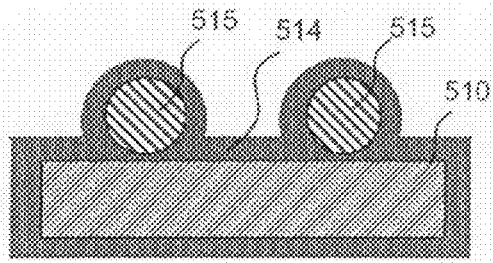
Figure 5E:
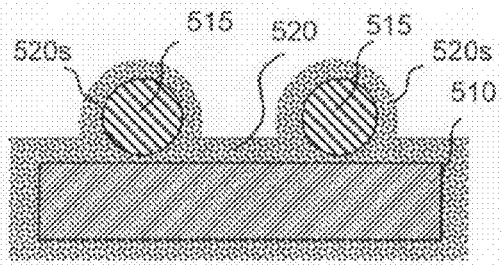
Figure 5F:
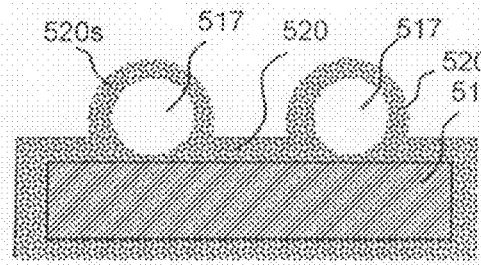
Figure 5G:
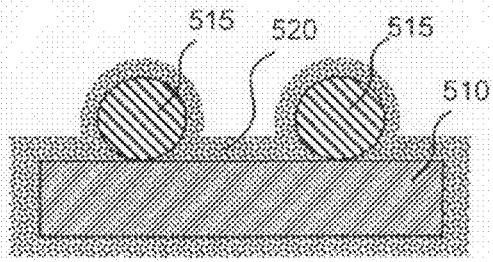

The structure of FIG. 5D may then heated, for example, to a temperature ranging anywhere from about 150° C. to about 600° C. or higher, to form a heat-treated ceramic coating 520 as shown in FIGS. 5E-5G. At the higher end of the range, the ceramic coating 520 has a high proportion of ceramic species (e.g., containing 90 wt % or more ceramic species, for example, from 95 wt % to 98 wt % to 99 wt % to 99.5 wt % to 99.9 wt % or more), with substantially all of the polyelectrolyte component of the coating having been out-gassed from the structure in a process sometimes referred to as calcination. As indicated above, the thickness of the resulting shell will generally be proportional to the number of polyelectrolyte layers that were deposited prior to sol-gel processing. For example, a thickness of about 1 nm per polyelectrolyte layer has been reported in D. Wang and F. Caruso, *Chem. Mater.* 2002, 14, 1909-1913.

As noted above, in some embodiments, carbides and nitrides of metal and semi-metal oxides may be formed, for example, using high-temperature carbothermal reduction or nitridation processes, among others.

At the lower end of the temperature range, the ceramic coating 520 contains substantial amounts of polymeric species (polyelectrolytes) in addition to ceramic species. In such cases, however, the heat treatment will act to strengthen the ceramic coating 520.

In still other embodiments, ceramic coatings may be formed by water-vapor exposure. For example, porous titania-based ($TiO_x$-based) anatase coatings have been formed by exposing sol-gel-derived titania thin films that contained from 0-50 mol % silica to water vapor at 60°-180° C. H. Imai et al., *J. Am. Ceram. Soc.*, 82(9), 1999, 2301-2304. Titanium oxide coatings have been reported to possess photocatalytic properties and a photovoltaic effect. Id. See also Margit J. Jensen et al., *J. Sol-Gel Sci. Techn.* (2006) 39:229-233 who report the preparation of nanocrystalline anatase ($TiO_2$) films, prepared at very low temperature through a sol-gel route using titanium isopropoxide and hydrogen peroxide in ethanol. Crystallization occurred after film deposition at 35° C. in an atmosphere saturated with water vapor. In the present invention, such processing can be employed in conjunction with the sol-gel-swelled PML layers formed as described above. This would allow one, for example, to coat polymeric substrates (as the conditions would not destroy the substrate) with very flexible (as the coating is very thin) hybrid polymer-ceramic coatings.

Lower temperature post-treatment processes such as those above, among others, may also be desirable where therapeutic agents are provided in the PML structure (see above), which therapeutic agents may be harmed at higher temperatures.

Depending upon the heat-treatment temperature and atmosphere, and upon the nature of the material forming the particles 515 of FIG. 5D, the heat-treatment process either will not result in the removal of the particle forming material (although, in some cases, resulting in a chemical modification of the particles), leaving the particles 515 encased in ceramic shells 520s as illustrated in FIG. 5E, or it will result in the partial or complete removal of the particle forming material, thereby creating ceramic shells 520s with partially or wholly hollow interiors 517 as shown in FIG. 5F.

Particle removal may also be conducted independently of heat treatment, for example, in the absence of heat treatment, prior to heat treatment, or after heat treatment (where the heat treatment does not remove the particles). For instance, particles may be removed via a dissolution process. As specific examples, polymeric particles may be removed using organic solvents (e.g., removal of polystyrene particles by tetrahydrofuran), and inorganic particles may be removed using acidic or basic aqueous solutions (e.g., removal of silica particles using HF).

In some embodiments, hybrid template particles are employed in which a portion of each particle is removed (e.g., by heat treatment, dissolution, etc.) and a portion of each particle remains within the hollow ceramic shell. One example of such a particle is a polystyrene sphere that contains one or more smaller paramagnetic particles (e.g., paramagnetic particles within a polystyrene matrix, a paramagnetic particle core with a polystyrene shell, etc.). The polystyrene portion of such a particle can be removed, for instance, by heat or by organic solvent dissolution.

Turning now to the structure of FIG. 5G, this structure is formed by a process like that used to form FIG. 5E, except that the charged particles 515 are electrostatically deposited onto the substrate 510 without first coating the substrate 510 with a polyelectrolyte multilayer coating (as is done in FIG. 5A), the result being that the particles 515 in the structure of FIG. 5G are in closer proximity to the substrate 510 than are the particles 515 of FIG. 5E.

In some embodiments, ceramic coatings in accordance with the present invention are provided over the entire surface of a substrate. In some embodiments, ceramic coatings in accordance with the present invention are provided over only a portion of the surface of a substrate (e.g., only a luminal stent surface, only an abluminal stent surface, only abluminal and side stent surfaces, etc.). Substrates may be partially coated, for example by exposing the various solutions employed (e.g., polyelectrolyte solutions, particle solutions, sol-gel solutions) to only a portion of the substrate. Examples of techniques for doing so include the use of masking, partial dipping, roll-coating (e.g., where it is desired to apply the coating to the abluminal surface of a tubular device such as a stent) or other transfer coating technique, including the use of a suitable application device such as a brush, roller, stamp or ink jet printer, among other techniques.

Due to the straightforward nature of LBL processing and due the fact that non-charged materials may be charged using a variety of techniques, a wide range of substrate and particle materials may be employed for the practice of the present invention.

Suitable substrate materials therefore may be selected from a variety of materials, including (a) organic materials (e.g., materials containing organic species, commonly 50 wt % or more organic species) such as polymeric materials and (b) inorganic materials (e.g., materials containing inorganic species, commonly 50 wt % or more inorganic species) such as metallic materials (e.g., metals and metal alloys) and non-metallic inorganic materials (e.g., carbon, semiconductors, glasses, metal- and non-metal-oxides, metal- and non-metal-nitrides, metal- and non-metal-carbides, metal- and non-metal-borides, metal- and non-metal-phosphates, and metal- and non-metal-sulfides, among others). Suitable substrate materials include biostable materials and biodisintegrable materials (i.e., materials that, upon placement in the body, are dissolved, degraded, resorbed, and/or otherwise removed from the placement site).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium, as well as other metals such as those listed above as examples of ceramic species); silicon; silicon-based materials, such as those containing silicon nitrides, silicon carbides and silicon oxides (sometimes referred to as glass ceramics); calcium phosphate ceramics (e.g., hydroxyapatite); carbon and carbon-based, ceramic-like materials such as carbon nitrides, among many others.

Specific examples of metallic inorganic materials may be selected, for example, from substantially pure biostable and biodisintegrable metals (e.g., biostable metals such as gold, platinum, palladium, iridium, osmium, rhodium, titanium, tantalum, tungsten, and ruthenium, and biodisintegrable metals such as magnesium, zinc and iron) and biostable and biodisintegrable metal alloys, for example, biostable metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), and biodisintegrable metal alloys such as magnesium alloys, zinc alloys, and iron alloys (including their combinations with one another, Ce, Ca, Zn, Zr and Li, among other elements—see Pub. No. US 2002/0004060 to Heublein et al.), among many others.

Specific examples of organic materials include biostable and biodisintegrable polymers, which may be selected, for example, from the following, among others: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

Particles for use in the present invention varying widely in composition, size and shape (e.g., spheres, polyhedra, cylinders, tubes, fibers, ribbon-shaped particles, plate-shaped particles, and other regular and irregular particle shapes).

In general, the distance across the particles as-deposited (e.g., the diameter for spheres, cylinders and tubes, the width for other particles including plates, ribbon-shaped particles, fibers, polyhedra, and other regular and irregular particles) is less than 100 microns (µm) (the length is frequently much larger), ranging, for example, from 100 microns or more to 50 microns to 25 microns to 10 microns to 5 microns to 2 microns to 1 micron to 500 nm to 250 nm to 100 nm to 50 nm to 25 nm or less. In certain embodiments, the particles are sub-micron-particles in the sense that the distance across the particles as-deposited is less than 1000 nm, and more typically less than 100 nm.

Suitable materials for the particles can be selected from the organic and inorganic materials set forth above for use as substrate materials. Further examples of particles, which are not exclusive of those materials, may be selected from polymer microspheres, including polymethyl methacrylate (PMMA) microspheres and polystyrene microspheres, such as those available from Microparticles, Berlin, Germany (http://www.microparticles.de/product_palette.html), among many others, alumina particles, titanium oxide particles, tungsten oxide particles, tantalum oxide particles, zirconium oxide particles, silica particles, silicate particles such as aluminum silicate particles, synthetic or natural phyllosilicates including clays and micas (which may optionally be intercalated and/or exfoliated) such as montmorillonite, hectorite, hydrotalcite, vermiculite and laponite, and needle-like clays such as attapulgite, and further including particulate molecules such as polyhedral oligomeric silsequioxanes (POSS), including various functionalized POSS and polymerized POSS, polyoxometallates (e.g., Keggin-type, Dawson-type, Preyssler-type, etc.), fullerenes (e.g., "Buckey balls"), carbon nanofibers, single-wall carbon nanotubes and multi-wall carbon nanotubes (including so-called "few-wall" nanotubes).

In some embodiments, one or more therapeutic agents are disposed within the particles.

As noted above, in some embodiments, a polymeric coating (e.g., a therapeutic-agent-eluting coating, a lubricious coating, etc.) may be disposed over all or a portion of a ceramic coating in accordance with the invention. As used herein a polymeric coating is one that comprises a single polymer or a mixture differing polymers, for example, comprising from 50 wt % or less to 75 wt % to 90 wt % to 95 wt % to 97.5 wt % to 99 wt % or more of one or more polymers. The polymer(s) may be biostable or biodisintegrable. Polymers suitable for this purpose may be selected, for example, from one or more of the polymers set forth above for use as substrate materials. Further examples of polymers, which are not exclusive of those materials, include thermoplastic elastomers such as poly(styrene-co-isobutylene) block copolymers, poly(methyl methacrylate-co-butyl acrylate) block copolymers and thermoplastic polyurethanes, fluoropolymers such as PTFE, FEP, ETFE and PVDF, crosslinked hydrogels such as crosslinked thiolated chondroitin sulfate, polyacrylic acid, polyvinyl alcohol or polyvinyl pyrrolidone, polyanhydrides including aliphatic polyanhydrides such as poly(sebacic acid) or poly(adipic acid), unsaturated polyanhydrides such as poly(4,4'-stilbenedicarboxylic acid anhydride), aromatic polyanhydrides such as poly(terephthalic acid), copolymers of the foregoing anhydrides with one another, including poly(aliphatic-aromatic anhydrides), and copolymers of the foregoing anhydrides with other monomers, including poly(ester anhydrides) and poly(ether anhydrides), fatty acid based anhydrides, terminated polyanhydrides, branched polyanhydrides, crosslinked polyanhydrides, and amino acid based polyanhydrides, see, e.g., N. Kumar et al., "Polyanhydrides: an overview," *Advanced Drug Delivery Reviews* 54 (2002) 889-910, biodegradable polyesters such as polylactide and poly(lactide-co-glycolide), among many others, as well as blends of the foregoing.

The thickness of the therapeutic-agent-eluting polymeric coating may vary widely, typically ranging from 25 nm or less to 50 nm to 100 nm to 250 nm to 500 nm to 1 µm to 2.5 µm to 5 µm to 10 µm to 25 µm to 50 µm to 100 µm or more in thickness. As noted above, in some embodiments, the thickness of the polymeric coating is dictated by the size of the ceramic shells that are present on the surface, whereas in others it is not.

In some embodiments, the polymeric coating is a therapeutic-agent-eluting polymeric coating. As used herein, a "therapeutic-agent-eluting polymeric coating" is a coating that comprises a therapeutic agent and a polymer and from which at least a portion of the therapeutic agent is eluted, for example, upon contact with a subject, or upon implantation or insertion into a subject. The therapeutic-agent-eluting polymeric coating will typically comprise, for example, from 1 wt % or less to 2 wt % to 5 wt % to 10 wt % to 25 wt % to 50 wt % or more of a single therapeutic agent or of a mixture of therapeutic agents within the coating. Therapeutic agents may be selected, for example, from those listed below, among others.

Polymeric coatings may be applied using any suitable method. For example, where the coating contains one or more polymers having thermoplastic characteristics, the coating may be formed, for instance, by (a) providing a melt that contains polymer(s) and any other optional species such as therapeutic agent(s), as desired, and (b) subsequently cooling the melt. As another example, the coating may be formed from a curable composition (e.g., a UV curable composition), for instance, by (a) providing a curable composition that contains polymer(s), curing agents, and any other optional species such as therapeutic agent(s), as desired, and (b) curing the composition. As yet another example, a coating may be formed, for instance, by (a) providing a solution or dispersion that contains one or more solvent species, polymer(s), and any other optional species such as therapeutic agent(s), as desired, and (b) subsequently removing the solvent species. The melt, solution or dispersion may be applied, for example, by roll-coating (e.g., where it is desired to apply the coating to the abluminal surface of a tubular device such as a stent) or other transfer coating technique, including application using a suitable application device such as a brush, roller, stamp or ink jet printer, by dipping, and by spray coating, among other methods.

A wide variety of therapeutic agents may be employed in conjunction with the present invention, including genetic therapeutic agents, non-genetic therapeutic agents and cells, which may be used for the treatment of a wide variety of diseases and conditions.

Suitable therapeutic agents for use in connection with the present invention may be selected, for example, from one or more of the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (o) agents that interfere with endogenous vasoactive mechanisms, (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists such as rosiglitazone, pioglitazone, netoglitazone, fenofibrate, bexaotene, metaglidasen, rivoglitazone and tesaglitazar, (bb) prostaglandin E agonists such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4.

Preferred non-genetic therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Numerous therapeutic agents, not necessarily exclusive of those listed above, have been identified as candidates for vascular and other treatment regimens, for example, as agents targeting restenosis. Such agents are useful for the practice of the present invention and suitable examples may be selected from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein), SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, and (cc) blood rheology modulators such as pentoxifylline.

Further therapeutic agents useful for the practice of the present invention are also disclosed in U.S. Pat. No. 5,733,925 to Kunz et al.

Additional embodiments will now be discussed with reference to the drawings.

Figure 6A:
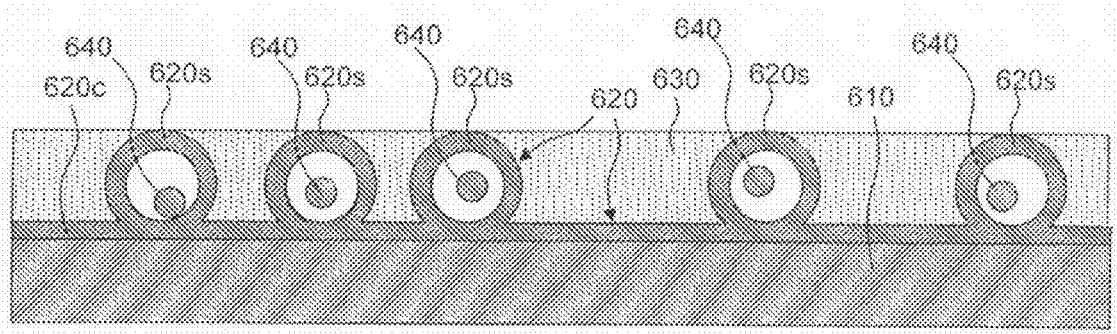
FIGS. 6A and 6B are schematic cross-sectional views of articles in accordance with two embodiments of the present invention.

The structure shown in the schematic, cross-sectional illustration of FIG. 6A is similar to those described in FIGS. 4A and 4B in that it includes a substrate 610, having disposed thereon a ceramic coating 620 in accordance with the invention, which includes raised ceramic shells 620s connected by a ceramic layer 620c that is conformal with the substrate 610. A polymeric coating 630 is shown, disposed over the ceramic region 620, which in this embodiment contains a therapeutic agent. Unlike FIGS. 4A and 4B, however, the hollow ceramic shells 620s of FIG. 6A contain paramagnetic particles 640. Paramagnetic particles may be selected from various paramagnetic materials, which are typically metals, alloys or compounds of certain transition, rare earth and actinide elements (e.g., iron, iron oxides including magnetite, etc.).

Such a structure may be formed, for example, using polymeric particles (e.g., polystyrene spheres) that contain embedded paramagnetic particles as templates for the above-described LBL/sol-gel process. After removing the polystyrene component of the spheres (e.g., by heat treatment or dissolution), the paramagnetic particles remain inside of the ceramic shells 620s. The paramagnetic particles 640 are separated from the exterior environment by the ceramic shells 620s. Because they are paramagnetic, one can vibrate these particles 640 inside of their ceramic shells 620s using an external magnetic field. This will cause heat, which can, for example, increase the rate at which the therapeutic agent is released from the polymeric coating, among other effects. As an alternative embodiment, a magnetic material (e.g., one of those above) is placed on the outside of the polymeric particles (e.g., polystyrene particles may be provided, which have a magnetite coating). See, e.g., Marina Spasova et al., "Magnetic and optical tunable microspheres with a magnetite/gold nanoparticle shell," *J. Mater. Chem.*, 15, (2005) 2095-2098 for more information. As above, in these embodiments, the magnetic material is embedded with the ceramic shells that are ultimately formed.

Figure 6B:
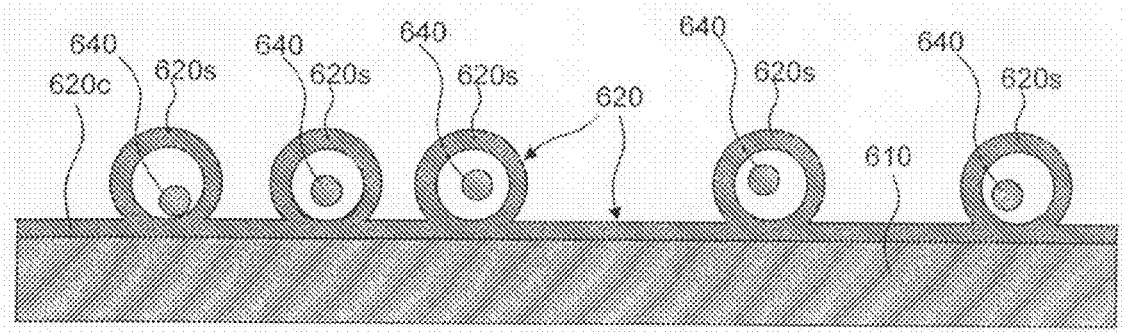

FIG. 6B is a structure like that of FIG. 6A, albeit without the polymeric coating 630. Like the structure of FIG. 6A, this structure can be heated using an external magnetic field. The high temperatures generated can be used, for example, to cause necrosis, thrombosis and other physiological effects within the body. For example, a coating like that shown in FIG. 6B may be provided on an embolic coil for the treatment of an aneurism. After implantation into an aneurism, the coil can be heated, thereby causing thrombosis within the aneurism.

As noted above, structures far more complex than those of FIGS. 4A, 4B and 6A can be formed in accordance with the invention, which are capable of creating greater degrees of interlock between the ceramic coatings and the polymeric coatings overlying them.

Figure 7A:
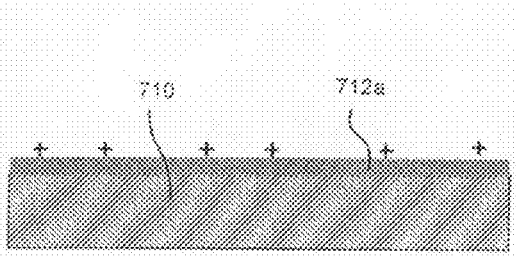
FIGS. 7A-7H, 8A-8C and 9A-9D are schematic cross-sectional views illustrating articles in accordance with various embodiments of the present invention and processes for forming the same.

In one embodiment, such a structure is produced using two sizes of charged particles. For example, with reference to FIGS. 7A-7E, in a first step, a PML coating 712a is formed on a substrate 710 using the LBL process (e.g., by dipping into polyelectrolyte solutions of alternating charge). In the embodiment shown in FIG. 7A, the top polyelectrolyte layer of the polyelectrolyte multilayer coating 712a is positively charged. In a subsequent step, spherical particles 715b, each comprising a PML coating 712b whose top layer is negatively charged, are electrostatically assembled onto the PML coating 712a as shown in FIG. 7B.

Figure 7B:
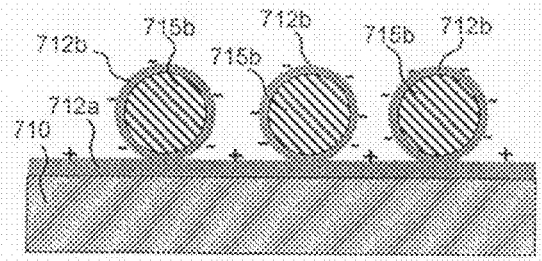
Figure 7C:
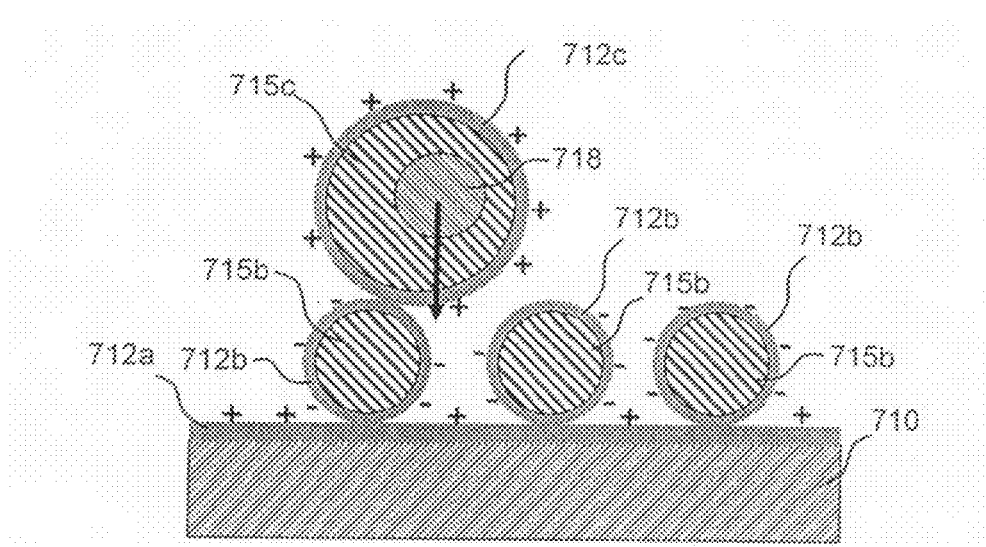
Figure 7D:
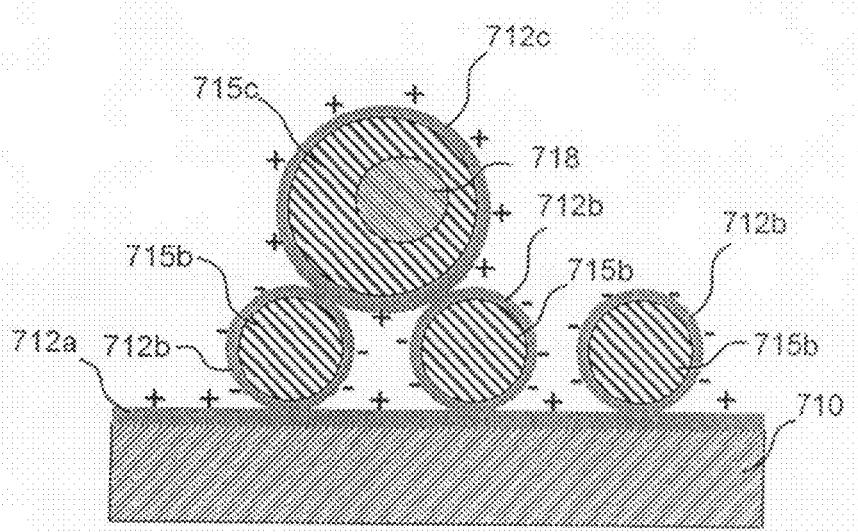
Figure 7E:
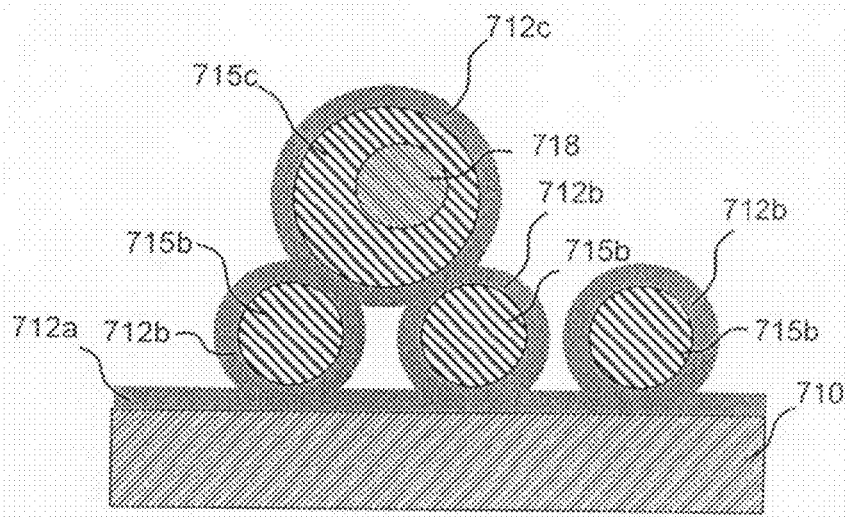

Next spherical particles 715c, each comprising a PML coating 712c whose top layer is positively charged, are electrostatically assembled on the structure of FIG. 7B. The resulting structure is illustrated in FIG. 7C. Particles 715c are larger than particles 715b. Moreover, one or more paramagnetic kernels 718 lies within each particle 715c in the embodiment shown. As a specific example, polystyrene spheres 715b, 715c may be employed. For instance smaller spheres having diameters of 200 nm and larger spheres having diameters of 500 with super-paramagnetic kernels may be purchased from Microparticles, Berlin, Germany. By subjecting the kernels 718 to a magnetic field, a magnetic force is generated (illustrated by the arrow in FIG. 7C), and the coated particles 715c are urged into a closer association with the underlying coated particles 715b as shown in FIG. 7D. This improves the likelihood that the larger coated particles 715c make contact with several smaller coated particles 715b, rather than just hanging onto one sphere only. Compare FIGS. 7C and 7D.

The structure of FIG. 7D can then be subjected to further polyelectrolyte deposition steps (e.g., by dipping into polyelectrolyte solution of alternating charge) to increase the thickness of the various PML coatings 712a,712b,712c as desired and to better merge them into a single continuous PML structure. The result is a structure like that of FIG. 7E. Next, a sol-gel-type process is carried out within the PML structure, using sol-gel precursor solutions as discussed above, thereby forming a polyelectrolyte/ceramic hybrid structure 714 as shown in FIG. 7F.

Figure 7F:
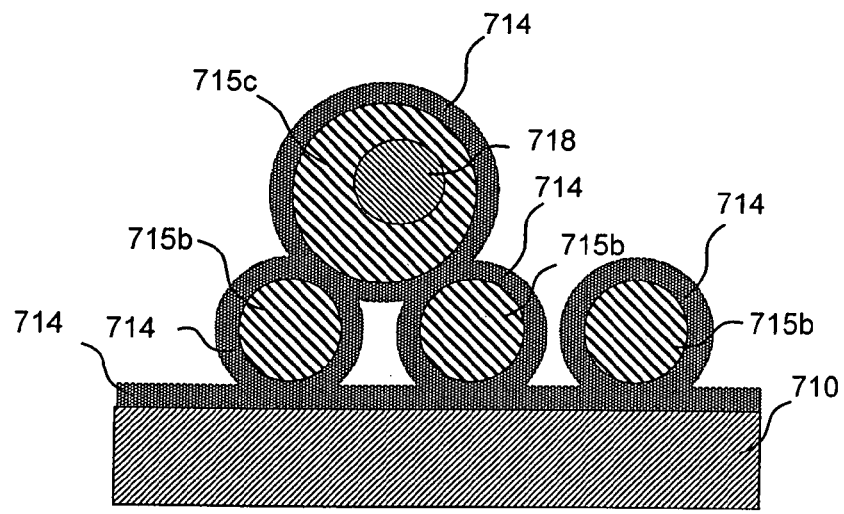

The structure of FIG. 7F may then be subjected to further processing to remove the particles 715b and 715c. For example, assuming that the particles 715b and 715c are polymeric in nature (e.g., polystyrene), the structure of FIG. 7F may be heated to a temperature sufficient to substantially remove the polymeric particles 715b and 715c (and the polymeric components of the polyelectrolyte/ceramic hybrid structure 714 as well), thereby creating the ceramic coating 720 shown in FIG. 7G. The coating 720, which is a continuous structure, includes a substrate covering portion 720c and numerous ceramic shells 720s. Within the large ceramic shells 720 are found paramagnetic kernels 718, which can now be used to heat the medical device in vivo (or ex vivo), if desired.

Figure 7G:
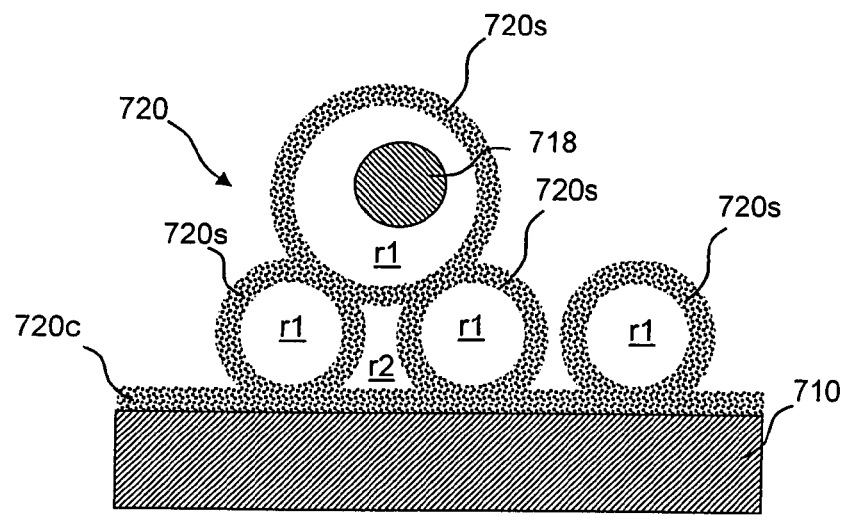
Figure 7H:
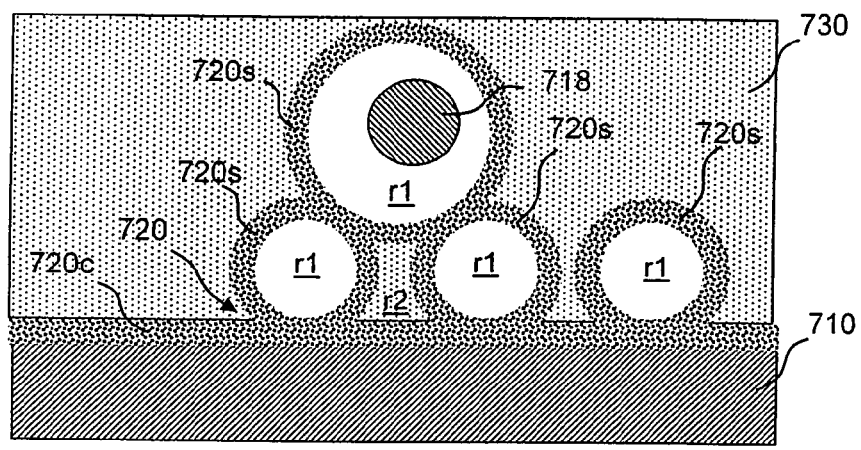

Note that the structure of FIG. 7G contains spaces r1 that are completely encapsulated/surrounded by the ceramic shells 720s as well as spaces r2 that are open to the outer environment. In the event that a polymeric coating 730 is applied as shown in FIG. 7H, the spaces r2 afford the polymeric coating 730 the opportunity to form a fully interlocking interface with the ceramic coating 720.

In another embodiment, the large spheres described in the prior embodiment can be replaced with elongated particles such as carbon nanofibers or carbon nanotubes, among many others. As with the large spheres above, the elongated particles are overcoated with PML coatings. For example, one can employ polyelectrolyte-functionalized carbon nanotubes or one can employ carbon nanotubes with PML coatings as described in H. Kong et al. "Polyelectrolyte-functionalized multiwalled carbon nanotubes: preparation, characterization and layer-by-layer self-assembly," *Polymer* 46 (2005) 2472-2485. Following steps like those described above to create the structure of FIG. 7C (except using elongated particles rather than large spheres, and without the use of magnetic force), one ends up with a bottom layer of small spheres of a first charge, connected by elongated particles having an opposite charge. Further processing as described in FIGS. 7E-7G above (polyelectrolyte deposition, exposure to a sol-gel precursor, heat treatment) results in a structure like that illustrated in FIG. 8A. Like FIG. 7G, FIG. 8A includes a substrate 810, having disposed thereon a continuous ceramic coating 820 in accordance with the invention. The region 820 includes raised ceramic hollow spherical shells 820$s$1 connected by a ceramic layer 820$c$ that is conformal with the substrate 810. Unlike FIG. 7G, however, the continuous ceramic coating 820 of FIG. 8A further includes non-hollow, non-spherical ceramic shells 820$s$2, which contain elongated particles 815. For example, the elongated particles may be carbon fibers, carbon nanotubes or any other elongated particle that survives processing. As can be seen from FIG. 8A, these ceramic-coated fibers 815,820$s$2 connect the hollow ceramic spheres 820$s$1 to one another. Alternatively, elongated particles may be used which are removed during the heat treatment process, in which case a structure like that in FIG. 8B would result, wherein hollow ceramic fibers 820$s$2 connect the hollow ceramic spheres 820$s$1 to one another. Because thin fibers are used to interconnect the underlying ceramic spheres (rather than larger ceramic spheres, as was the case in FIG. 7G), a structure like that of FIGS. 8A and 8B should be more tolerant of bending or flexing that the structure of FIG. 7G.

Figure 8A:
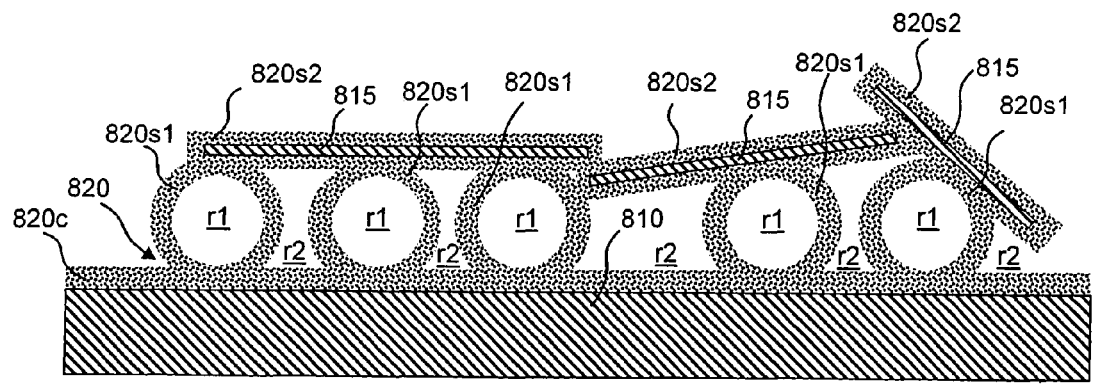
Figure 8B:
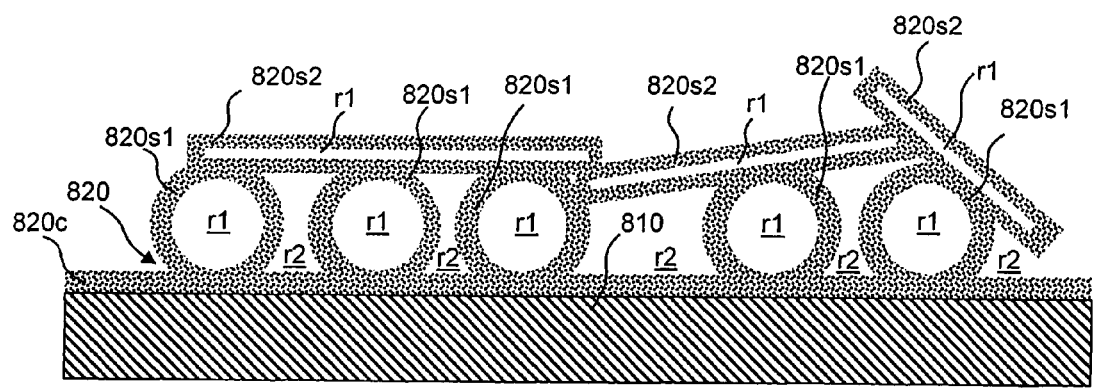
Figure 8C:
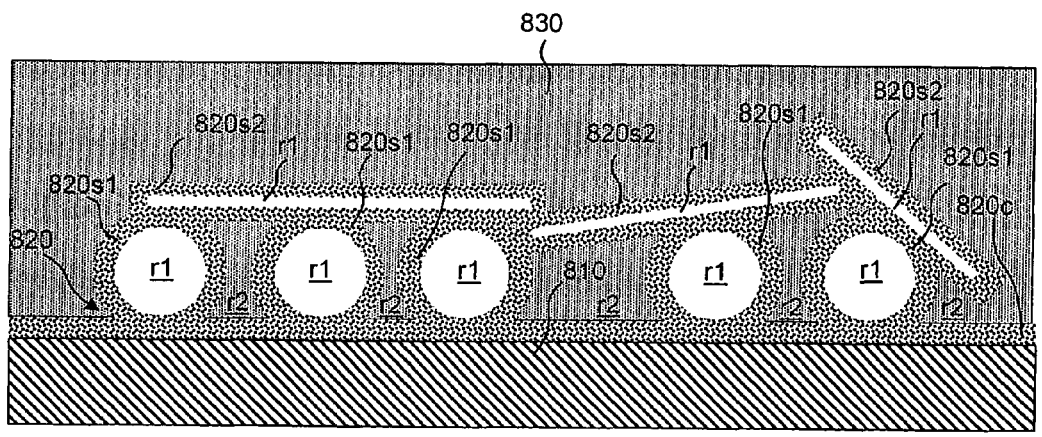

As with FIG. 7G, the structures of FIGS. 8A and 8B, contains spaces r1 that are completely encapsulated/surrounded by ceramic shells (i.e., shells 820$s$1,820$s$2), as well as spaces r2 that are open to the outer environment. These spaces r2 afford a polymeric coating 830 the opportunity to form a fully interlocking interface with the ceramic coating 820 as seen in FIG. 8C.

In other embodiments of the invention, the use of spheres is completely eliminated. For example, for example, one could apply to a charged substrate (e.g., an LBL coated substrate) a layer of elongated particles of opposite charge (e.g., LBL encapsulated particles), which particles may be, for example, heat-resistant particles such as a carbon nanotubes or heat-labile particles such as polystyrene fibers, among many other possibilities. After adsorbing the particles, LBL processing, sol-gel processing, and heat treatment may be conducted (see above) to produce a ceramic coating, containing raised ceramic shells, which may contain the elongated particles, or which may be wholly or partially hollow.

In a variation of this embodiment, one could apply to a substrate (e.g., an LBL coated substrate) having a given charge (e.g., a negative charge), a first layer of elongated particles (e.g., LBL coated particles) of opposite charge (e.g., a positive charge), followed by a second layer of elongated particles (e.g., LBL coated particles) of opposite charge (e.g., a negative charge), and so forth. These steps may be followed by further LBL polyelectrolyte processing, sol gel processing, and heat treatment. Such a process would create a relatively random orientation for the elongated particles, creating a complex mesh of raised ceramic shells (which shells, again, may be filled with the elongated particles or partially or wholly hollow).

A more regular architecture may be created by using an AC electric field to orient the elongated particles within the solution at the time of deposition. For example, carbon nanotubes are known to align themselves as a result of the formation of an induced dipole in response to an electric field. A DC field will align and move the nanotubes, whereas an AC field only aligns them. In this regard, see, e.g., M. Senthil Kumar et al., "Influence of electric field type on the assembly of single walled carbon nanotubes," *Chemical Physics Letters* 383 (2004) 235-239. See also U.S. Ser. No. 11/368,738. For example, using electric field alignment, the particles of the various layers may all be aligned in a single direction. As another example, electrical field alignment may be used to align the positively and negatively charged layers orthogonally with respect one another. These steps may, again, be followed by LBL polyelectrolyte processing, sol-gel processing and heat treatment, thereby forming a strongly connected ceramic network with internal reinforcement based on carbon nanotubes.

Figure 9A:
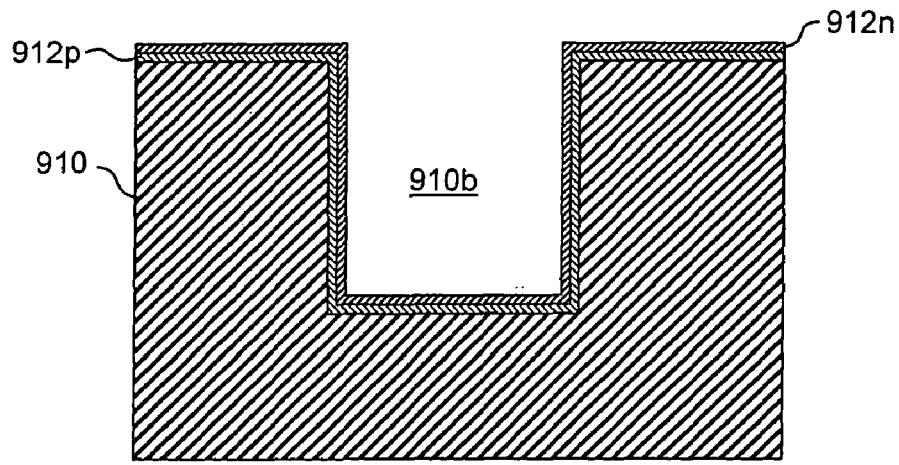

A further embodiment of the invention is illustrated in conjunction with FIGS. 9A-9D. As shown in FIG. 9A, a substrate 910 having one or more depressions (e.g., blind holes 910$b$) is coated with a PML coating. Two layers are schematically illustrated in FIG. 9A, an inner positive polyelectrolyte layer 912$p$ and an outer negative polyelectrolyte layer 912$n$, although a single layer, or three or more layers may be applied. Moreover, the outer layer can be a positive layer, rather than a negative layer as illustrated. The substrate may be, for example, a stent within which numerous blind holes are formed (e.g., via laser ablation).

Figure 9B:
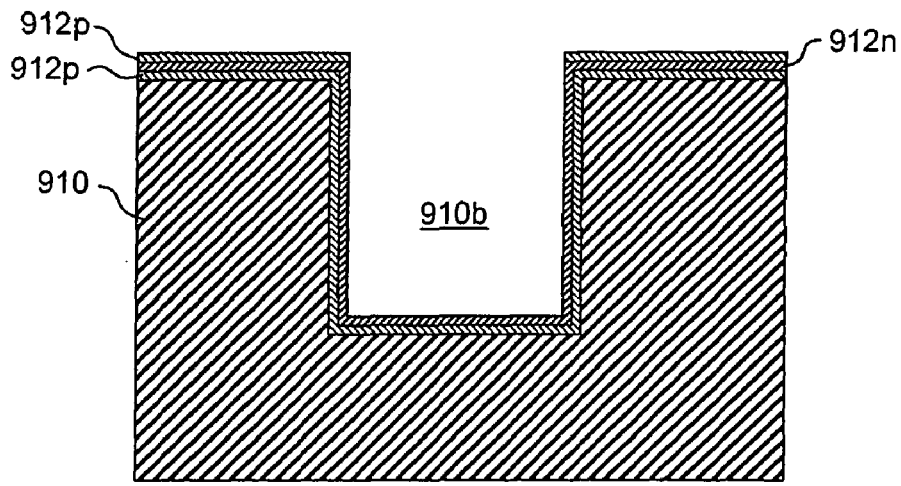
Figure 9C:
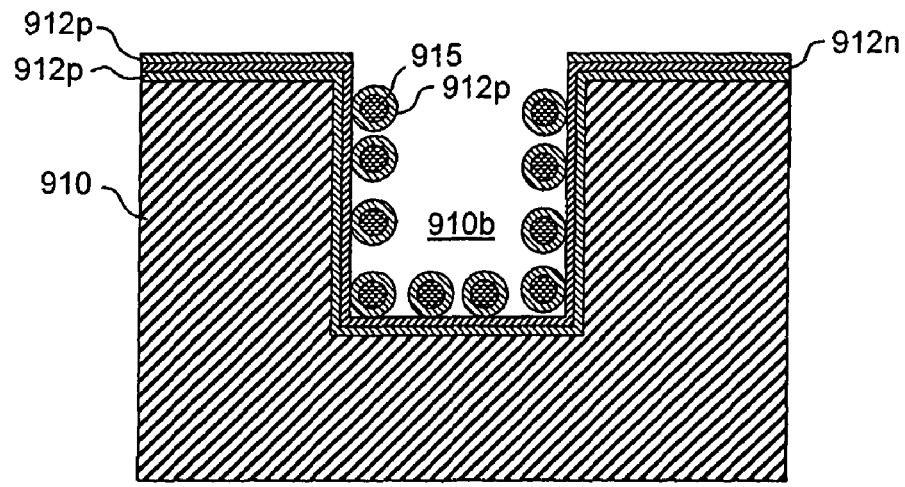
Figure 9D:
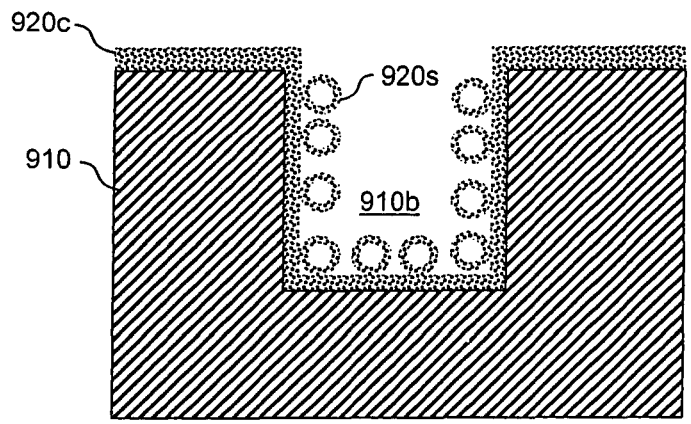

In a subsequent step, a positive polyelectrolyte layer 912$p$, or multiple alternating polyelectrolyte layers terminating in a positive polyelectrolyte layer, is/are selectively applied to those portions of the negative polyelectrolyte layer 912$n$ layer over the upper substrate surface, but not those portions within the blind hole 910$b$, resulting in a structure like that of FIG. 9B. This structure has a negative surface charge within the blind hole 919$b$ and a positive surface charge outside the blind hole. (In the event that the structure in FIG. 9A were to have an outer positive layer, charges for this step would be reversed, such that the surface of the blind hole would have a positive surface charge and the upper surface of the structure would have a negative surface charge.) An example of a technique by which such selective application may be achieved is described in J. Park et al., *Adv. Mater.*," 2004, 16(6), 520-525, which describes a technique in which a PML coating is adsorbed onto the surface of a polymer (polydimethylsiloxane) stamp. The first layer adsorbed onto the stamp is cationic polyallylamine hydrochloride (PAH), followed by alternating layers of anionic sulfonated polystyrene (SPS) and cationic polydiallyldimethylammonium chloride (PDAC). The last layer is the cationic PDAC. The stamp is then contacted with a substrate having a negative surface charge and the multilayer is transferred in its entirety from the stamp to the substrate. The top layer of the transferred pattern is the anionic PAH layer.

At this point, the structure of FIG. 9B is exposed to particles having a negative surface charge. In the embodiment shown in FIG. 9C, the particles are spheres 915 with PML coating layers, terminating in a positively charged polyelectrolyte layer 921p. As elsewhere herein, the structure of FIG. 9C can then be optionally provided with additional polyelectrolyte layers as desired, followed by sol-gel processing and heat treatment to produce a structure like that of FIG. 9D, which includes a substrate 910 having a ceramic coating that includes raised ceramic shells 920s (in FIG. 9D the shells are hollow, although they need not be, as note elsewhere herein) connected by a ceramic layer 920c that is conformal with the substrate. In this example, the raised ceramic shells 920s are found only in the blind holes.

Figure 10A:
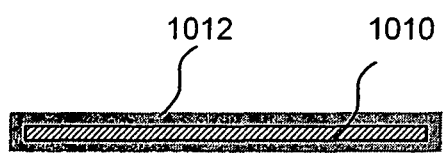
FIGS. 10A-10C are schematic cross-sectional views illustrating a process for forming a ceramic coated carbon nanotube, in accordance with the present invention.
Figure 10B:
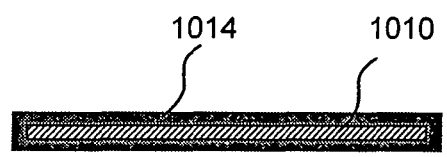
Figure 10C:
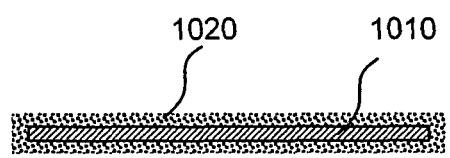

In another aspect of the invention, the use of a substrate is eliminated entirely, and the resulting product is a collection of carbon nanotubes coated with a ceramic layer. For example, with reference to FIG. 10A, a carbon nanotube 1010 can be provided with a polyelectrolyte multilayer coating 1012. This structure is then exposed a sol-gel precursor, forming a polyelectrolyte/ceramic hybrid coating 1014 as shown in FIG. 10B, followed by heat treatment to create carbon nanotubes 1010 with a ceramic coating 1020 as shown in FIG. 10C. Such carbon nanotubes would have applications in many fields, for example, finding use as reinforcement particles in polymers or metals. Carbon nanotubes normally are at risk for agglomeration due to π-π bonding, which is disrupted by the ceramic coating.

Example 1

A procedure for creating a coating like that illustrated in FIG. 3B will now be described.

Solutions are prepared as follows (a) PAH solution: a solution of poly(allylamine hydrochloride) (PAH) (m.w. ~70,000) (Sigma-Aldrich) was made in DI water with the following constituents: 1 g/L PAH, 0.2M NaCl, and 0.05M NaAc (sodium acetate buffer solution pH=5.6), (b) PSS solution: a solution of poly(sodium 4-styrenesulfonate) (PSS) (m.w. ~70,000) (Sigma-Aldrich) was made in DI water with the following constituents: 1 g/L PSS, 0.2M NaCl, 0.05M NaAc (sodium acetate buffer solution pH=5.6), (c) polystyrene (PS) particle solution: a solution of poly(sodium 4-styrenesulfonate) particles (500 nm) (Forschungs-und Entwicklungslaboratorium, Berlin, Germany) was received as a concentrated solution (5 wt %) and diluted in deionized (DI) water to a concentration of 0.5 wt %, (d) sol-gel solution: 2 g TEOS (Alfa Aesar, Johnson Matthey Catalog Company, Inc., Ward Hill, Mass., USA) is combined with 100 mL Ethanol (Anhydrous, Denatured, product no. EX0285-3, EMD Chemicals, Gibstown, N.J., USA) and mixed for 10 minutes, after which are added 10 mL DI water and 1 mL ammonium hydroxide (25% in water) (Sigma-Aldrich), followed by further mixing.

Stainless steel 316L electro-polished coupons (3.5"×0.79"×0.03") are cleaned with an RF oxygen plasma in a March AP-1000 Plasma System using the following process parameters: P=200 mTorr, 300 watts, Gas 1 (Argon)=250 sccm, Gas2 (Oxygen)=200 sccm, t=180s.

The coupon is provided with 1.5 bi-layers (PAH/PSS/PAH), followed by a PS particle layer, followed by 1.5 bilayers (PAH/PSS/PAH). The resulting structures are analogous to those shown schematically in FIGS. 5A-5C (described above). For each polyelectrolyte layer, the coupon is immersed in a beaker of PAH or PSS solution (prepared as described above) and agitated on a shaker for 20 minutes. For the PS particle layer, the coupon is immersed in a beaker of the PS particle solution (prepared as described above) and agitated on a shaker for 1 hour. Three DI water rinses are performed after each layer to remove non-adsorbed polyelectrolyte/particles and the coupon is placed directly into the next solution.

This structure is then submerged in a beaker of sol-gel solution (prepared as described above) for approximately 16 hours. Three DI water rinses are performed after exposure to the sol-gel solution. The resulting structure, which is analogous to that shown schematically in FIG. 5F (described above), is placed in an oven at ambient temperature and ramped to a final temperature of 540° C. over a period of ~1.5 hrs. After a total cycle time of 6 hrs (ramp-up and 540° C. hold), the oven is turned off, and the sample is allowed to cool in the oven overnight. The final structure is analogous to that shown schematically in FIG. 5F (described above).

Example 2

Figure 11:
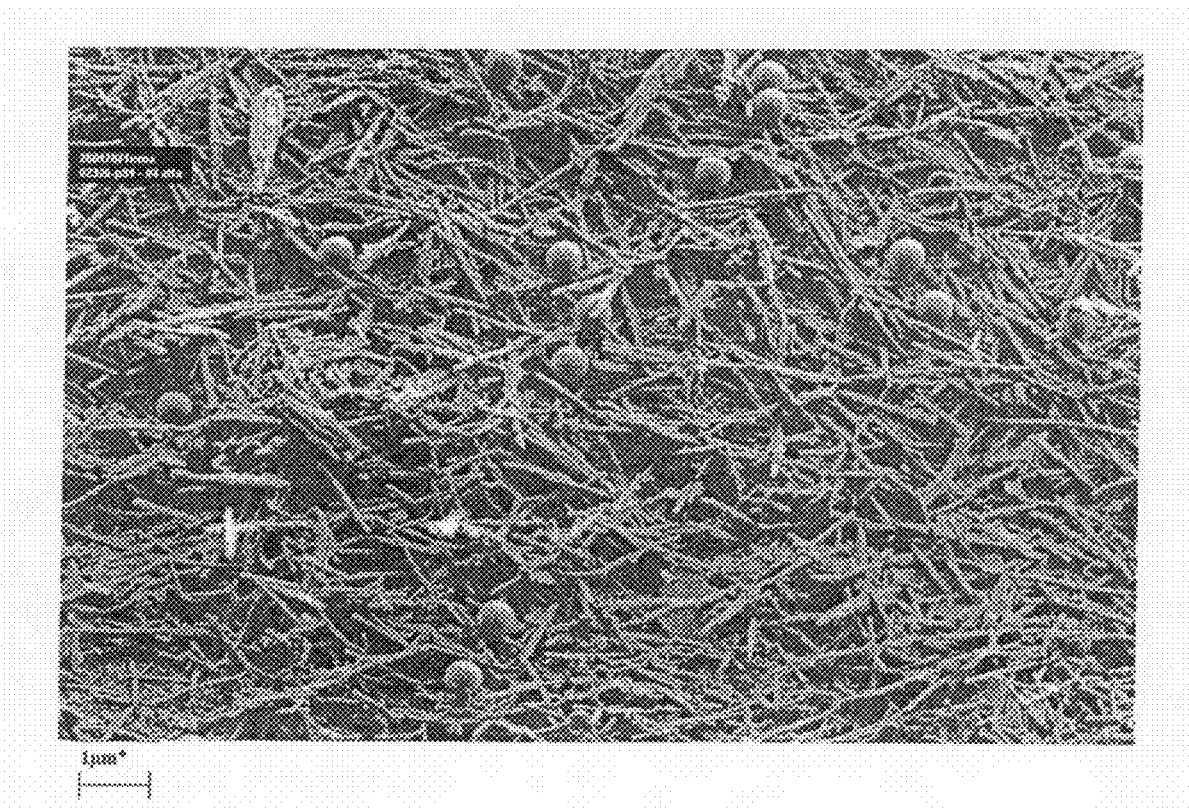
FIG. 11 is an SEM image of a ceramic coating in accordance with an embodiment of the present invention.

A procedure for creating a coating like that illustrated in FIG. 11 will now be described.

PAH solution, PSS solution, and PS particle solution, are prepared as described in Example 1 above. For the sol gel solution, a solution was prepared in which the recipe of Example 1 was halved. Attapulgite particle solution (Atta) is prepared as follows: 50 g/L Attapulgite Clay (ATTAGEL® 50)(BASF) is provided in 25 mM NaCl.

16 mm Liberté™ stainless steel stents are cleaned with an RF oxygen plasma in a March AP-1000 Plasma System using the following process parameters: P=200 mTorr, 300 watts, Gas 1 (Argon)=250 sccm, Gas2 (Oxygen)=200 sccm, t=180s.

The stent is provided with 3.5 bilayers (PAH/PSS/PAH/PSS/PAH/PSS/PAH), followed by 2 bilayers (Atta/PAH/Atta/PAH), followed by a PS particle layer, followed by 2 bilayers (PAH/PSS/PAH/PSS). For each polyelectrolyte layer and the attapulgite particle layers, the stent is immersed in a beaker of PAH, PSS or Atta solution (prepared as described above) and agitated on a shaker for 20 minutes. For the PS particle layer, the stent is immersed in a beaker of the PS particle solution (prepared as described above) and agitated on a shaker for 1 hour. Three DI water rinses are performed after each layer to remove non-adsorbed polyelectrolyte/particles and the stent placed directly into the next solution.

This structure is then submerged in a beaker of sol-gel solution (prepared as described above) for approximately 16 hours, after which three DI water rinses are performed. The resulting structure is placed in an oven at ambient temperature (~23° C.) and ramped to 540° C. over a period of ~1.5 hrs. After a total time of 6 hrs in the oven (ramp-up and 540° C. hold), the oven is turned off, and the sample allowed to cool in the oven overnight.

Example 3

Polyelectrolyte coated carbon nanotubes are prepared as an initial step. Poly(2-(N,N-dimethylaminoethyl) methacrylate (PDMAEMA) (0.15 g)(Sigma Aldrich Bornem, Belgium), NaCl (5.8 g) and 100 mL of deionized water are placed in a 250 mL flask and stirred until the PDMAEMA and NaCl are completely dissolved. The pH value of the solution is adjusted to 3.7 by adding 2 M HCl. Multi-wall carbon nanotubes derivatized with carboxyl groups (MWNT-COOH) (80 mg) (Cheap Tubes, Inc. 112 Mercury Drive, Brattleboro, Vt., USA) are then added to the as-prepared PDMAEMA solution. The mixture is placed in an ultrasonic bath (40 kHz) for 3 min and stirred gently for 30 min. Then the solids are separated by filtration through a 0.22 micrometer Millipore polycarbonate membrane filter and washed with DI water three times. The resulting solids are added to 100 mL of an aqueous solution of PSS (1.5 g/L) (Sigma Aldrich, Bornem, Belgium) and NaCl (1 M) in DI water, followed with the same steps as described above (ultrasonic dispersion, gentle stirring, filtration and washing). Two more bilayers of PDMAEMA and PSS are added. After the final washing step, the resulting particles are suspended in DI water at a concentration of 1 g/L. This solution is substituted for the PS solution in Example 1 above and for the Atta solution in Example 2 above.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A coated article comprising a substrate defining substrate surface, and a ceramic coating that covers at least a portion of the substrate surface, said ceramic coating comprising raised first ceramic shells interconnected by an underlying ceramic layer that is conformal with the substrate surface, the first ceramic shells being at least partially hollow and the at least partially hollow shells containing paramagnetic particles.

2. The coated article of claim 1, wherein said article is a medical article.

3. The coated article of claim 2, wherein said medical article is an implantable or insertable medical device.

4. The coated article of claim 3, wherein said medical device is selected from a stent, an electrical lead, an electrical coil, a catheter, an injection needle, a guidewire, and an embolic device.

5. The coated article of claim 1, wherein said substrate is selected from a metallic substrate and a polymeric substrate.

6. The coated article of claim 1, wherein said ceramic coating contains one or more oxides selected from oxides of silicon, titanium, zirconium, iridium, and combinations thereof.

7. The coated article of claim 1, wherein said ceramic coating contains one or more species selected from carbides and nitrides of silicon, titanium, zirconium, iridium, and combinations thereof.

8. The coated article of claim 1, wherein said first ceramic shells and said underlying ceramic layer comprise at least 90 wt % metal oxide.

9. The coated article of claim 1, wherein said first ceramic shells enclose a material selected from polymeric materials, metallic materials, ceramic materials and carbon.

10. The coated article of claim 1, wherein said first ceramic shells are spherical.

11. The coated article of claim 1, wherein said first ceramic shells are elongated.

12. The coated article of claim 11, wherein said elongated shells are aligned.

13. The coated article of claim 1, further comprising second ceramic shells connected to said first ceramic shells.

14. The coated article of claim 13, further comprising a polymeric coating.

15. The coated article of claim 13, wherein said first and second ceramic shells are spherical.

16. The coated article of claim 13, wherein said first and second ceramic shells are elongated.

17. The coated article of claim 13 wherein said first ceramic shells are spherical and said second ceramic shells are elongated.

18. The coated article of claim 1, wherein said substrate comprises blind holes, through holes or both, and wherein said ceramic shells are preferentially positioned in the holes.

19. The coated article of claim 1, wherein said ceramic coating comprises a metal or semi-metal oxide and a polyelectrolyte.

20. The coated article of claim 19, wherein said ceramic coating further comprises a therapeutic agent.

21. The coated article of claim 1, wherein said ceramic shells enclose a material comprising a therapeutic agent.

22. A coated article comprising
a substrate defining a substrate surface;
a ceramic coating covering at least a portion of the substrate surface, said ceramic coating comprising raised ceramic shells connected by an underlying ceramic layer that is conformal with the substrate surface, and
a polymeric coating covering at least a portion of the ceramic coating, the polymeric coating having a thickness at least not substantially smaller than a height of the raised ceramic shells.

23. The coated article of claim 22, wherein said polymeric coating comprises a therapeutic agent.

24. The coated article of claim 23, wherein said medical device is a stent, said therapeutic agent is an antiproliferative agent, wherein said ceramic coating is disposed over the entire stent, and the polymeric coating is disposed over the abluminal surface of the stent and not disposed over the luminal surface of the stent.

25. The coated article of claim 22, wherein said polymeric coating is selected from a lubricious coating, an electrically insulating coating, a bioresorbable coating and a protein coating.

26. The coated article of claim 22, wherein said ceramic shells are spherical, and wherein the polymeric coating thickness is dictated by the height of the ceramic shells.

27. The coated article of claim 26, wherein the thickness of the polymeric coating is larger than the height of the ceramic shells.

28. The coated article of claim 26, wherein the polymeric coating comprises a bioabsorbable polymer.

29. The coated article of claim 22, wherein the polymeric coating does not extend substantially beyond the height of the ceramic shells.

* * * * *